United States Patent
Ogawa et al.

(10) Patent No.: US 8,367,679 B2
(45) Date of Patent: Feb. 5, 2013

(54) BIARYL CARBOXAMIDES

(75) Inventors: Anthony Ogawa, Mountainside, NJ (US); Hyun O. Ok, Colonia, NJ (US); Debra Ondeyka, Fanwood, NJ (US); Feroze Ujjainwalla, Scotch Plains, NJ (US); Ellen Vande Bunte, Colts Neck, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/130,891

(22) PCT Filed: Dec. 8, 2009

(86) PCT No.: PCT/US2009/067080
§ 371 (c)(1),
(2), (4) Date: May 24, 2011

(87) PCT Pub. No.: WO2010/077624
PCT Pub. Date: Jul. 8, 2010

(65) Prior Publication Data
US 2011/0230498 A1 Sep. 22, 2011

Related U.S. Application Data

(60) Provisional application No. 61/201,283, filed on Dec. 9, 2008.

(51) Int. Cl.
| | |
|---|---|
| A61K 31/497 | (2006.01) |
| A61K 31/4439 | (2006.01) |
| A61K 31/506 | (2006.01) |
| A61K 31/444 | (2006.01) |
| A61K 31/4709 | (2006.01) |
| C07D 401/04 | (2006.01) |
| C07D 401/14 | (2006.01) |
| C07D 413/14 | (2006.01) |

(52) U.S. Cl. .......... 514/255.05; 514/256; 514/314; 514/333; 514/343; 544/333; 544/405; 546/173; 546/256; 546/269.1; 546/279.1

(58) Field of Classification Search ........... 514/255.05, 514/343, 256, 333, 314; 546/279.1, 256, 546/173, 269.1; 544/333, 405
See application file for complete search history.

(56) References Cited

U.S. PATENT DOCUMENTS

| | | | |
|---|---|---|---|
| 6,166,037 | A | 12/2000 | Budhu et al. |
| 6,423,704 | B2 | 7/2002 | Maynard et al. |
| 6,566,359 | B1 | 5/2003 | Bazan et al. |
| 7,230,098 | B2 * | 6/2007 | Cui et al. .......... 544/60 |
| 2003/0149029 | A1 | 8/2003 | McKew et al. |
| 2006/0258672 | A1 | 11/2006 | Barbosa et al. |
| 2007/0191340 | A1 | 8/2007 | Zindell et al. |
| 2008/0182847 | A1 * | 7/2008 | Augeri et al. .......... 514/249 |
| 2009/0048238 | A1 * | 2/2009 | Aebi et al. .......... 514/218 |

FOREIGN PATENT DOCUMENTS

| | | |
|---|---|---|
| DE | 10 2004 061 006 | 6/2006 |
| WO | 01/76582 | 10/2001 |
| WO | 03/042174 | 5/2003 |
| WO | 2006/063791 | 6/2006 |
| WO | 2007/070760 | 6/2007 |
| WO | 2008/045371 | 4/2008 |
| WO | 2008/076778 | 6/2008 |

OTHER PUBLICATIONS

Int'l Search Report in PCT/US2009/067080, dated May 26, 2010.
WO2001/076582, CAS chemical structures, 2012.
CAS Registry No. 955927-92-1, 2008.
Supplementary European Search Report of EP 09836691, mailed Aug. 10, 2012.

* cited by examiner

*Primary Examiner* — Kristin Bianchi
(74) *Attorney, Agent, or Firm* — Carlos S. Quagliato; Catherine D. Fitch

(57) ABSTRACT

This invention provides compounds of Formula (I) which are PAFR antagonists: Formula (I) and the pharmaceutically acceptable salts thereof. The compounds are useful for treating PAF-mediated disorders, and can be used in methods for treating atherosclerosis and preventing or reducing risk for atherosclerotic disease events. The compounds are also useful for treating or ameliorating pain, e.g. inflammatory pain and/or nociceptive pain, and for treating or ameliorating autoimmune and/or inflammatory diseases, among other conditions.

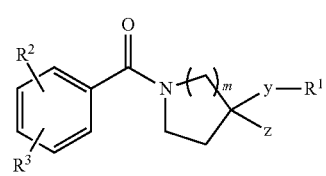

(1)

21 Claims, No Drawings

BIARYL CARBOXAMIDES

TECHNICAL FIELD

This invention relates to amide-substituted benzimidazole and aza-benzimidazole compounds which have platelet activating factor (PAF) receptor antagonist activity, pharmaceutical compositions containing these compounds and methods of treating PAF-mediated disorders, including inflammatory, cardiovascular and immune disorders.

BACKGROUND OF THE INVENTION

Platelet-activating factor (PAF, 1-0-alkyl-2-acetyl-sn-glycerol-3-phosphorylcholine) is a potent inflammatory phospholipid mediator that binds to and activates platelet-activating factor receptor (PAFR). PAF is produced and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. PAF is similar to other lipid mediators such as thromboxane A, prostaglandins, and leukotrienes with respect to the level of potency (active at $10^{-12}$ to $10^{-9}$M), tissue amount (picomoles) and short plasma half life (2-4 minutes). PAF is physiologically active and causes contraction of the airway smooth muscle, increased vascular permeability, platelet aggregation, and hypotension. Reviewed in: Prescott, S. M. et al. *Annu. Rev. Biochem.* 2000, 69, 419-445; Honda et al. *J. Biochem.* 2002, 131, 773-779; Stafforini et al. *Crit. Rev. Clin. Lab Sci.* 2003, 40, 643-672.

PAF has been reported to participate in several aspects of the inflammatory response associated with the pathogenesis of atheroscloerosis, however, the precise role of PAF/PAFR has not been defined. PAF activates the adhesive interaction of leukocytes with the vascular endothelium and the transmigration of leukocytes, promotes the release of reactive oxygen species and tissue-damaging enzymes from leukocytes and endothelial cells, induces the synthesis of inflammatory cytokines from monocytes, and causes the aggregation and degranulation of platelets. In addition, PAF receptor has been shown to recognize both PAF and PAF-like oxidized phospholipids on LDL and may promote an inflammatory response to them (Frostegard, J. et al., *Arterioscler. Thromb. Vasc. Biol.* 1997, 17, 963-968; Leitinger, N. *Curr. Opin. Lipidol.* 2003, 14, 421-430). A PAFR antagonist was reported to reduce atherosclerotic lesion area by 62% in Ldlr−/− mice fed an atherogenic diet (Subbanagounder, G. et al., *Circ. Res.* 1999, 85, 311-318). PAF may also promote smooth muscle cell proliferation, angiogenesis and elastase release. These activities have the potential to contribute to lesion formation or to the generation of occlusive thrombi at the site of plaque rupture (Reviewed in: Demopoulos, C. A. et al., *Eur. J. Lipid Sci. Technol.* 2003, 105, 705-716; Zimmerman, G. A. et al. *Crit. Care Med.* 2002, 30, S294-S301).

PAF has also been implicated in both peripheral and neuropathic pain responses. PAF can induce hyperalgesia when injected subcutaneously into a rat paw (Bonnet, J. et al., *INSERM* 1981, 100, 111; Vargaftig, B. B.; Ferreira, S. H. *Braz. J. Med. Biol. Res.* 1981, 14, 187) and PAFR antagonists were reported to decrease the inflammatory nociceptive response in rats (Mather, L. A. *Psychopharmacology* 2002, 163, 430-433). PAF may also mediate neuropathic pain responses. Intrathecal administration of PAF in mice caused the development of tactile allodynia and thermal hyperalgesia (Morita, K. et al., *Pain* 2004, 111, 351-359). PAF is expressed in the spinal cord and DRG neurons. A PAFR agonist evoked an intracellular $Ca^{2+}$ flux in capsaicin-sensitive DRG but not in Pafr−/− mice, and it has been proposed that PAF may function in both persistent pain and the sensitization of primary sensory neurons after tissue injury (Tsuda, M. et al., *J. Neurochem.* 2007, 102, 1658-1668).

PAF also appears to play a role in pathological allergic, hypersecretory and additional inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. References include: Piper, P. J. et al., *Ann. NY Acad. Sci.* 1991, 629, 112-119; Holtzman, M. J. *Am. Rev. Respir. Dis.* 1991, 143, 188-203; Snyder, F. *Am. J. Physiol. Cell Physiol.* 1990, 259, C697-C708; Prescott, S. M. et al., *J. Biol. Chem.* 1990, 265, 17381-17384; (cardiac diseases) Feuerstein, G. et al., *J Lipid Mediat. Cell Signal.* 1997, 15, 255-284; (liver injury) Karidis, N. P. et al., *World J. Gastroenterol.* 2006, 12, 3695-3706; (pancreatitis) Liu, L. R.; Xia, S. H. *World J. Gastroenterol.* 2006, 12, 539-545; (lung) Uhlig, S. et al., *Pharamcol. Rep.* 2005, 57, 206-221; (thrombosis) Prescott, S. M. et al., *Arterioscler. Thromb. Vasc. Biol.* 2002, 22, 727-733; Ishii, S.; Shimizu, T. *Prog. Lipid Res.* 2000, 39, 41-82. Compounds and/or pharmaceutical compositions which act as PAF receptor antagonists should be of value in the treatment of any of the above conditions.

Despite significant therapeutic advances in the treatment and prevention of atherosclerosis and ensuing atherosclerotic disease events, such as the improvements that have been achieved with HMG-CoA reductase inhibitors, further treatment options are clearly needed. Moreover, there is a need for additional treatment options, in addition to the therapeutics that exist, for the treatment of both inflammatory and neuropathic pain. The instant invention addresses those needs by providing compounds, compositions and methods for the treatment or prevention of atherosclerosis and pain as well as related and other immune conditions.

SUMMARY OF THE INVENTION

The instant invention relates to compounds of Formula I which are PAFR antagonists, methods of their preparation, and methods and pharmaceutical formulations for using these compounds in mammals, especially humans. This invention provides compounds of structural Formula I:

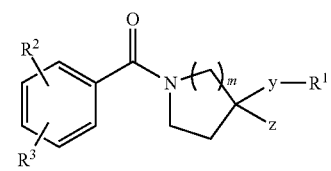

I and the pharmaceutically acceptable salts thereof. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as to treat or ameliorate inflammatory pain and nociceptive pain. They are also useful to treat or ameliorate autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. The instant invention provides methods of treatment comprising administering a therapeutically effective amount of a compound of Formula I to a patient in need of the above-described treatments.

A further object is to provide the use of PAFR inhibitors of Formula I in combination with other therapeutically effective agents, including other drugs useful for the treatment of atherosclerosis and pain. These and other objects will be evident from the description contained herein.

DETAILED DESCRIPTION OF THE INVENTION

The instant invention provides compounds having structural Formula I:

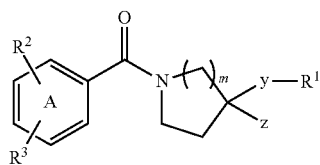

I and the pharmaceutically acceptable salts thereof wherein:
$R^1$ is selected from the group consisting of:
(a) 5-membered heterocyclic ring containing 1 to 4 heteroatoms selected from 1 to 4 of N, zero to 1 of O, and zero to 1 of S, optionally substituted with $R^7$, and
(b) 6-membered heterocyclic ring containing 1 to 2 of N, optionally substituted with $R^7$;
$R^2$ is selected from the group consisting of:
(a) —H,
(b) chloro,
(c) fluoro,
(d) —$C_{1-6}$alkyl optionally substituted with one or more substituents selected from the group consisting of (i) hydroxy, (ii) methoxy, (iii) fluoro,
  (iv) phenyl optionally substituted with one or more substituents selected from the group consisting of —F, —Cl, —OH, —O$C_{1-4}$alkyl optionally substituted with fluoro, and —$C_{1-4}$alkyl optionally substituted with fluoro,
  (v) 5-membered heterocyclic ring containing 1 to 4 heteroatoms selected from 1 to 4 of N, zero to 1 of O, and zero to 1 of S, optionally substituted with $R^5$, and
  (vi) 6-membered heterocyclic ring containing 1 to 2 of N, optionally substituted with $R^5$, (e) —$C_{3-6}$cycloalkyl optionally substituted with one or more substituents selected from the group consisting of fluoro, hydroxy, and methoxy,
(f) phenyl optionally substituted with $R^{5a}$,
(g) 5-membered heterocyclic ring containing 1 to 4 heteroatoms selected from 1 to 4 of N, zero to 1 of O, and zero to 1 of S, optionally substituted with $R^5$,
(h) 6-membered heterocyclic ring containing 1 to 2 of N, optionally substituted with $R^5$,
(i) 9-membered ortho-fused bicyclic heterocyclic ring system containing 1 to 4 heteroatoms selected from 1 to 4 of N and 1 to 2 of O, optionally substituted with one to three of $R^5$,
(j) 10-membered ortho-fused bicyclic heterocyclic ring system containing 1 to 4 of N, optionally substituted with one to three of $R^5$,
(k) cyano,
(l) —$CO_2R^8$,
(m) —$OR^9$,
(n) —(CO)$NR^{10}R^{11}$,
(O) —$NR^{10}R^{11}$,
(p) —NHC(O)$R^8$,
(q) —$NHSO_2R^{12}$,
(r) —NHC(O)$OR^{12}$, and
(s) —NHC(O)$NR^{10}R^{11}$;
$R^3$ is selected from the group consisting of
(a) phenyl substituted with one to three of $R^4$,
(b) 5-membered heterocyclic ring containing 1 to 4 heteroatoms selected from 1 to 4 of N, zero to 1 of O, and zero to 1 of S, substituted with one to three of $R^4$,
(c) 6-membered heterocyclic ring containing 1 to 2 of N, substituted with one to three of $R^4$,
(d) 9-membered ortho-fused bicyclic heterocyclic ring containing 1 to 4 heteroatoms selected from 1 to 4 of N and 1 to 2 of O, substituted with one to three of $R^4$, and
(e) 10-membered ortho-fused bicyclic heterocyclic ring containing 1 to 4 of N, substituted with one to three of $R^4$;
$R^4$ is independently selected at each occurrence from the group consisting of
(a) —H,
(b) fluoro,
(c) chloro,
(d) 5-membered heterocyclic ring containing 1 to 4 heteroatoms selected from 1 to 4 of N, zero to 1 of O, and zero to 1 of S, optionally substituted with —OH, —$NH_2$, —$CH_3$ or —$CF_3$,
(e) —$OC_{1-6}$alkyl optionally substituted with —$C_{3-6}$cycloalkyl or one or more of fluoro,
(f) —$C_{1-6}$alkyl optionally substituted with one or more substituents selected from the group consisting of —$C_{3-6}$cycloalkyl, methoxy, —$OCF_3$, hydroxy and fluoro,
(g) —$NR^{10}R^{11}$,
(h) —$C_{3-6}$cycloalkyl optionally substituted with one of more of fluoro,
(i) —CN, and
(j) —OH;
$R^5$ is independently selected at each occurrence from the group consisting of —F, —Cl, hydroxy, cyano, oxo, —$C_{1-4}$alkyl optionally substituted with fluoro, —$NR^{10}R^{11}$, —$CO_2R^8$, —$SO_2R^{10}R^{11}$, —$CONR^{10}R^{11}$, —$OC_{1-6}$alkyl optionally substituted with —$C_{3-6}$cycloalkyl or fluoro, and —$C_{3-6}$cycloalkyl optionally substituted with one or more substituents selected from the group consisting of —F, —OH, —$OCH_3$, and —$OCF_3$;
$R^{5a}$ is independently selected at each occurrence from the group consisting of —F, —Cl, hydroxy, cyano, —NR$^{10}$R$^{11}$, —C$_{1-4}$alkyl optionally substituted with fluoro, —CONR$^{10}$R$^{11}$, —OC$_{1-6}$alkyl optionally substituted with —C$_{3-6}$cycloalkyl or fluoro, and —C$_{3-6}$cycloalkyl optionally substituted with one or more substituents selected from the group consisting of —F, —OH, —OCH$_3$, and —OCF$_3$;

R$^7$ is selected independently at each occurrence from the group consisting of —F, —Cl, hydroxy, cyano, oxo, amino, —C$_{1-6}$alkyl optionally substituted with fluoro, —C$_{3-6}$cycloalkyl optionally substituted with fluoro, and —OC$_{1-6}$alkyl optionally substituted with fluoro;

R$^8$ is independently selected at each occurrence from the group consisting of —H, —C$_{1-6}$alkyl optionally substituted with phenyl, phenyl optionally substituted with R$^{5a}$, and —C$_{3-6}$cycloalkyl;

R$^9$ is selected from the group consisting of:
 (a) —H,
 (b) —C$_{1-4}$-alkyl optionally substituted with one or more substituents selected from the group consisting of (i) hydroxy, (ii) fluoro, (iii) phenyl optionally substituted with one or more substituents selected from the group consisting of —F, —Cl, —OCH$_3$, —CF$_3$ and —OCF$_3$, and
 (c) —C$_{3-6}$cycloalkyl optionally substituted with one or more substituents selected from the group consisting of fluoro, hydroxy, and —C$_{1-4}$alkyl optionally substituted with fluoro;

R$^{10}$ and R$^{11}$ are each independently selected at each occurrence from the group consisting of
 (a) —H,
 (b) —C$_{1-6}$alkyl optionally substituted with one or more substituents selected from the group consisting of (i) hydroxy, (ii) fluoro, (iii) phenyl optionally substituted with one or more substituents selected from the group consisting of —F, —Cl, —OCH$_3$, —CF$_3$ and —OCF$_3$, and
 (c) —C$_{3-6}$cycloalkyl optionally substituted with one or more substituents selected from the group consisting of fluoro, hydroxy, and —C$_{1-4}$alkyl optionally substituted with fluoro;
or R$^{10}$ and R$^{11}$ together with the nitrogen to which they are both attached represent a ring selected from the group consisting of azetidinyl, pyrrolidinyl, piperidinyl, piperazinyl and morpholinyl, wherein the ring is optionally substituted with a substituent selected from the group consisting of —CH$_3$, —CF$_3$, —F and —OH;

R$^{12}$ is independently selected at each occurrence from the group consisting of
(a) —C$_{1-4}$alkyl optionally substituted with one or more substituents selected from the group consisting of (i) fluoro, (ii) cyano, (iii) hydroxy, (iv) —OCH$_3$ and (v) —OCF$_3$, and
(b) phenyl optionally substituted with one or more of R$^{5a}$;

m is an integer selected from the group consisting of 1 (one) and 2 (two);

y is selected from the group consisting of a bond and —CR$^{6a}$R$^{6b}$—;

z is selected from the group consisting of —H, fluoro, hydroxy, and —C$_{1-4}$alkyl optionally substituted with one or more substituents selected from —OH and —F; and R$^{6a}$ and R$^{6b}$ are independently selected at each occurrence from the group consisting of —H, hydroxy, —OC(O)C$_{1-4}$alkyl, and —OC$_{1-4}$alkyl optionally substituted with one or more of fluoro;
or R$^{6a}$ and R$^{6b}$ are joined together with the carbon to which they are both attached to form a —C$_{3-6}$cycloalk-diyl ring, for example cyclopropyl-1,1-diyl.

In an embodiment of this invention, referred to herein as Formula II, are compounds of Formula I wherein R$^2$ is selected from the group consisting of:
(a) phenyl optionally substituted with R$^{5a}$,
(b) 5-membered heterocyclic ring containing 1 to 4 heteroatoms selected from 1 to 4 of N, zero to 1 of O, and zero to 1 of S, optionally substituted with R$^5$,
(c) 6-membered heterocyclic ring containing 1 to 2 of N, optionally substituted with R$^5$,
(d) 9-membered ortho-fused bicyclic heterocyclic ring system containing 3 to 4 of N, optionally substituted with one to three of R$^5$,
(e) 10-membered ortho-fused bicyclic heterocyclic ring system containing 1 to 4 of N, optionally substituted with one to three of R$^5$,
(f) —C$_{1-6}$alkyl substituted with a substituent selected from the group consisting of
 (i) phenyl optionally substituted with one or more substituents selected from the group consisting of —F, —Cl, —OH, —C$_{1-4}$alkyl optionally substituted with one or more of fluoro, and —OC$_{1-4}$alkyl optionally substituted with one or more of fluoro, and
 (ii) a 5-membered heterocyclic ring containing 1 to 4 heteroatoms selected from 1 to 4 of N, zero to 1 of O, and zero to 1 of S, optionally substituted with R$^5$, and
 (iii) 6-membered heterocyclic ring containing 1 to 2 of N, optionally substituted with R$^5$,
(g) cyano, (h) —CO$_2$R$^8$, (i) —OR$^9$, (j) —(CO)NR$^{10}$R$^{11}$, (k) —NR$^{10}$R$^{11}$, (l) —NHC(O)R$^8$, (m) —NHSO$_2$R$^{12}$, (n) —NHC(O)OR$^{12}$ and (o) —NHC(O)NR$^{10}$R$^{11}$.

In a class of this embodiment, referred to herein as Formula IIa, are compounds of Formula II wherein R$^2$ is selected from the group consisting of:
(a) phenyl optionally substituted with R$^{5a}$,
(b) 5-membered heterocyclic ring containing 1 to 4 heteroatoms selected from 1 to 4 of N, zero to 1 of O, and zero to 1 of S, optionally substituted with R$^5$,
(c) 6-membered heterocyclic ring containing 1 to 2 of N, optionally substituted with R$^5$,
(d) 9-membered ortho-fused bicyclic heterocyclic ring system containing 3 to 4 of N, optionally substituted with one to three of R$^5$, and
(e) 10-membered ortho-fused bicyclic heterocyclic ring system containing 1 to 4 of N, optionally substituted with one to three of R$^5$.

In another class of this embodiment, referred to herein as Formula IIb, are compounds of Formula II wherein R$^2$ is selected from the group consisting of: cyano, —CO$_2$R$^8$, —OR$^9$, —(CO)NR$^{10}$R$^{11}$, —NR$^{10}$R$^{11}$, —NHC(O)R$^8$, —NHSO$_2$R$^{12}$, —NHC(O)OR$^{12}$ and —NHC(O)NR$^{10}$R$^{11}$.

In another embodiment of this invention, referred to herein as Formula III, are compounds of Formula I wherein R$^2$ is selected from the group consisting of:
(a) —H,
(b) chloro,
(c) fluoro,
(d) —C$_{1-6}$alkyl optionally substituted with one or more substituents selected from the group consisting of hydroxy, methoxy, fluoro and chloro, and
(e) —C$_{3-6}$cycloalkyl optionally substituted with one or more substituents selected from the group consisting of hydroxy, methoxy, fluoro and chloro.

In another embodiment of this invention, referred to herein as Embodiment A, are compounds of Formula I, II, IIa, IIb or III wherein R$^3$ is phenyl (ring "B") substituted with one to three of $R^4$, and more particularly wherein $R^3$ is phenyl substituted with one to three of $R^4$ and is attached to ring "A" at the 4-position, i.e.:

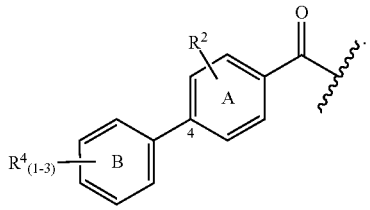

In another embodiment of this invention, referred to herein as Embodiment B, are compounds of Formula I, II, IIa, IIb, III, Embodiment A wherein the $R^2$ and $R^4$ substituents are positioned as shown below:

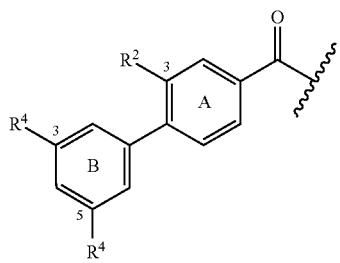

In a further embodiment, referred to herein as Embodiment C, are compounds of Formula I, II, IIa, IIb, III or Embodiment A or B wherein m is one and y is a bond.

In another embodiment of this invention, referred to herein as Embodiment D, are compounds of Formula I, II, IIa, IIb, III, or Embodiment A, B or C wherein $R^1$ is pyridyl optionally substituted with $R^7$.

In another embodiment of this invention are compounds of Formula I, II, IIa, IIb, III, or Embodiment A, B, C or D having structural Formula IV:

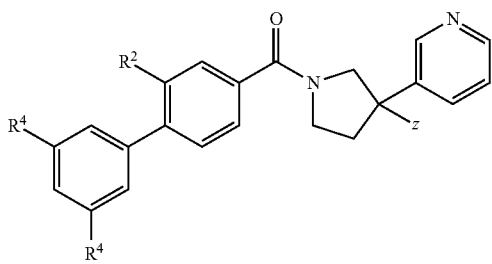

and pharmaceutically acceptable salts thereof, wherein the variable substituents (e.g. z, $R^1$, $R^2$, $R^4$, etc.), are as defined in Formula I, II, IIa, IIb, III, or Embodiment A, B, C or D.

In a preferred class are compounds of Formula IV wherein
z is selected from the group consisting of —H, —F and —OH;
$R^2$ is selected from the group consisting of (a) a heterocyclic ring selected from the group consisting of pyridyl, imidazolyl, pyrimidyl and pyrazinyl, wherein the heterocyclic ring is optionally substituted with a substituent selected from the group consisting of —$NH_2$, —$OCH_3$, —OH, —CN and —F; (b) —$OCF_3$, (c) cyclopropyl and (d) —H; and
$R^4$ is selected from the group consisting of —$CH_3$, $CF_3$ and —$OCH_3$.

In another aspect of this invention are compounds of Formula I, II, IIa, IIb, III or Embodiment A, B or D wherein m is 1.

In another aspect of the present invention are compounds of Formula I, II, IIa, IIb, III or Embodiment A, B or D wherein y is —$CH_2$— or a bond. Preferably, y is a bond. More preferably, m is 1 and y is a bond.

In another aspect of this invention are compounds of Formula I, II, IIa, IIb, III or Embodiment C or D wherein $R^3$ is selected from the group consisting of phenyl, pyridinyl, pyridazinyl, pyrimidinyl, pyrazinyl, pyrazolyl, imidazolyl, quinolinyl, isoquinolinyl, indolyl, benzofuranyl, and benzodioxolyl, each of which is optionally substituted with one to three of $R^4$. Preferably, $R^3$ is phenyl substituted with one to three of $R^4$.

In yet another aspect of this invention are compounds of Formula I, II, IIa, IIb, III, IV or Embodiment A, B, C or D wherein $R^4$ is independently selected at each occurrence from the group consisting of fluoro, chloro, methyl optionally substituted with fluoro (including for example —$CF_3$), and methoxy optionally substituted with fluoro (including for example —$OCF_3$). In another aspect of this invention are compounds wherein $R^3$ is di-substituted with $R^4$. Preferably, both $R^4$ substituents are identical and are selected from fluoro, chloro, methyl optionally substituted with fluoro (including for example —$CF_3$), and methoxy optionally substituted with fluoro (including for example —$OCF_3$). More preferably, both $R^4$ substituents are —$CF_3$.

In another aspect of this invention are compounds of Formula I, II, IIa, IIb, III or Embodiment A, B or C wherein $R^1$ is selected from the group consisting of pyridyl, pyrimidinyl, oxadiazolyl, tetrazolyl, triazolyl, pyrazolyl, thiazolyl, and isoxazolyl, each of which is optionally substituted with $R^7$. Examples of suitable $R^1$ groups include, but are not limited to,

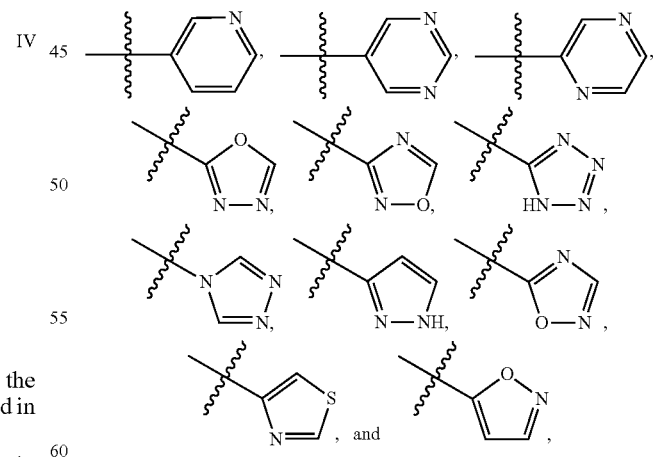

each of which is optionally substituted with $R^7$. Each optional $R^7$ substituent may be attached to the $R^1$ 5-membered heterocyclic ring via any suitable carbon or nitrogen or to the $R^1$ 6-membered heterocyclic ring via any suitable carbon.

When present, $R^7$ is preferably selected from the group consisting of fluoro, chloro, methyl, methoxy, ethoxy, cyano, —CF₃, hydroxy and oxo. More preferably, R⁷ is fluoro, methyl, methoxy, ethoxy, hydroxy, oxo, or absent. Most preferably, R⁷ is absent.

In another aspect of this invention are compounds of Formula I, II, IIa, IIb, III or Embodiment A, B or C wherein R¹ is selected from the group consisting of pyridyl optionally mono-substituted with R⁷ and oxadiazolyl optionally mono-substituted with R⁷. When present on the pyridyl ring, R⁷ is preferably selected from fluoro, methyl, methoxy, and ethoxy. When present on the oxadiazolyl ring, R⁷ is preferably selected from methyl, ethoxy and ethoxy. Preferably, R¹ is unsubstituted pyridyl, oxadiazolyl mono-substituted with methyl, or pyridyl mono-substituted with methyl, methoxy, ethoxy, or fluoro. Most preferably, R¹ is unsubstituted pyridyl.

In another aspect of this invention are compounds of Formulas Formula I or IV or Embodiment A, B, C or D wherein R² is selected from —H; fluoro; chloro; phenyl; —C₁₋₄alkyl optionally substituted with fluoro or hydroxy; —OC₁₋₄alkyl optionally substituted with fluoro or hydroxy; —C₃₋₆cycloalkyl optionally substituted with fluoro; a 5- or 6 -membered heterocyclic ring optionally substituted with R⁵; —CO₂R⁸; —OR⁹; and —CONR¹⁰R¹¹. Examples of suitable 5- and 6-membered monocyclic heterocyclic rings include, but are not limited to, pyrazol-3-yl, pyrazol-4-yl, pyrimidin-2-yl, pyrimidin-5-yl, pyrid-2-yl, pyrid-3-yl, pyrid-4-yl, pyrazinyl, 1,2,4-oxadiazol-3-yl, oxazol-2-yl, and isoxazol-3-yl, each of which may be optionally substituted with R⁵. Preferably, R² is —H, —Cl, —F, methyl, —CF₃, —OCF₃, or —C₃₋₄cycloalkyl, or R² is pyridyl, pyrimidinyl, pyrazinyl, or pyrazolyl wherein each heterocyclic ring is optionally substituted with R⁵.

In another aspect of this invention are compounds of Formula I, II, IIa, IIb, III, IV or Embodiment A, B, C or D wherein R⁵, when present, is selected from the group consisting of amino, methoxy, hydroxy, fluoro, and cyano.

In another aspect of this invention are compounds of Formula I, II, IIa, IIb, III, IV or Embodiment A, B, C or D wherein R⁵ᵃ, when present, is selected from the group consisting of amino, methoxy, hydroxy, ethoxy, methyl, chloro, fluoro, and cyano.

In another aspect of this invention are compounds of Formula I, II, IIa, IIb, III, IV or Embodiment A, B, C or D wherein R⁸, when present, is selected from —H, —C₁₋₄alkyl optionally substituted with phenyl, and —C₃₋₆cycloalkyl optionally substituted with methyl.

In another aspect of this invention are compounds of Formula I, II, IIa, IIb, III, IV or Embodiment A, B, C or D wherein R⁹, when present, is selected from benzyl and —C₁₋₄alkyl optionally substituted with one to three of —F.

In another aspect of this invention are compounds of Formula I, II, IIa, IIb, III, IV or Embodiment A, B, C or D wherein R¹⁰, when present, is selected from the group consisting of —H, —C₃₋₆cycloalkyl, and —C₁₋₄alkyl optionally substituted with hydroxy or fluoro.

In another aspect of this invention are compounds of Formula I, II, IIa, IIb, III, IV or Embodiment A, B, C or D wherein R¹¹, when present, is selected from the group consisting of —H, —C₃₋₆cycloalkyl, and —C₁₋₄alkyl optionally substituted with hydroxy or fluoro. Preferably R¹⁰ and R¹¹ are not both —H and are not both —C₃₋₆cycloalkyl.

In another embodiment aspect of this invention are compounds of Formula I, II, IIa, IIb, III, IV or Embodiment A, B, C or D, wherein R¹⁰ and R¹¹ together with the nitrogen to which they are both attached represent a ring selected from the group consisting of pyrrolidinyl, piperidinyl and morpholinyl, each of which is optionally substituted with a substituent selected from the group consisting of —CH₃, —CF₃, —F and —OH.

In another aspect of this invention are compounds of Formulas Formula I, II, IIa, IIb, III, IV or Embodiment A, B, C or D wherein z is —H, —F or hydroxy. Preferably, z is —H.

In an alternative embodiment of this invention are compounds of Formula I wherein m is one and y is a bond, having structural Formula V:

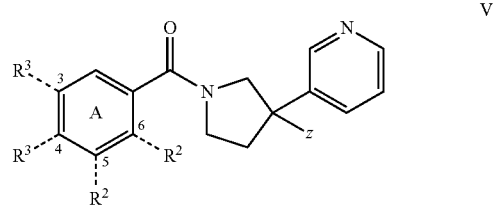

and the pharmaceutically acceptable salts thereof wherein:
z is —H or —OH; R² is bonded to the "A" ring phenyl at either the 5- or the 6-position; and
R³ is bonded to the "A" ring phenyl at either the 3- or the 4-position. The dotted bond "- - -" represents the alternative locations of each of R² and R³ at the noted positions on the "A" ring phenyl.

In particular are compounds of Formula V wherein R² is selected from —H, —F, —CH₃, —CF₃, —OCF₃, and phenyl optionally substituted with R⁵ᵃ; and
R³ is selected from the group consisting of:
  (a) phenyl substituted with one to three of R⁴,
  (b) 5-membered heterocyclic ring containing 1 to 4 heteroatoms selected from 1 to 4 of N, zero to 1 of O, and zero to 1 of S, substituted with one to three of R⁴,
  (c) 6-membered heterocyclic ring containing 1 to 2 of N, substituted with one to three of R⁴,
  (d) 9-membered ortho-fused bicyclic heterocyclic ring containing 1 to 4 heteroatoms selected from 1 to 4 of N and 1 to 2 of O, substituted with one to three of R⁴, and
  (e) 10-membered ortho-fused bicyclic heterocyclic ring containing 1 to 4 of N, substituted with one to three of R⁴.

Examples of R³ groups and examples of optional R⁴ substituents within the scope of Formula V include, but are not limited to, those shown in Tables 2, 2A, 2B and 2C herein.

In an embodiment of Formula V, referred to herein as Formula Va, are compounds wherein R² is —H. In another embodiment referred to as Formula Vb are compounds wherein R³ is present at the 4-position of ring A, and R² is present at the 6-position of ring A and is not —H. In another embodiment referred to as Formula Vc are compounds wherein R³ is present at the 4-position of ring A, and R² is present at the 5-position of ring A and is not —H. In yet another embodiment referred to as Formula Vd are compounds wherein R³ is present at the 3-position of ring A, and R² is present at the 5-position of ring A and is not —H.

Unless specified otherwise, the point of attachment of the R² and R³ groups is via any available carbon in phenyl ring "A."

As used herein, the term "alkyl" means carbon chains which may be linear or branched, or combinations thereof, containing the indicated number of carbon atoms. Examples of alkyl groups include methyl (Me), ethyl (Et), propyl, iso-propyl (i-propyl, ⁱPr), butyl, sec- and text-butyl (s-butyl, t-butyl, sBu, tBu), pentyl, hexyl, and the like. "Cycloalkyl" is intended to be a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule. Preferably, cycloalkyl is cyclopropyl or cyclobutyl, and more particularly, when it is substituted with —$CH_3$ or —$CF_3$, the substituent is on the ring carbon which serves as the point of attachment to the rest of the molecule.

"Halogen" (Halo) includes fluoro, chloro, bromo and iodo. Preferred halogens are —F and —Cl, more preferably —F.

As used herein, "heterocyclic ring" and "heterocycle" mean an aromatic or partially unsaturated heterocyclic ring containing one or more carbon atoms and one or more heteroatoms selected from nitrogen (N), oxygen (O) and sulfur (S), in total containing 5 to 6 atoms in the ring. A bicyclic heterocyclic ring system similarly means an aromatic or partially unsaturated bicyclic ring system containing one or more carbon atoms and one or more heteroatoms selected from nitrogen (N), oxygen (O) and sulfur (S), in total containing 9 to 10 atoms in the ring. For mono- and bicyclic heterocyclic rings containing one or more of N, it is understood that the nitrogen may be present in the ring as =N— or —NH— in accordance with the degree of unsaturation in the ring. A heterocyclic ring or bicyclic ring system may be more specifically defined where appropriate in the specification, for example with respect to the number of members (i.e. atoms) in the ring and/or the type and quantity of heteroatoms in the ring, or the point of attachment between two rings in a bicyclic ring system. Examples of aromatic or partially unsaturated heterocyclic rings include but are not limited to pyridyl, pyrimidyl, imidazolyl, tetrazolyl, triazolyl, pyrazolyl, thiazolyl, isoxazolyl, and the like. For 5-membered aromatic or partially unsaturated heterocyclic rings, the point of attachment in a compound structure may be via any available carbon or nitrogen in the ring which results in the creation of a stable structure, unless specified otherwise. For 6-membered aromatic or partially unsaturated heterocyclic rings, the point of attachment in a compound structure may be via any available carbon in the ring which results in the creation of a stable structure, unless specified otherwise. The heterocyclic ring or ring system may be substituted on any available carbon or nitrogen in the ring which results in the creation of a stable structure.

The phrase "9-membered ortho-fused bicyclic heterocyclic ring system" as used herein means a 6-membered ring and a 5-membered ring wherein the rings have two, and only two, adjacent atoms in common, i.e., they are ortho-fused. The phrase "10-membered ortho-fused bicyclic heterocyclic ring system" as used herein means two 6-membered rings ortho-fused together. Said bicyclic ring systems are comprised of carbon atoms and the indicated number and kind of heterotaoms, and may be substituted as defined herein. Examples of suitable ortho-fused bicyclic heteroaryls include benzothiophene, quinoline, isoquinoline, benzofuran, and the like. Additional examples of bicyclic heterocyclic ring systems are shown in the Examples and Tables herein.

The phrases "optionally substituted" and "optionally substituted with one or more substituents" are both intended to mean that the total number of substituents on the optionally substituted moiety overall may be zero, one or more than one, and that each carbon and heteroatom (when present) available for substitution in the given moiety may independently be unsubstituted or mono- or poly-substituted, with one or more substituents that are the same or different at each occurrence and which result in the creation of a stable structure as is understood to be reasonable by one skilled in the art. In some instances the number of substituents which may optionally be present on a moiety is specified, for example but not limited to, 1 to 3 of fluoro and mono- or di-substituted with $R^4$. For example, $C_{1-3}$alkyl optionally substituted with fluoro includes, but is not limited to, —$CH_3$, —$CH_2F$, —$CHF_2$, —$CF_3$, —$CH_2CH_3$, —$CH_2$—$CH_2F$, —CHF—$CH_2F$, —$CF_2$—$CF_3$, —$CH(CF_3)$—$CH_3$, —$CF_2$—$CF_2$—$CF_3$, and the like; methyl optionally substituted with 1 to 3 of fluoro includes —$CH_3$, —$CH_2F$, —$CHF_2$ and —$CF_3$; and phenyl optionally mono- or di-substituted with $R^4$ includes

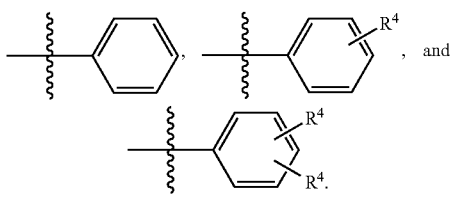

Some of the compounds encompassed herein may exist as tautomers, e.g., ketoenol tautomers. For the purpose of illustration, when $R^1$ is a 5-membered heterocyclic ring and $R^7$ is oxo or —OH, the resulting compound may be capable of tautomerism, as exemplified below:

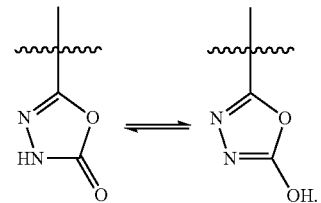 [SMILES: *c1n[nH]c(=O)o1 ; *c1nnc(O)o1]

Other nitrogen-containing heterocycles can also exist as tautomers. Examples include but are not limited to:

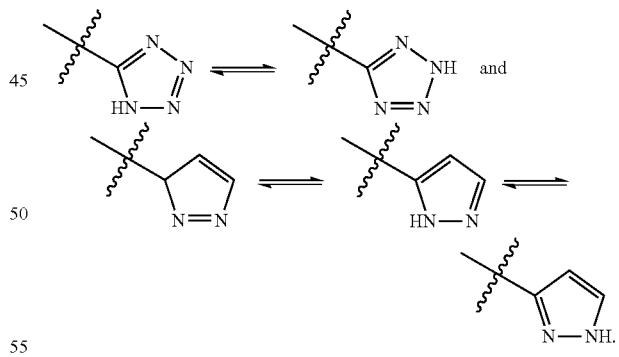

Where compounds of this invention are capable of tautomerization, all individual tautomers as well as mixtures thereof are included in the scope of this invention.

Reference to the compounds of this invention as those of a specific formula or embodiment (e.g., Formula I, Formula II, Embodiment A, etc.) or any other generic structural formula or specific compounds described or claimed herein is intended to encompass the specific compound or compounds falling within the scope of the generic structural formula or embodiments including salts thereof, particularly pharmaceutically acceptable salts, as well as the esters and/or solvates of such compounds and salts thereof, where such forms are possible unless specified otherwise. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, trifluoroacetic, maleic, phosphoric, sulfuric, and tartaric acids.

Any pharmaceutically acceptable pro-drug modification which results in conversion in vivo to an active form of a compound within the scope of this invention is also within the scope of this invention. For example, esters can optionally be made by esterification of an available carboxylic acid group or by formation of an ester on an available hydroxy group in a compound. Pharmaceutically acceptable esters of the compounds of this invention may serve as pro-drugs which can be hydrolyzed back to their acid or hydroxy form particularly in vivo and as such are encompassed within the scope of this invention. Examples of pharmaceutically acceptable esters include, but are not limited to, —$C_{1-4}$alkyl esters and —$C_{1-4}$alkyl substituted with phenyl esters.

The compounds of Formula I may contain one or more asymmetric centers, and can thus occur as racemates, racemic mixtures, single enantiomers, diastereoisomeric mixtures and individual diastereoisomers. The present invention includes all such isomers, as well as salts, esters and/or solvates of such racemates, mixtures, enantiomers and diastereoisomers. Compounds of structural Formula I may be separated into their individual diastereoisomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, synthesis can be performed using one or more chiral intermediates which results in a chiral final product.

Furthermore, compounds of the present invention may exist in amorphous or crystalline physical forms, and a single compound may exist in more than one polymorphic crystalline form. All such physical forms are intended to be included in the scope of the present invention. In addition, some of the compounds of the instant invention may form solvates with water (hydrates) or with common organic solvents. Such solvates and hydrates are likewise encompassed within the scope of this invention.

Accordingly, the compounds within the generic structural formulas and specific compounds described and claimed herein encompass salts thereof, esters thereof, and salts of esters thereof where such forms are possible unless specified otherwise. The instant invention further encompasses all possible stereoisomers, physical forms (e.g., amorphous and crystalline forms), solvate forms, tautomers and combinations of these forms of the compounds falling within the generic structural formulas as well as the specific compounds described and claimed herein, the salts thereof, esters thereof, and salts of esters thereof, where such forms are possible unless specified otherwise.

This invention involves the use of the PAF receptor antagonist compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of Formula I of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. Accordingly, the instant invention also provides a method for preventing or reducing the risk of a first or subsequent occurrence of an atherosclerotic disease event comprising the administration of a prophylactically effective amount of a compound of Formula I to a patient at risk for such an event.

The patient may already have atherosclerotic disease at the time of administration, or may be at risk for developing it.

This invention also involves the use of compounds of Formula I described herein to treat or ameliorate inflammatory pain and nociceptive pain in mammals, and especially in humans. Therefore, one object of the instant invention is to provide a method for treating pain, comprising administering a therapeutically effective amount of a compound of Formula I to a patient in need of such treatment. Another object is to provide methods for preventing or reducing the risk of developing inflammatory and nociceptive pain, comprising administering a prophylactically effective amount of a compound of Formula I to a patient who is at risk of developing inflammatory or nociceptive pain.

Compounds and/or pharmaceutical compositions which act as PAF receptor antagonists appear to play a role in pathological allergic, hypersecretory and inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, myocardial infarction, inflammatory bowel diseases, pain, edema, rhinitis, thrombosis, bronchitis, urticaria, psoriasis, retinal and corneal diseases, chemically induced liver cirrhosis, and ovimplantation in pregnancy, and acute respiratory distress syndrome. Accordingly, another object of the instant invention is to provide a method for treating a PAF receptor mediated medical condition, particularly a pathological allergic, hypersecretory and/or inflammatory condition including those conditions described above, comprising administering a therapeutically effective amount of a compound of Formula I to a patient in need of such treatment.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment atherosclerosis or pain, and a prophylactically effective amount, e.g., for prevention of an atherosclerotic disease event or inflammatory or neuropathic pain.

In general, PAFR antagonists can be identified as those compounds which have an $IC_{50}$ in the "PAF Binding Assay" that is less than or equal to about 1 µM, and preferably 200 nM or less, and most preferably 40 nM or less.

An effective amount of a PAFR antagonist in the method of this invention is in the range of about 0.1 mg/kg to about 100 mg/kg of body weight per day, preferably 0.1 mg to about 30 mg per kg, in single or divided doses. A single daily dose is preferred but not necessary. For an average body weight of 70 kg, the dosage level is therefore from about 7 mg to about 2000 mg of drug dosed one to four times per day, e.g. 10 mg, 25 mg, 50 mg, 75 mg, 100 mg, 125 mg, 150 mg, 175 mg, 200 mg, 250 mg, 500 mg, 1000 mg, 1500 mg, or 2000 mg per dose, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the PAFR antagonist will administered chronically on a daily basis for a length of time appropriate to treat or prevent the medical condition relevant to the patient, including a course of therapy lasting months, years or the life of the patient.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for preventing or reducing the risk of developing atherosclerotic disease, halting or slowing the progression of atherosclerotic disease once it has become clinically manifest, and/or preventing or reducing the risk of a first or subsequent occurrence of an atherosclerotic disease event. A compound of this invention can also be used for the preparation of a medicament useful for treating pain. Additionally, a compound of this invention can be used for the preparation of a medicament useful for the treatment of a pathological allergic, hypersecretory and/or inflammatory condition including such conditions described herein. The medicament comprised of a compound of this invention may also be prepared with one or more additional active agents, such as those described below.

One or more additional active agents may be administered with a compound of Formula I. The term "additional active agent (or agents)" is intended to mean a pharmaceutically active agent (or agents) different from the compound of Formula I. In a broad embodiment, any suitable additional active agent or agents, including but not limited to anti-atherosclerotic agents such as a lipid modifying compound, anti-diabetic agents and/or anti-obesity agents, and additional pain-reducing agents may be used in any combination with the compound of Formula I in a single dosage formulation, or may be administered to the patient in one or more separate dosage formulations, which allows for concurrent or sequential administration of the active agents. The additional active agent or agents may have more than one pharmaceutical activity, for example it may have both lipid-modifying effects and anti-diabetic activity. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (MEVACOR® see U.S. Pat. No. 4,342,767), simvastatin (ZOCOR® see U.S. Pat. No. 4,444,784), pravastatin, particularly the sodium salt thereof (PRAVACHOL® see U.S. Pat. No. 4,346,227), fluvastatin particularly the sodium salt thereof (LESCOL® see U.S. Pat. No. 5,354,772), atorvastatin, particularly the calcium salt thereof (LIPITOR® see U.S. Pat. No. 5,273,995), pitavastatin also referred to as NK-104 (see PCT international publication number WO 97/23200) and rosuvastatin (CRESTOR®; see U.S. Pat. No. 5,260,440); cholesterol absorption inhibitors (CAI), for example ezetimibe (ZETIA®) or a combination of a CAI with a statin such as ezetimibe with simvastatin (VYTORIN®) or with atorvastatin; 5-lipoxygenase inhibitors; cholesterol ester transfer protein (CETP) inhibitors, for example anacetrapib or JTT-705; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR and LXR ligands including both inhibitors and agonists; and bisphosphonate compounds such as alendronate sodium. Anti-obesity agents can be employed in combination with a compound of this invention including, but not limited to, sibutramine, orlistat, topiramate, naltrexone, bupriopion, phentermine, and phentermine/topiramate combination (QNEXA®); NPY5 antagonists; Acetyl-CoA Carboxylase-1 and -2 (ACC) inhibitors; MCH1R antagonists; and CB1 antagonists/inverse agonists such as those described in WO03/077847 and WO05/000809. Additional anti-diabetes agents which may be employed in combination with a compound of this invention include but are not limited to DPP-4 (dipeptidylpeptidase-4) inhibitors such as sitagliptin (JANUVIA®, JANUMET®) and vildagliptin (GALVUS®); sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor antagonists; and glucokinase activators. Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, and the calcium antagonists nifedipine, diltiazem, nitrendipine, verapamil, nimodipine, felodipine, etc. Compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®); corticosteroids such as hydrocortisone, methylprednisolone, betamethasone, dexamethasone, beclomethasone, and the like; with leukotriene receptor antagonists such as montelukast (e.g., SINGULAIR®); phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Still other types of agent that can be used in combination with the compounds of this invention for the treatment of pain are non-steroidal anti-inflammatory drugs (NSAIDs), for example aspirin, ibuprofen, ketoprofen, and naproxen; non-opioid analgesics such as acetaminophen; and cyclooxygenase-2 (COX-2) inhibitors such as etoricoxib (ARCOXIA®) and celecoxib (CELEBREX®).

In the method of treatment of this invention, the PAFR antagonists may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No.

5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients.

The compounds of structural Formula I of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. All temperatures are degrees Celsius unless otherwise noted. Mass spectra (MS) were measured by electron-spray ion-mass spectroscopy (ES-MS).

The instant compounds are generally isolated in a pharmaceutically acceptable form which can either be the free base or an appropriate salt derivative, such as those described above. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization.

Some abbreviations used herein are as follows: ABCA1 is adenosyltriphosphate-binding cassette-family A1; Ac is acetyl; AcOH is acetic acid; AIBN is 2,2'-azobis(2-methylpropionitrile); aq. is aqueous; Ar is Aryl; Atm. is atmospheric pressure units; Bn is benzyl; Boc is tertbutylcarbamoyl; br is broad; Bu is butyl; $^c$Bu is cyclobutyl; $^i$Bu is isobutyl; $^t$Bu is tert-butyl; celite is Celite® diatomaceous earth; conc. is concentrated; cpm is counts per minute; δ is chemical shift; d is doublet; DAST is diethylaminosulfur trifluoride; DBU is 1,8-diazabicyclo[5.4.0]undec-7-ene; DCE is 1,2-dichloroethane; DCM is dichloromethane; d is doublet; DEAD is diethylazodicarboxylate; DIAD is diisopropylazodicarboxylate; DIBAL-His diisobutylaluminum hydride; DIPEA is diisopropylethylamine; DMAP is 4-dimethylaminopyridine; DME is 1,2-dimethoxyethane; DMF is N,N-dimethylformamide; dppf is 1,1'-bis(diphenylphosphino)ferrocene; DMSO is dimethyl sulfoxide; dppf is 1,1'-Bis(diphenylphosphino) ferrocene; EDC is N-(3-dimethylaminopropyl)-N'-ethylcarbodiimide hydrochloride; EDTA is ethylendiamine tetraacetic acid; equiv. is equivalent(s); ES-MS is electrospray ion-mass spectroscopy; Et is ethyl; $Et_2O$ is diethyl ether; EtOH is ethanol, EtOAc is ethyl acetate; FXR is farnesoid X receptor; g is gram; h is hours; HATU is O-(7-azabenzotriazol-1-yl)-N,N,N',N'-tetramethyluronium hexafluorophosphate; HetAr or HAR is Heteroaryl; HMG-CoA is 3-hydroxy-3-methylglutaryl coenzyme A; $^1$H NMR is proton nuclear magnetic resonance; HOAt is 1-hydroxy-7-azabenzotriazole; HOBt is 1-hydroxybenzotriazole; HPLC is high performance liquid chromatography; Hz is hertz; i is Iso; $IC_{50}$ is concentration at which 50% inhibition exists; J is internuclear coupling constant; kg is kilogram; LDA is lithium diisopropylamide; LG is leaving group; LHMDS is lithium bis(trimethylsilyl)amide; $LTB_4$ is leukotriene $B_4$; LXR is liver X receptor; m is multiplet; M is molar; Me is methyl; m.p. is melting point; mg is milligram; μg is microgram; MeCN is acetonitrile; MeOH is methanol; MHz is megahertz; min is minute; mL is milliliter; mm is millimeter; μL is microliter; mM is milimolar; μM is micromolar; mmol is milimoles; Ms is methanesulfonyl; MS is mass spectrum, and a mass spectrum obtained by ES-MS may be denoted herein by "ES"; m/z is mass to charge ratio; n is normal; N is normal; NaHMDS is sodium bis(trimethylsilyl)amide; NBS is N-bromosuccinimide; NIS is N-iodosuccinimide; nm is nanometer; nM is nanomolar; NMM is N-methylmorpholine; NMO is N-methylmorpholine-N-oxide; NMP is N-methylpyrrolidin-2-one; Pr is propyl; $^c$Pr is cyclopropyl; $^i$Pr is isopropyl; $^n$Pr is n-propyl; $^i$PrOH is isopropyl alcohol; p is pentet; p is para; PEG is polyethylene glycol; Ph is phenyl; Phth is phthalimidoyl; PPARα is peroxisome proliferator activated receptor alpha; p-TSA is para-toluenesulfonic acid; PyBOP is benzotriazole-1-yl-oxy-tris-pyrrolidino-phosphonium hexafluorophosphate; q is quartet; rt is room temperature; s is singlet; satd. is saturated; sec is secondary; t is triplet; $^t$BuOH is tert-butanol; tert is tertiary; Tf is trifluoromethanesulfonyl; TFA is trifluoroacetic acid; and THF is tetrahydrofuran; TMS is trimethylsilyl; Ts is tosyl; UV is ultraviolet; wt is weight; wt. % is weight percent; w/v is weight/volume ratio; x g is times gravity; °C. is degrees Celsius.

In the Schemes, all substituents are as defined above unless indicated otherwise. Reaction schemes A-P illustrate the methods employed in the synthesis of the compounds of the present invention of structural Formula I. All abbreviations are as defined above unless indicated otherwise.

Reaction scheme A illustrates a preferred method for the synthesis of compounds of type 2. In this reaction, an aryl amine of type 1 is treated with a suitable, organic soluble, activating reagent, such as tert-butyl nitrite or isoamyl nitrite, or the like, in the presence of a halogenated metal capable of transferring a single halogen atom, such as copper(II) bromide, or the like. The reaction is typically run in an inert solvent, such as acetonitrile or THF, at reaction temperatures generally between 0° C. and room temperature. An alternate method is commonly referred to as the Sandmeyer reaction, whereby compounds of type 1 are treated with sodium nitrite in the presence of a protic acid with a weakly nucleophilic conjugate base, such as concentrated sulfuric acid, or the like, in a mixture of suitable solvents, such as EtOH and water, or the like, at 0° C. for 15-30 min. At this time, a suitable halogen source, such as sodium iodide or copper(I) iodide, or the like, is added, and the reaction is continued at 0° C. for 15-60 min. The product of either method is an aryl halide of type 2 that can be elaborated to compounds of the present invention (I) as described in the subsequent schemes.

Scheme A

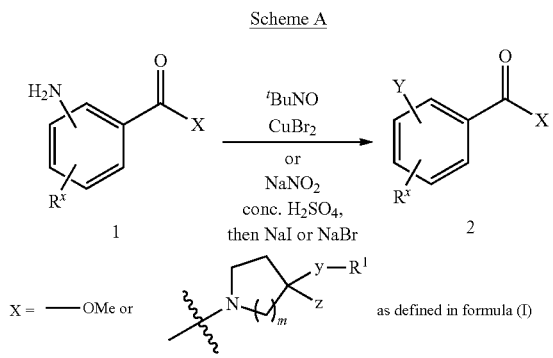

Y = Br or I
$R^x$ = either $R^2$ or $R^3$, or a group that could be converted to $R^2$ or $R^3$, as defined in formula (I)

Reaction scheme B illustrates an alternate method for the synthesis of compounds of type 4, that represent a regiospecific subset of compounds of type 2. The product of the reaction (4) is synthesized using a process commonly referred to as C-H activation, using methodology developed by Sanford, et al. (*Org. Lett.* 2006, 8, 2523-2526). In this reaction a suitable $R^w$ group, such as 2-pyridyl or 1,2,4-oxadiazol-3-yl, directs Pd(II) insertion into a C—H bond on compounds of type 3, using a suitable pre-catalyst, such as palladium acetate, by coordinating to palladium via a lone pair of electrons on $R^w$. The reaction is run in the presence of a suitable halogenated oxidizing agent, such as N-bromosuccinimide or N-iodosuccinimide, that facilitates the oxidation of the palladium-aryl complex, followed by reductive elimination to afford a single regioisomer aryl halide of type 4. The reaction can be run in a number of suitable solvents, such as acetic acid or acetonitrile, typically at 100° C. for 12 h. The reaction may be accelerated by the use of a microwave reactor at elevated temperatures. The product (4) can be elaborated to compounds of the present invention (I) as described in the subsequent schemes.

Scheme B

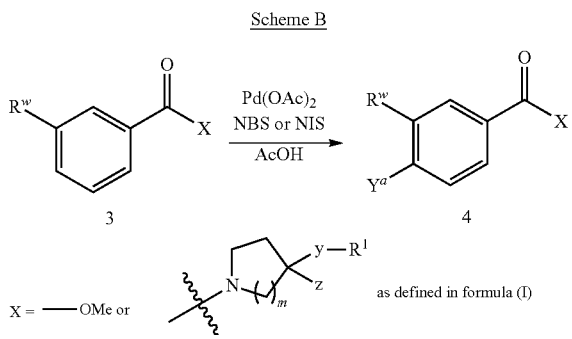

$Y^a$ = Br, I
$R^w$ = a suitable group as defined by $R^2$, such as,
but limited to, 2-pyridyl or 1, 2, 4-oxadiazol-3-yl Reaction scheme C illustrates using the Suzuki reaction for the synthesis of compounds of type 8. Compound 5 can be treated with an aryl- or heteroaryl-boronic acid of type 6, or alternatively, an aryl- or heteroaryl-boronate of type 7, in the presence of a suitable palladium catalyst, such as [1,1'-bis(diphenylphosphino)ferrocene]dichloropalladium(II), or tetrakis(triphenylphosphine)palladium (0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Conditions suitable for performing Suzuki reactions at room temperature have been reported in the literature (see: *J. Am. Chem. Soc.* 2000, 122, 4020-4028, and references therein). In addition, the reaction may be accelerated by the use of a microwave reactor. The product of the reaction (8) can be elaborated to compounds of the present invention (I) as described in the subsequent schemes.

Scheme C

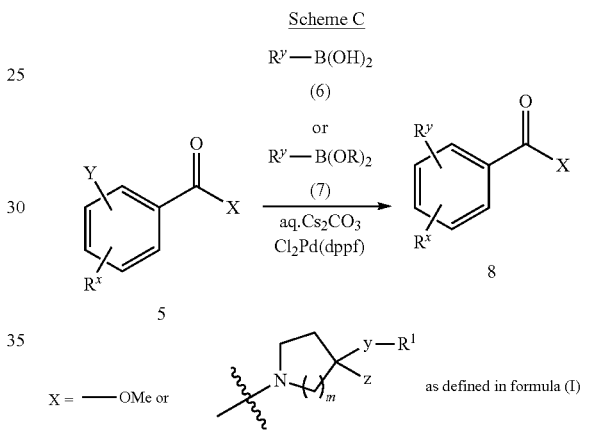

Y = Br, I, OTf
$R^x$ = either $R^2$ or $R^3$, or a group that could be converted to $R^2$ or $R^3$, as defined in formula (I);
$R^y$ = either $R^2$ or $R^3$, or a group that could converted to to $R^2$ or $R^3$, as defined in formula (I); and such that only one each of $R^2$ and $R^3$, or a group that could be converted to $R^2$ or $R^3$, are present in 8.

Reaction scheme D illustrates a method for the elaboration of compound 9. In this method, 9 is treated with a heterocycle (Het-H, 10), such as pyrazole, in a copper-catalyzed N-arylation reaction. (Similar copper-catalyzed N-arylation chemistry wherein Het-H could be imidazole or 1,2,4-triazole has also been developed.) The reaction is commonly catalyzed by a suitable copper(I) reagent, such as copper(I) iodide, or the like, in the presence of a ligand, such as 1,10-phenanthroline or trans-N,N'-dimethylcyclohexane-1,2-diamine, in a suitable solvent, such as toluene, DMF or DMSO, or the like, at reaction temperatures generally between 100° C. and the boiling temperature of the reaction mixture, for periods up to 24 h. The reaction requires the presence of a suitable base, such as cesium carbonate, or potassium phosphate tribasic, or the like. (*J. Org. Chem.* 2004, 69, 5578-5587) Recent literature cites the use of copper(I) oxide and salicylaldoxime as the catalyst and ligand, respectively, to effect the N-arylation reaction, (*Eur. J. Org. Chem.* 2004, 2004, 695-709) In addition, the reaction may be accelerated by the use of a microwave reactor. The product of the reaction is a heterocyclic-substituted compound of type 11, such that the aforementioned heterocycle is bonded to the central phenyl ring through an endocyclic nitrogen, which can be elaborated to compounds of the present invention (I) as described in the subsequent schemes.

Scheme D

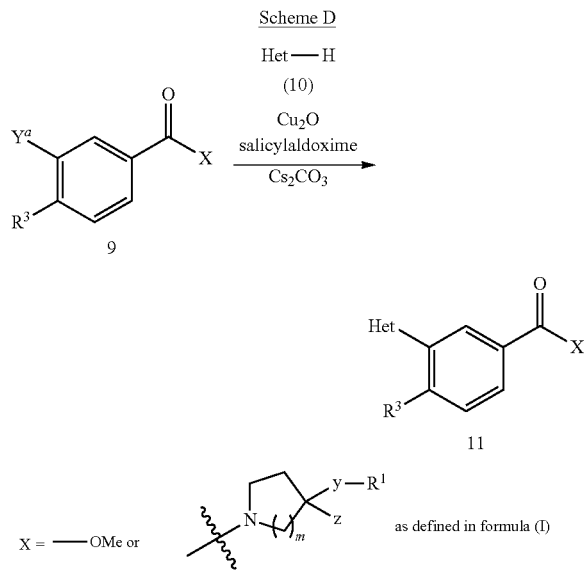

X = —OMe or 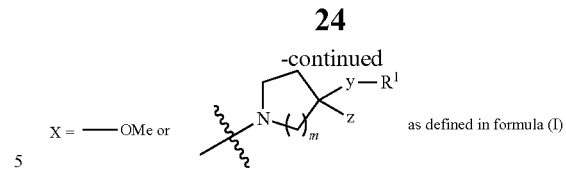 as defined in formula (I)

$Y^a$ = Br, I

Het = preferably pyrazole, but also imidazole or 1,2,4-triazole, bonded to the central phenyl ring through a nitrogen on Het Reaction scheme E illustrates a method for the elaboration of compound 12 to afford compound 13. In this method, 12 is treated with methanol in the presence of a suitable palladium catalyst, such as [1,1'-bis(diphenylphosphino)-ferrocene] dichloropalladium(II), or the like, and a tertiary amine base, such as triethylamine, or diisopropylethylamine, or the like, in an inert organic solvent like dimethylformamide. The reaction is usually conducted at elevated temperature, typically between 50° C. and 100° C., for periods of 3 -24 h, under an atmosphere of carbon monoxide (*J. Org. Chem.* 1974, 39, 3318-3326). In certain cases, it may be preferable to use elevated pressures of carbon monoxide, or an additive, such as lithium chloride, to promote or accelerate the reaction. The product ester 13 can be elaborated to compounds of the present invention (I) as described in the subsequent schemes.

Scheme E

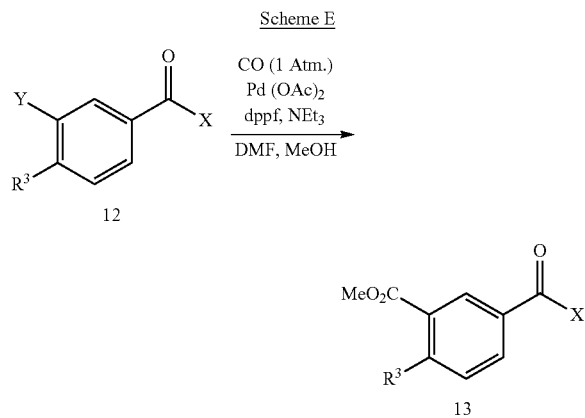

Reaction scheme F illustrates a method for the elaboration of compound 12 to afford compound 14. In this method, 12 is reacted with potassium cyanide, or a similar cyanide source, such as trimethylsilylcyanide, or the like, in the presence of a suitable palladium catalyst/ligand system. It may be preferable to use an inorganic additive, such as copper(I) iodide, and/or a mild base, such as triethylamine, to accelerate or promote the reaction. The reaction is usually performed in a suitable degassed inert organic solvent, preferably a polar aprotic solvent, such as acetonitrile, DMF or NMP, at elevated temperatures, generally between 50-140° C., for a period of 3-24 h. The product nitrile 14 can be elaborated to compounds of the present invention (I) as described in the subsequent schemes.

Scheme F

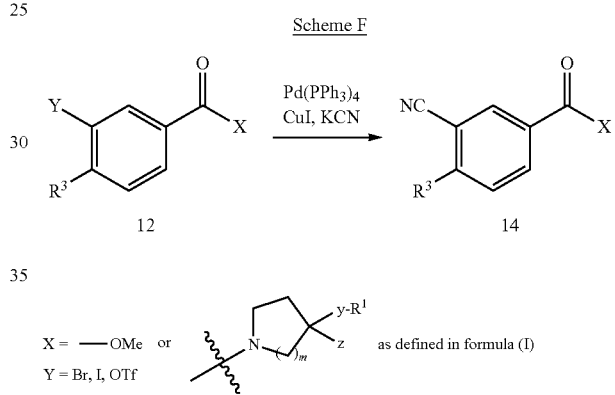

X = —OMe or ... as defined in formula (I)
Y = Br, I, OTf

Reaction scheme G illustrates a preferred method for the synthesis of compounds of type 18. In this method, a protected aminoalcohol of type 15 is reacted in the presence of triphenylphosphine and an activating agent, such as carbon tetrabromide, for which the conjugate base from the initial reaction, bromide ion, subsequently participates in a nucleophilic displacement of the activated alcohol moiety. The reaction can be run in a number of inert solvents, such as THF, acetonitrile or DCM, and is commonly initiated at reduced temperatures, such as 0° C., while permitting slow warming to room temperature. The product of the reaction is a bromide of type 16 that is treated with a boronic acid (17) in the presence of a suitable catalyst, such as nickel diiodide, and ligand, such as trans-2-aminocyclohexanol, according to the procedures reported by Fu, et al. (*J. Am. Chem. Soc.* 2006, 128, 5360-5361), in a modification of the method commonly referred to as the Suzuki reaction. The reaction requires the addition of a suitable base, such as sodium bis(trimethylsilyl) amide, and is typically assembled and run under an inert atmosphere, preferably with the assistance of a glove box, generally at temperatures between 60° C. and 80° C. for between 5-12 h. The product of the reaction is a substituted cyclic amine of type 18, which can be elaborated to compounds of the present invention (I) as described in the subsequent schemes.

Scheme G

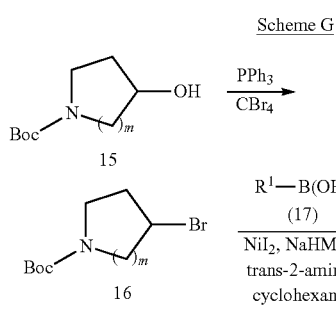

Reaction scheme H illustrates a general method for the synthesis of compounds of type 21. In this method, commercially available amine (19) is treated with an activating acid, such as TFA or the like, in the presence of a suitable olefin of type 20 in a [3+2] cycloaddition reaction in which amine 19 in activated by the acid source such that it can subsequently participate in the cycloaddition reaction. (Terao, Y., et al. Chem. Pharm. Bull. 1985, 33, 2762-2766) The reaction is typically conducted at room temperature in an inert solvent, such as DCM or benzene, or the like. The product of the reaction is a pyrrolidine of type 21, which can be elaborated to compounds of the present invention (I) as described in the subsequent schemes.

Scheme H

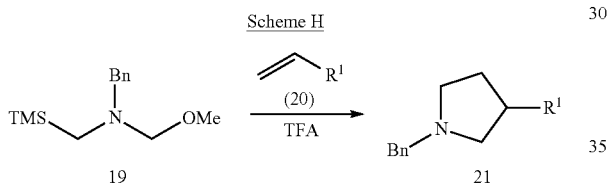

Reaction scheme I illustrates an alternate general method for the synthesis of compounds of type 18. In this method, a cyclic amine ketone of type 22 is treated with a base, such as lithium bis(trimethylsilyl)amide, or LDA, or the like, followed by the addition of a suitable triflating reagent, such as triflic anhydride. The reaction is typically performed in an etheral solvent, such as diethyl ether, or THF, or a mixture thereof, at −78° C. The product of the reaction is a vinyl triflate of type 23 that is reacted with an aryl boronic acid of type 17 in a method commonly referred to as a Suzuki reaction. The reaction is performed in the presence of a suitable palladium catalyst, such as [1,1'-bis(diphenylphosphino)ferrocene]-dichloropalladium(II), or tetrakis(triphenylphosphine)palladium(0), or the like, and a mild base, such as sodium carbonate, sodium phosphate tribasic, or the like (Pure Appl. Chem. 1991, 63, 419-422). The reaction is usually performed in a suitable degassed aqueous mixture of inert solvents, such as toluene, ethanol or dioxane, at elevated temperatures, generally between 70° C. and the boiling temperature of the reaction mixture, for a period of 3-24 h. Recently, conditions suitable for performing Suzuki reaction at room temperature have been published (for example, see: J. Am. Chem. Soc. 2000, 122, 4020-4028, and references therein). The product of the reaction is a vinyl compound of type 24 that is converted to a saturated cyclic amine of type 18 by treatment with a suitable palladium catalyst, such as palladium on carbon, at either atmospheric or elevated pressures of hydrogen. The reaction is usually conducted in an inert solvent, such as EtOH or EtOAc, or a mixture thereof, at room temperature for a period of 3-5 h. The cyclic amine product 18 can be elaborated to compounds of the present invention (I) as described in the subsequent schemes.

Scheme I

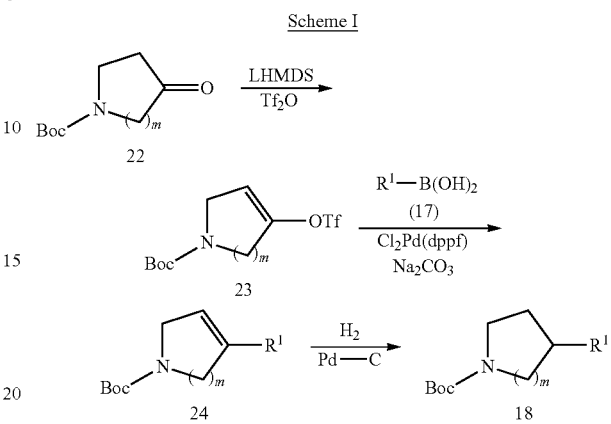

Reaction scheme J illustrates a general method for the synthesis of compounds of type 26. In this method, a cyclic amine ketone of type 22 is treated with an organometallic reagent of type 25, commonly referred to as Grignard or Gilman reagents, capable of transferring an aryl group, to afford a tertiary alcohol of type 26. It is customary to conduct the reaction in a suitable etheral solvent, such as diethyl ether or THF, or a mixture thereof, at temperatures between −78° C. and room temperature. The product of the reaction, a tertiary alcohol of type 26 can be elaborated to compounds of the present invention (I) as described in the subsequent schemes.

Scheme J

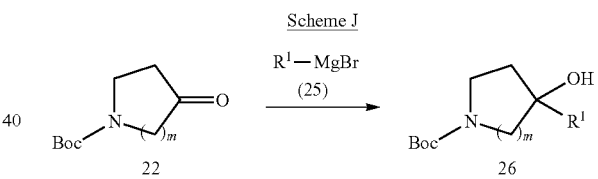

Reaction scheme K illustrates a general method for the synthesis of compounds of type 27. In this method, a tertiary alcohol of type 26 is treated with a fluorinating reagent, such as DAST or Deoxofluor™, in a suitable inert solvent, such as DCM, at −78° C. The product of the reaction, fluoride 27 can be elaborated to compounds of the present invention (I) as described in the subsequent schemes.

Scheme K

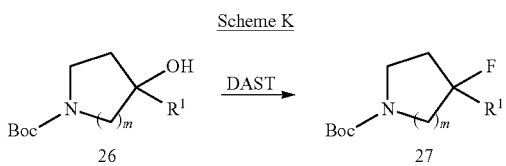

Reaction scheme L illustrates a general method for the synthesis of compounds of type 33, wherein v=a suitable —$C_{1-4}$alkyl substituent optionally substituted with —F, as defined for substituent "z" in Formula I. In this method, an aryl ketone of type 28 is treated with a phosphonate anion to afford an α,β-unsaturated ester (29) in a reaction commonly known as the Horner-Emmons reaction. The phosphonate reagent, trimethylphosphonoacetate, or the like, is initially treated with a suitable base, such as sodium hydride, typically in an etheral solvent, such as diethyl ether or THF, commonly between 0° C. and room temperature, following which, the ketone (28) is added to the reaction mixture. The product is an α,β-unsaturated ester of type 29 that is treated with an excess of nitromethane in the presence of a suitable base, such as cesium carbonate, or the like, in an inert polar aprotic solvent, such as DMSO, at elevated temperatures between 120° C. and the boiling point of the reaction mixture. In addition, the reaction may be accelerated by the use of a microwave reactor. The product of the reaction is a γ-nitroester of type 30, which is treated under similar reaction conditions as those described above in Scheme I for the reduction of 24 to amine 18. The direct product of the reaction, a γ-aminoester of type 31, can spontaneously undergo cyclization to a lactam of type 32 during the reduction step, to afford a crude mixture of both amine 31 and lactam 32. This product mixture can be converted to a lactam of type 32 by heating at elevated temperatures between 40° C. and the boiling point of the reaction mixture in a suitable inert solvent, such as EtOH. It is common to add a suitable base, such as potassium carbonate, or a catalyst, such as DMAP, to accelerate the reaction. The product of the reaction is a lactam of type 32 that is treated with a suitable reducing agent, such as borane-THF complex, or the like, in an inert solvent, such as THF or toluene, at elevated temperatures between 50° C. and the boiling temperature of the reaction mixture for 1-24 h. It is common to heat the reaction mixture in an appropriate sealed vessel. The product of the reaction is an amine of type 33, which can be elaborated to compounds of the present invention (I) as described in subsequent schemes.

Scheme L

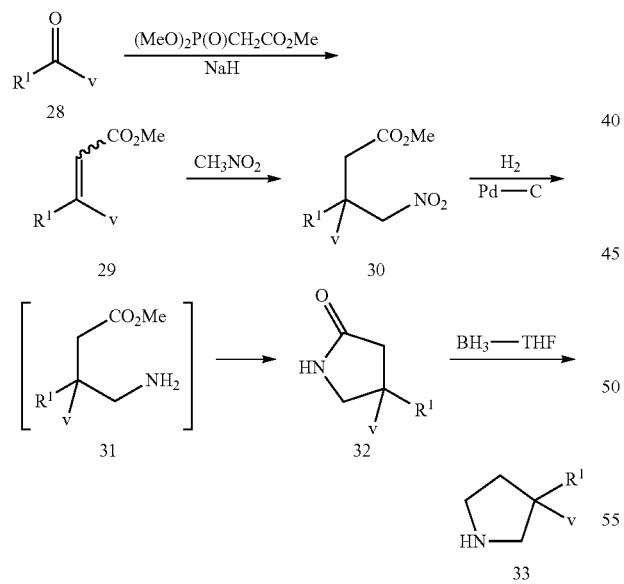

v = a suitable —C$_{1-4}$alkyl substituent optionally substituted with —F, as defined for substituent "z" in Formula I Scheme M illustrates that compounds of structural formula 34 can be elaborated to a variety of heterocyclic (HAR) derivatives of structural formula 35 using known methods in organic synthesis. Specific examples of such transformations are shown in the Examples section. Leading references for effecting such transformations include:

Joule, J. A.; Mills, K. and Smith, G. F. *Heterocyclic Chemistry*, Chapman & Hall, 1995, 3rd Edn., and references cited therein;

Katrittzky, A. R.; Rees, C. W. (Eds), *Comprehensive Heterocyclic Chemistry: The Structure, Reactions, Synthesis, and Uses of Heterocyclic Compounds*, Pergamon Press, Oxford, 1984, 8v, and references cited therein; and Comprehensive Heterocyclic Chemistry II: Review of the Literature 1982-1995: The Structure, Reactions, Synthesis and Uses of Heterocyclic Compounds, Pergamon Press, New York, 2nd Edn., 1996, 11v, and references cited therein.

Scheme M

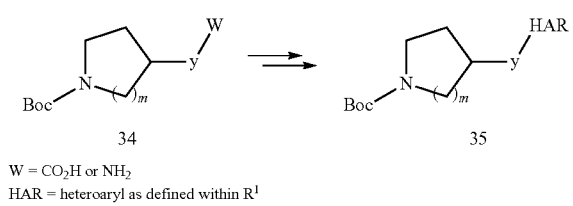

W = CO$_2$H or NH$_2$
HAR = heteroaryl as defined within R$^1$

Scheme N illustrates methods for the syntheses of compounds of type 39. In this scheme, an ester of type 36 can be hydrolyzed to a carboxylic acid of type 37 using methods known to those skilled in the art of organic synthesis. The product of the reaction is an aryl carboxylic acid of type 37 that can participate in amide bond coupling reactions with an amine of type 38 to afford an amide structural formula 39, in an appropriate inert solvent such as DMF, DCM or the like and may be performed with a variety of reagents suitable for amide coupling reactions such as HATU, EDC or PyBOP. Preferred conditions for the amide bond coupling reaction shown in reaction Scheme N are known to those skilled in organic synthesis. Such modifications may include, but are not limited to, the use of basic reagents such as triethylamine, DIPEA, or NMM, or the addition of an additive such as DMAP, HOAt or HOBt.

Scheme N

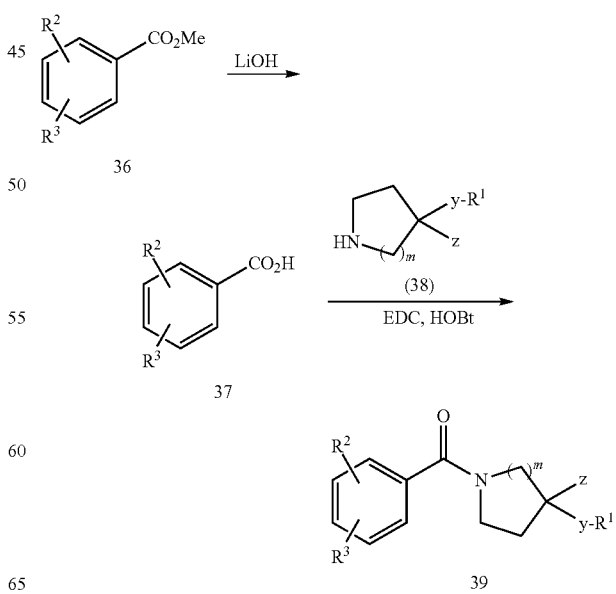

Scheme O illustrates that compounds of structural formula 40 can be elaborated to a variety of heterocyclic (HAR) derivatives of structural formula 41 using known methods in organic synthesis as indicated previously in Scheme M. Specific examples of such transformations are shown in the Examples section.

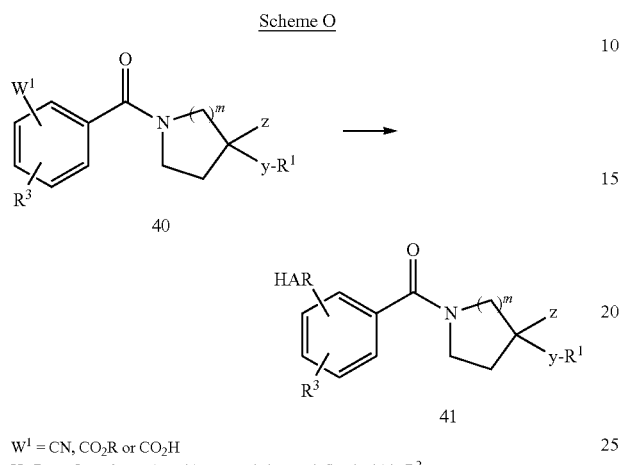

W¹ = CN, CO₂R or CO₂H
HAR = a 5- or 6-membered heteroaryl ring as defined within R²

Scheme P illustrates a method for the resolution of representative compounds or intermediates of structural formula 42. Generally, representative compounds, or intermediates en route to their preparation, may be resolved to afford enantiomerically pure compounds such as 43 and 44 by chiral stationary phase liquid chromatography techniques or other suitable methods known in organic synthesis.

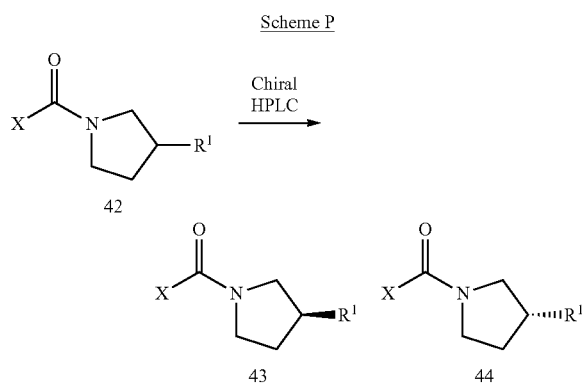

X = a suitable protecting group, or any structure consistent with the structural formula I.

Intermediates used in the synthesis of compounds of this invention can be prepared using the following procedures. In the Tables associated with the following Schemes, compounds having mass spectral data were synthetically prepared.

For compounds that were enantiomerically resolved according to the procedures described in Scheme P and other Schemes and Examples herein, the slower eluting enantiomers yielded preferable IC$_{50}$ results in the PAF Binding Assay over the corresponding faster eluting enantiomers, with the exception of compound 1Ar, where the faster eluting enantiomer was preferred. The absolute stereochemistry of the isolated enantiomers was not determined.

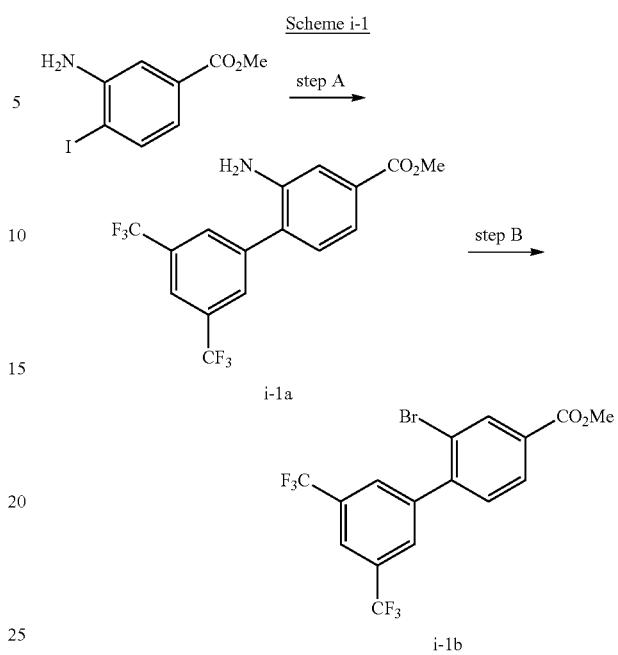

Preparation of i-1b

Step A: Preparation of methyl 2-amino-3',5'-bis(trifluoromethyl)biphenyl-4-carboxylate (i-1a)

[1,1'-Bis(diphenylphosphino)ferrocene]dichloropalladium(II) (265 mg, 0.360 mmol) was added to a solution of methyl 3-amino-4-iodobenzoate (2.00 g, 7.22 mmol), 3,5-bistrifluorophenylboronic acid (2.05 g, 7.94 mmol) and sodium carbonate (5.40 mL of a 2.0 M aqueous solution, 10.83 mmol) in EtOH:toluene (12.0 mL of an 80:20 mixture, respectively) at rt. The resulting solution was heated to 125° C. in a sealed microwave vial for 20 min. After cooling to rt, the reaction mixture was filtered through a short column of Celite®, eluting with EtOAc. The filtrate was washed with water and brine, dried (sodium sulfate) and concentrated in vacuo. The crude residue was purified by flash chromatography on silica gel (isocratic elution; 10% EtOAc/hexanes as eluent) to furnish the title compound i-1a. m/z (ES) 364 (MH)⁺.

Step B: Preparation of methyl 2-bromo-3',5'-bis(trifluoromethyl)biphenyl-4-carboxylate (i-1b)

tert-Butyl nitrite (697 μL, 5.86 mmol) was added to a stirred suspension of copper(II) bromide (1.05 g, 4.69 mmol) in acetonitrile (40.0 mL) at 0° C. After 5 min, i-1a (1.42 g, 3.91 mmol) was added in one portion, and the resulting suspension was warmed slowly to rt. After 24 h, the reaction mixture was quenched with 1.0 M HCl and partially concentrated to approximately half of the original volume. The resulting mixture was extracted with ether, and the combined organics were washed with brine, dried (magnesium sulfate) and concentrated in vacuo. The crude residue was purified by flash chromatography on silica gel (isocratic elution; 5% EtOAc/hexanes as eluent) to afford the title compound i-1b. ¹H NMR (500 MHz, CDCl₃): δ 8.42 (d, 1H, J=1.6 Hz), 8.11 (dd, 1H, J=1.6, 8.1 Hz), 7.97 (m, 1H), 7.46 (m, 2H), 7.46 (d, 1H, J=8.0 Hz), 4.00 (s, 3H).

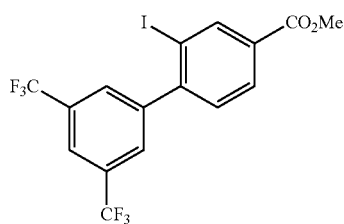

i-1c

Preparation of methyl 2-iodo-3',5'-bis(trifluoromethyl)biphenyl-4-carboxylate (i-1c)

A sodium nitrite solution (456 mg in 5.00 mL of water, 6.61 mmol) was added slowly dropwise to a stirred solution of i-1a (1.60 g, 4.40 mmol) and conc. sulfuric acid (1.40 mL, 26.3 mmol) in DME:water (2.5:1 mixture, respectively) at 0° C. After 30 min, a sodium iodide solution (1.98 g in 5.00 mL water, 13.2 mmol) was added, and the resulting mixture was allowed to stir at 0° C. for an additional 30 min. The reaction mixture was quenched with 1.0 M sodium thiosulfate and extracted with ether. The combined organics were washed with brine, dried (magnesium sulfate) and concentrated in vacuo. The crude residue was purified by flash chromatography on silica gel (gradient elution; 0%-20% EtOAc/hexanes as eluent) to afford the title compound i-1c.

Following procedures similar to those described for the preparation of intermediate i-1b and i-1c, the following compounds in Table i-1 can be prepared.

TABLE i-1 i-1A: X = Br
i-1B: X = I i-1C: X = Br
i-1D: X = I
R = suitable group as defined for $R^2$ or $R^3$ in formula I.

| Ex. 1A | Ex. 1B | Ex. 1C | Ex. 1D | R |
|---|---|---|---|---|
| — | — | a | a | 3,5-bis(CF$_3$)phenyl |
| b | b | b | b | 3,5-dimethylphenyl |
| c | c | c | c | 3,5-dichlorophenyl |
| d | d | d | d | Ph |
| e | e | e | e | 3-OMe-5-CF$_3$-phenyl |
| f | f | f | f | 3-F-5-CF$_3$-phenyl |
| g | g | g | g | 2,5-dichlorophenyl |
| h | h | h | h | 4-OMe-3-CF$_3$-phenyl |
| i | i | i | i | 2,3,5-trichlorophenyl |

TABLE i-1-continued

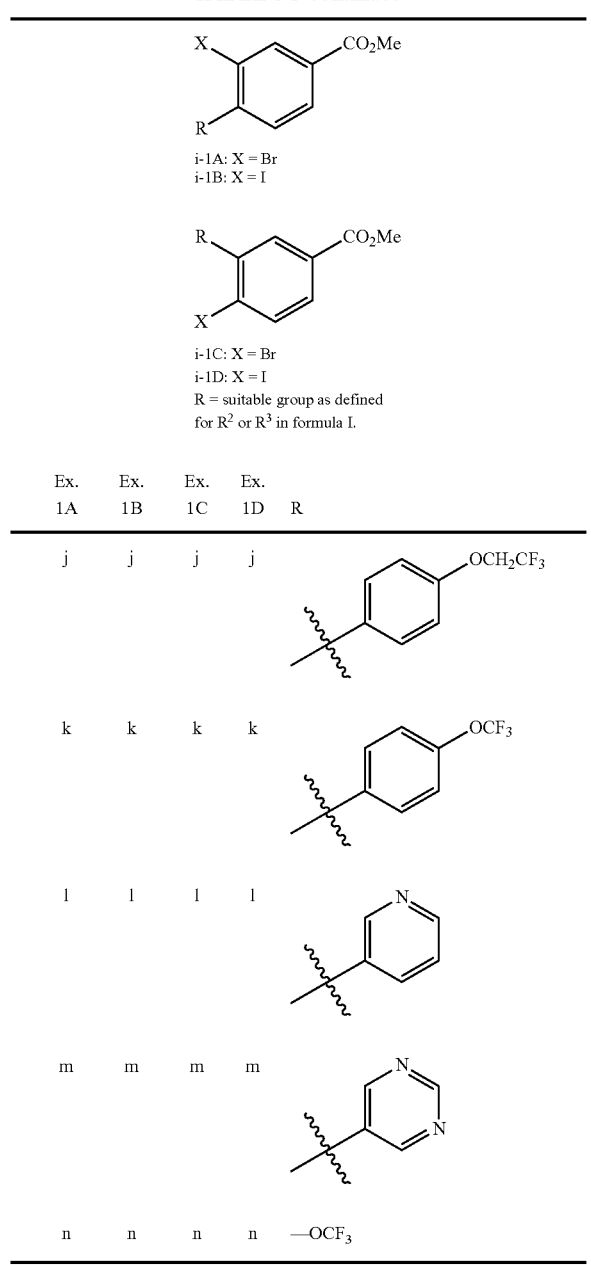

i-1A: X = Br
i-1B: X = I i-1C: X = Br
i-1D: X = I
R = suitable group as defined for $R^2$ or $R^3$ in formula I.

| Ex. 1A | Ex. 1B | Ex. 1C | Ex. 1D | R |
|---|---|---|---|---|
| j | j | j | j | —C₆H₄—OCH₂CF₃ (4-OCH₂CF₃-phenyl) |
| k | k | k | k | —C₆H₄—OCF₃ (4-OCF₃-phenyl) |
| l | l | l | l | 3-pyridyl |
| m | m | m | m | 5-pyrimidinyl |
| n | n | n | n | —OCF₃ |

Parent Ion m/z (MH)+ Data for Compounds i-1Bd: 338.

Scheme i-2

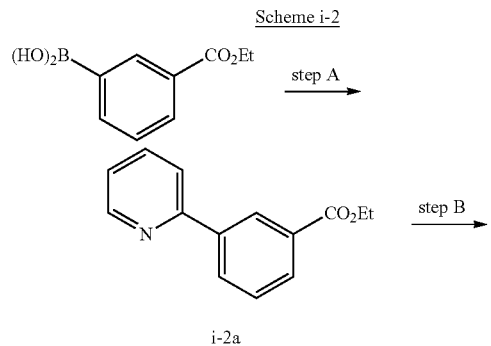

Preparation of i-2b

Step A: Preparation of ethyl 3-pyridin-2-ylbenzoate (i-2a)

Tetrakis(triphenylphosphine)palladium(0) (208 mg, 0.180 mmol) was added to a solution of 3-ethoxycarbonylphenyl boronic acid (350 mg, 1.80 mmol), 2-bromopyridine (189 μL, 1.99 mmol) and potassium carbonate (499 mg, 3.61 mmol) in EtOH:toluene (4.00 mL of an 80:20 mixture, respectively) at rt. The resulting solution was heated to 100° C. in a sealed microwave vial for a total of 15 min. After cooling to rt, the reaction mixture was filtered through a short column of Celite®, eluting with EtOAc. The filtrate was washed with water and brine, dried (sodium sulfate) and concentrated in vacuo. The crude residue was purified by flash chromatography on silica gel (isocratic elution; 10% EtOAc/hexanes as eluent) to afford the title compound i-2a. m/z (ES) 228 (MH)+.

Step B: Preparation of ethyl 4-bromo-3-pyridin-2-ylbenzoate (i-2b)

Palladium acetate (3.95 mg, 0.180 mmol) was added to a solution of i-2a (80.0 mg, 0.352 mmol) and N-bromosuccinimide (125 mg, 0.704 mmol) in acetic acid (2.00 mL). The resulting mixture was heated to 160° C. in a sealed microwave vial for 10 min. After cooling to rt, the reaction mixture was concentrated in vacuo. The crude residue was purified by flash chromatography on silica gel (isocratic elution; 15% EtOAc/hexanes as eluent) to afford the title compound i-2b. m/z (ES) 307 (MH)+.

Scheme i-3

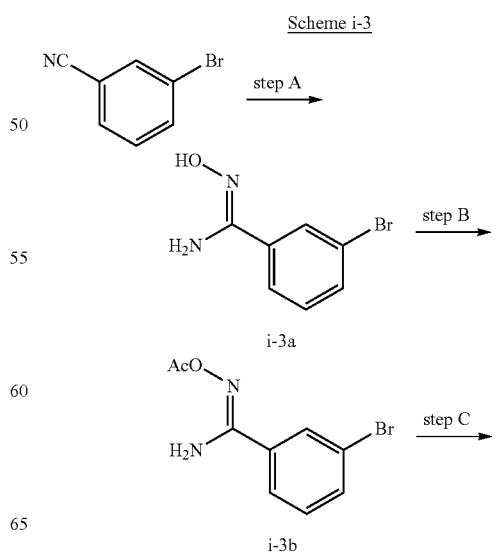

Step D: Preparation of methyl 3-(5-methyl-1,2,4-oxadiazol-3-yl)benzoate (i-3d)

Palladium (II) acetate (24.0 mg, 0.107 mmol) and 1,1'-bis(diphenylphosphino)ferrocene (118 mg, 0.213 mmol) were added to a stirred solution of i-3c (255 mg, 1.07 mmol) in triethylamine:DMF:methanol (10.5 mL of a 1:10:10 mixture, respectively) at rt. The reaction mixture was saturated with carbon monoxide and then heated to 70° C. under a carbon monoxide Atmosphere (balloon) for approximately 4 h. After cooling to rt, the reaction mixture was filtered through a short column of Celite®, eluting with DCM. The filtrate was partially concentrated in vacuo and diluted with EtOAc. The organic phase was washed with water and brine, dried (sodium sulfate) and concentrated in vacuo. Purification of the crude residue by flash chromatography on silica gel (isocratic elution; 20% EtOAc/hexanes as eluent) afforded the title compound i-3d. m/z (ES) 219 (MH)$^+$.

Step E: Preparation of methyl 4-bromo-3-(5-methyl-1,2,4-oxadiazol-3-yl)benzoate (i-3e)

Compound i-3e was prepared following procedures similar to those described for the preparation of i-2b, substituting i-3d for i-2a. m/z (ES) 297 (MH)$^+$.

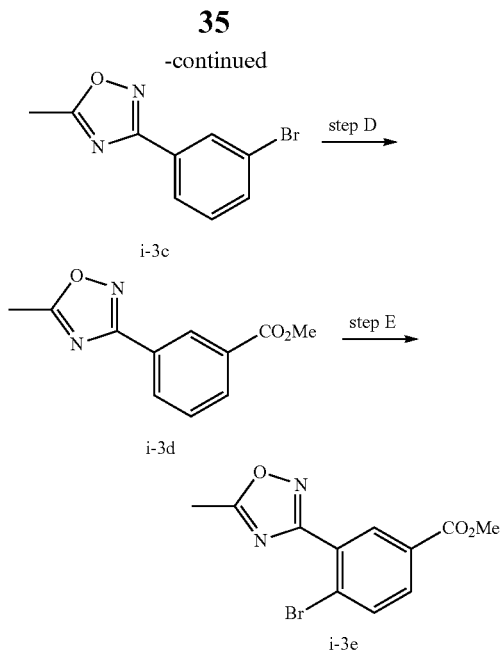

Preparation of i-3e

Step A: Preparation of 3-bromo-N'-hydroxybenzenecarboximidamide (i-3a)

Hydroxylamine (1.00 mL of a 50% aqueous solution, 16.3 mmol) was added to a solution of 3-bromobenzonitrile (750 mg, 4.12 mmol) and potassium carbonate (1.00 mg, 7.24 μmol) in EtOH (3.00 mL). The resulting mixture was heated to 120° C. in a sealed microwave vial for 40 min. After cooling to rt, the reaction mixture was concentrated in vacuo to afford the title compound i-3a. m/z (ES) 215 (MH)$^+$.

Step B: Preparation of N'-(acetyloxy)-3-bromobenzenecarboximidamide (i-3b)

N-(3-Dimethylaminopropyl)-N'-ethylcarbodiimide hydrochloride (562 mg, 193 mmol) was added to a stirred solution of i-3a (525 mg, 2.44 mmol), acetic acid (168 μL, 2.93 mmol) and 1-hydroxybenzotriazole (486 mg, 3.17 mmol) in DCM (10.0 mL). The resulting mixture was allowed to stir at rt for 20 min, at which time the reaction mixture was concentrated in vacuo. The crude residue was purified by flash chromatography on silica gel (gradient elution; 25%-50% EtOAc/hexanes as eluent) to afford the title compound i-3b. m/z (ES) 257 (MH)$^+$.

Step C: Preparation of 3-(3-bromophenyl)-5-methyl-1,2,4-oxadiazole (i-3c)

A solution of i-3b (417 mg, 1.62 mmol) in toluene (5.00 mL) was heated to reflux. The reaction flask was equipped with a Dean-Stark trap, and molecular sieves were added to the reaction mixture. After 5 h, the reaction mixture was filtered and concentrated in vacuo. The crude residue was purified by flash chromatography on silica gel (gradient elution; 0%-40% EtOAc/hexanes as eluent) to afford the title compound i-3c. m/z (ES) 239 (MH)$^+$.

Scheme i-4

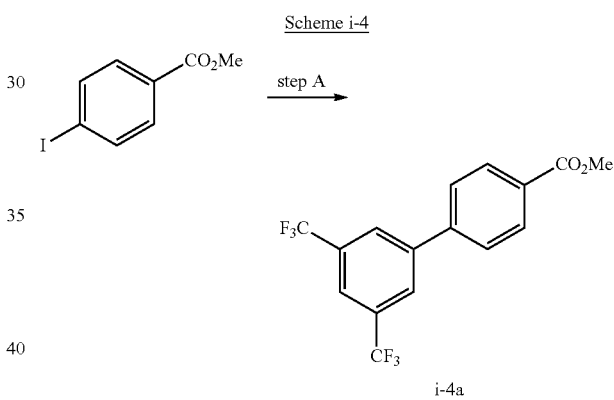

Preparation of i-4-a

Step A: Preparation of methyl 3',5'-bis(trifluoromethyl)biphenyl-4-carboxylate (i-4-a)

Compound i-4-a was prepared following procedures similar to those described for the preparation of i-1a, substituting methyl 4-iodobenzoate for methyl 3-amino-4-iodobenzoate. m/z (ES) 349 (MH)$^+$. $^1$H NMR (500 MHz, CDCl$_3$): δ 8.20 (d, 2H, J=8.2 Hz), 8.07 (s, 2H), 7.93 (s, 1H), 7.71 (d, 2H, J=8.4 Hz), 4.00 (s, 3H).

Scheme i-5

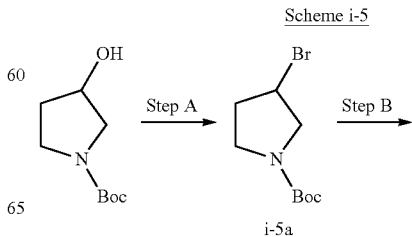

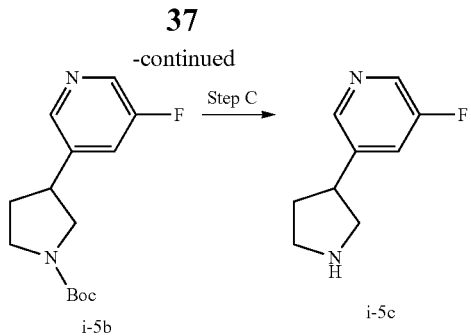

-continued i-5b → i-5c

Preparation of i-5c

Step A: Preparation of tert-butyl 3-bromopyrrolidine-1-carboxylate (i-5a)

Triphenylphosphine (727 mg, 2.77 mmol) was added to a stirred solution of tert-butyl 3-hydroxypyrrolidine-1-carboxylate (173 mg, 0.924 mmol) and carbon tetrabromide (919 mg, 2.77 mmol) in THF (3.00 mL) at 0° C., and the resulting mixture was allowed to warm slowly to rt. After 20 h, the reaction was filtered and concentrated in vacuo. Purification of the crude residue by flash chromatography on silica gel (gradient elution; 10%-40% EtOAc/hexanes as eluent) afforded the title compound i-5a m/z (ES) 250 (MH)$^+$. $^1$H NMR (500 MHz, CDCl$_3$): δ 4.49 (m, 1H), 3.81 (m, 2H), 3.63 (m, 1H), 3.53 (m, 1H), 2.33 (m, 1H), 2.26 (m, 1H), 1.49 (s, 9H).

Step B: Preparation of tert-butyl 3-(5-fluoropyridin-3-yl)pyrrolidine-1-carboxylate (i-5b)

In a glove box, a suspension of nickel iodide (37.5 mg, 0.120 mmol), trans-2-aminocyclohexanol hydrochloride (18.2 mg, 0.120 mmol), (5-fluoropyridin-3-yl)boronic acid (282 mg, 2.00 mmol) and sodium bis(trimethylsilyl)amide (367 mg, 2.00 mmol) in isopropyl alcohol (3.30 mL) was allowed to stir for 5 min. i-5a (250 mg, 0.460 mmol) was added, and the resulting mixture was heated to 80° C. for 5 h. The reaction mixture was cooled to rt, poured into satd. aq. NH$_4$Cl and extracted with EtOAc. The combined organics were washed with brine, dried (sodium sulfate) and concentrated in vacuo. Purification of the crude residue by flash chromatography on silica gel (gradient elution; 10%-80% EtOAc/hexanes as eluent) afforded the title compound i-5b. m/z (ES) 267 (MH)$^+$. $^1$H NMR (500 MHz, CDCl$_3$): δ 8.39 (d, 1H, J=2.1 Hz), 8.37 (m, 1H), 7.31 (m, 1H), 3.88 (m, 1H), 3.64 (m, 1H), 3.24-3.52 (m, 3H), 2.35 (m, 1H), 2.01 (m, 1H), 1.51 (s, 9H).

Step C: Preparation of 3-fluoro-5-pyrrolidin-3-ylpyridine (i-5c)

4.0 M HCl in dioxane (6.50 mL, 26.0 mmol) was added in two portions to a stirred solution of i-5b (268 mg, 1.01 mmol) in methanol (10.0 mL) at 0° C. After 2 h, the excess HCl was purged via a stream of N$_2$, and the resulting mixture was concentrated in vacuo to afford the title compound i-5c. m/z (ES) 167 (MH)$^+$.

Following procedures similar to those described for the preparation of intermediate i-5c, the following compounds in Table i-5 can be prepared.

TABLE i-5

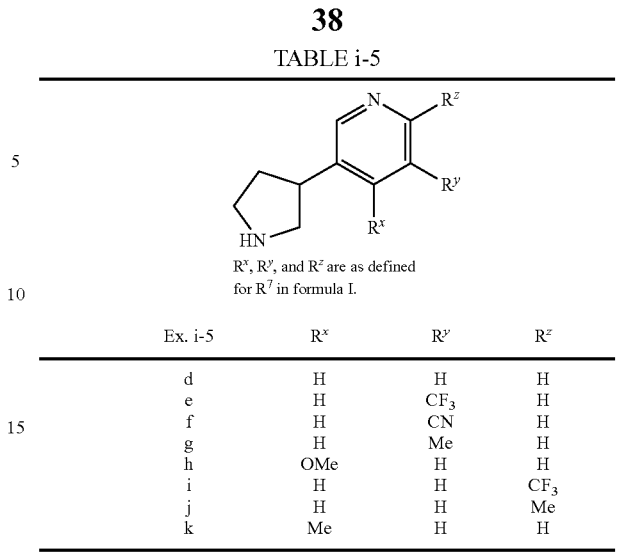

R$^x$, R$^y$, and R$^z$ are as defined for R$^7$ in formula I.

| Ex. i-5 | R$^x$ | R$^y$ | R$^z$ |
| --- | --- | --- | --- |
| d | H | H | H |
| e | H | CF$_3$ | H |
| f | H | CN | H |
| g | H | Me | H |
| h | OMe | H | H |
| i | H | H | CF$_3$ |
| j | H | H | Me |
| k | Me | H | H |

Parent Ion m/z (MH)$^+$ Data for Compounds i-5d: 149; i-5g: 163; i-5h: 179.

Scheme i-6

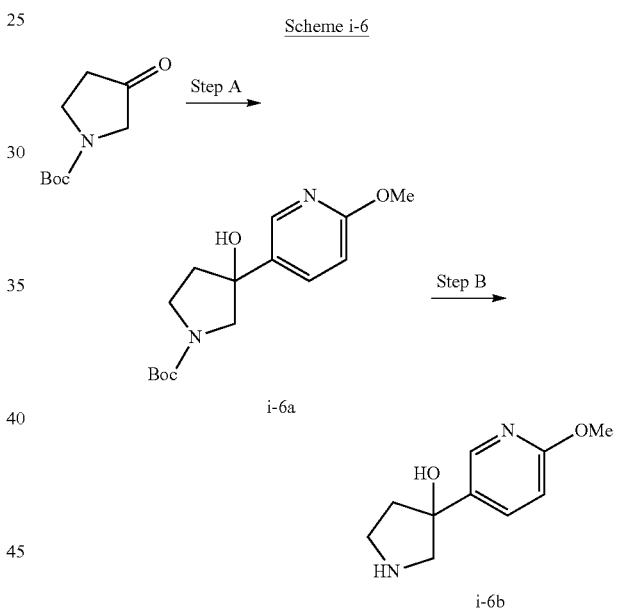

Preparation of i-6b

Step A: Preparation of tert-butyl 3-hydroxy-3-(6-methoxypyridin-3-yl)pyrrolidine-1-carboxylate (i-6a)

5-bromo-2-methoxypyridine (324 μL, 2.50 mmol) was added dropwise to a stirred suspension of n-butyllithium (1.72 mL of a 1.6 M hexanes solution, 2.75 mmol) in ether (10.0 mL) at −78° C. After 10 min, a solution of N-Boc-3-pyrrolidinone (463 mg, 2.50 mmol) in ether (2.00 mL) was added dropwise, and the reaction mixture was allowed to stir at −78° C. After 2 h, the reaction was quenched with satd. aq. NH$_4$Cl and extracted with EtOAc. The combined organics were washed with brine, dried (sodium sulfate) and concentrated in vacuo. Purification of the crude residue by flash chromatography on silica gel (gradient elution; 10%-80%

EtOAc/hexanes as eluent) afforded the title compound i-6a. m/z (ES) 295 (MH)+. ¹HNMR (500 MHz, CDCl₃): δ 831 (s, 1H), 7.71 (d, 1H, J=7.1 Hz), 6.79 (dd, 1H, J=12, 8.6 Hz), 3.97 (s, 3H), 3.40-3.80 (m, 4H), 2.25 (m, 2H), 1.51 (s, 9H).

Step B: Preparation of 3-(6-methoxypyridin-3-yl) pyrrolidin-3-ol (1-6b)

i-6b was prepared following procedures similar to those described for the preparation of i-5c, substituting i-6a for i-5b. m/z (ES) 195 (MH)+.

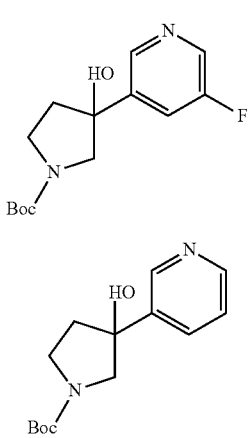

Preparation of tert-butyl 3-(5-fluoropyridin-3-yl)-3-hydroxypyrrolidine-1-carboxylate (i-6x) and tert-butyl 3-hydroxy-3-pyridin-3-ylpyrrolidine-1-carboxylate (i-6y)

i-6x and i-6y were prepared following procedures similar to those described above in step A, substituting 3-bromo-5-fluoropyridine and 3-bromopyridine, respectively, for 3-bromo-5-methoxypyridine. For i-6x: m/z (ES) 283 (MH)+. For i-6y: m/z (ES) 265 (MH)+.

Following procedures similar to those described for the preparation of intermediate i-6b, the following compounds in Table i-6 can be prepared.

TABLE i-6

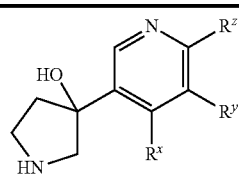

R$^x$, R$^y$, and R$^z$ are as defined for R$^7$ in formula I.

| Ex. i-6 | R$^x$ | R$^y$ | R$^z$ |
|---|---|---|---|
| c | H | H | H |
| d | H | F | H |
| e | H | Cl | H |
| f | H | Me | H |
| g | H | OMe | H |
| h | H | CF₃ | H |
| i | H | CN | H |
| j | H | H | CF₃ |
| k | H | H | Me |
| l | Me | H | H |

Parent Ion m/z (MH)+ Data for Compounds i-6c: 165; i-6d: 183; i-6e: 199; i-6f: 179; i-6g: 194; i-6h: 233; i-6l: 190.

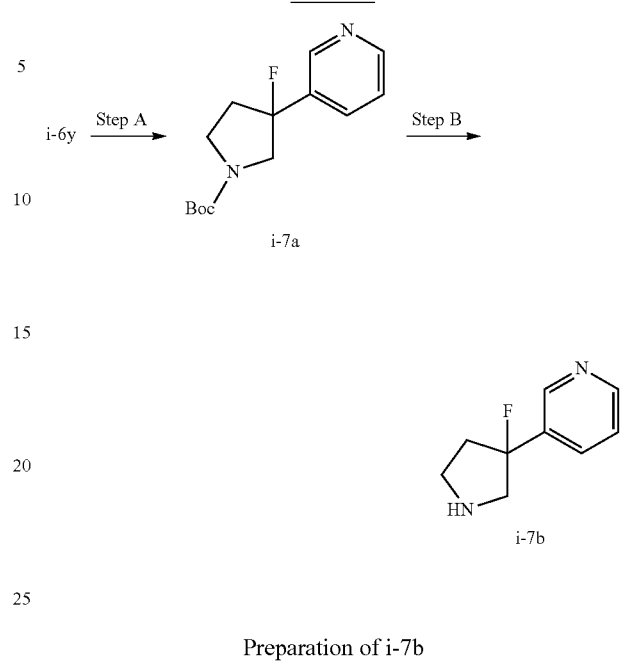

Preparation of i-7b

Step A: Preparation of tert-butyl 3-fluoro-3-(pyridin-3-yl)pyrrolidine-1-carboxylate (i-7a)

Bis(2-methoxyethyl)aminosulfur trifluoride (203 μL, 1.097 mmol) was added to a stirred solution of i-6c (290 mg, 1.097 mmol) in DCM (14.0 mL) at –78° C. After 45 min, the reaction mixture was quenched with said. aq. NaHCO₃ and extracted with DCM. The combined organics were washed with brine, dried (magnesium sulfate) and concentrated in vacuo Purification of the crude residue by flash chromatography on silica gel (gradient elution; 0%-10% methanol/DCM as eluent) afforded the title compound i-7a. m/z (ES) 267 (MH)+. ¹HNMR (500 MHz, CDCl₃): δ 8.71 (d, 1H, J=2.0 Hz), 8.63 (dd, 1H, J=1.0, 4.5 Hz), 7.77 (d, 1H, J=8.0 Hz), 7.36 (dd, 1H, J=5.0, 8.0 Hz), 3.99 (m, 1H), 3.78 (m, 1H), 3.66 (m, 2H), 2.26-2.53 (m, 2H), 1.51 (s, 9H).

Step B: Preparation of 3-(3-fluoropyrrolidin-3-yl)pyridine (i-7b)

i-7b was prepared following procedures similar to those described for the preparation of i-5c, substituting i-7a for i-5b. m/z (ES) 167 (MH)+.

Following procedures similar to those described for the preparation of intermediate i-7b, the following compounds can be prepared.

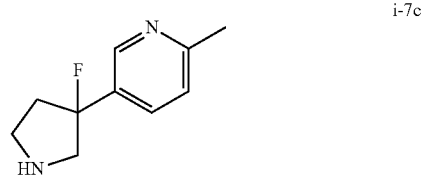

-continued

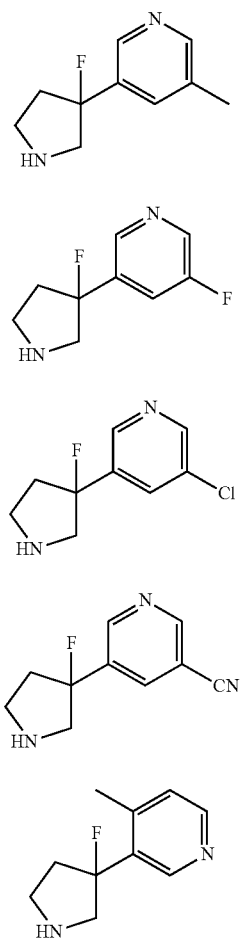

i-7d i-7e i-7f i-7g i-7h

Scheme i-8

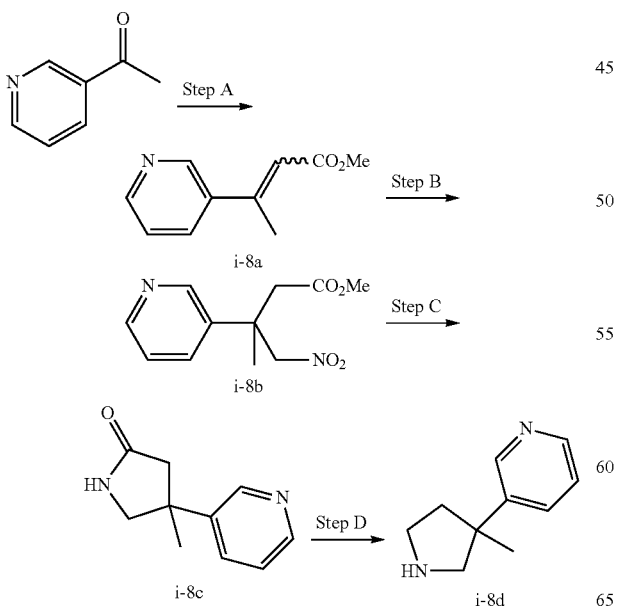

Preparation of i-8d

Step A: Preparation of methyl 3-pyridin-3-ylbut-2-enoate (i-8a)

Sodium hydride (192 mg of a 60% wt. suspension, 4.80 mmol) was added in several portions to a stirred solution of trimethylphosphonoacetate (712 μL, 4.40 mmol) in THF (20.0 mL). After 5 min, 1-pyridin-3-ylethanone (440 μL, 4.00 mmol) was added dropwise, and the resulting mixture was heated to reflux. After 20 h, the reaction mixture was cooled to rt, poured into said. aq. $NH_4Cl$ and extracted with EtOAc. The combined organics were washed with brine, dried (sodium sulfate) and concentrated in vacuo. Purification of the crude residue by flash chromatography on silica gel (gradient elution; 0%-60% EtOAc/hexanes as eluent) afforded the title compound i-8a as a separable mixture of two isomers. m/z (ES) 178 $(MH)^+$.

For i-8a (isomer A): $^1H$ NMR (500 MHz, $CDCl_3$): δ 8.74 (s, 1H), 8.61 (m, 1H), 7.77 (dd, 1H, J=1.6, 8.0 Hz), 7.33 (m, 1H), 6.17 (d, 1H, J=0.9 Hz), 3.78 (s, 3H), 2.60 (d, 3H, J=1.1 Hz).

For i-8a (isomer B): $^1H$ NMR (500 MHz, $CDCl_3$): δ 8.57 (dd, 1H, J=1.3, 4.8 Hz), 8.47 (d, 1H, J=2.3 Hz), 7.56 (m, 1H), 7.30 (dd, 1H, J=4.8, 7.8 Hz), 6.03 (s, 1H), 3.59 (s, 3H), 2.22 (d, 3H, J=0.9 Hz).

Step B: Preparation of methyl 3-methyl-4-nitro-3-pyridin-3-ylbutanoate (i-8b)

A solution of i-8a (318 mg, 1.80 mmol), nitromethane (194 μL, 3.59 mmol) and cesium carbonate (526 mg, 1.62 mmol) in DMSO (8.90 mL) was heated in a sealed tube within a microwave reactor at 140° C. for 25 min. The reaction mixture was cooled to rt, poured into satd. aq. $NH_4Cl$ and extracted with EtOAc. The combined organics were washed with brine, dried (sodium sulfate) and concentrated in vacuo. Purification of the crude residue by flash chromatography on silica gel (gradient elution; 10%-60% EtOAc/hexanes as eluent) afforded the title compound i-8b. m/z (ES) 239 $(MH)^+$. $^1H$ NMR (500 MHz, $CDCl_3$): δ 8.66 (d, 1H, J=2.5 Hz), 8.56 (dd, 1H, J=1.5, 4.7 Hz), 7.67 (m, 1H), 7.33 (dd, 1H, J=4.8, 8.2 Hz), 4.96 (m, 2H), 3.64 (s, 3H), 2.98 (m, 2H), 1.70 (s, 3H).

Step C: Preparation of 4-methyl-4-pyridin-3-ylpyrrolidin-2-one (i-8c)

i-8b (75.0 mg, 0.315 mmol) in methanol (7.50 mL) was saturated with hydrogen (1 Atm.) and passed through a column of Pd—C using an H-Cube flow apparatus (1.0 mL/min). The column was rinsed with hydrogen-saturated methanol (25 mL), and the combined organics were concentrated in vacuo. The resulting crude residue was dissolved in EtOH (3.50 mL) and heated to reflux. After 2 h, the reaction mixture was concentrated in vacuo to afford the title compound i-8c. m/z (ES) 177 $(MH)^+$.

Step D: Preparation of 3-methyl-3-pyridin-3-ylpyrrolidine (i-8d)

A solution of i-8c (55.5 mg, 0.315 mmol) and borane-THF complex (1.26 mL of a 1.0 M THF solution, 1.26 mmol) in THF (1.50 mL) was heated in a sealed tube to 60° C. After 2 h, the reaction mixture was cooled to rt, and the excess borane was quenched with 1.0 M HCl. The resulting mixture was poured into 1.0 N NaOH, saturated with solid NaCl, and extracted with EtOAc. The combined organics were dried (sodium sulfate) and concentrated in vacuo to afford the title compound i-8d. m/z (ES) 163 (MH)⁺.

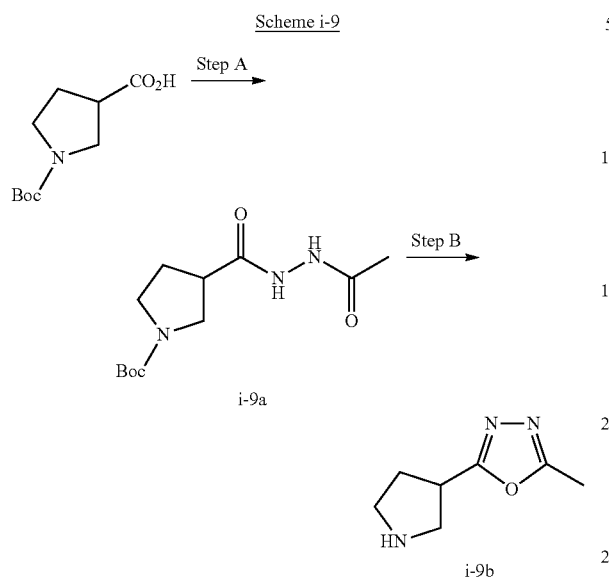

Preparation of i-9b

Step A: Preparation of tert-butyl 3-[(2-acetylhydrazino)carbonyl]pyrrolidine-1-carboxylate (i-9a)

Isobutyl chloroformate (152 µL, 1.16 mmol) was added to a stirred solution of 1-(tert-butoxycarbonyl)pyrrolidine-3-carboxylic acid (237 mg, 1.10 mmol) and 4-methylmorpholine (182 µL, 1.65 mmol) in THF (5.50 mL) at −78° C. After 15 min, added acetic hydrazide (2.0 mg, 1.10 mmol), and the resulting mixture was warmed slowly to rt. After 1 h, the reaction mixture was quenched with 0.5 M HCl and extracted with EtOAc. The combined organics were dried (sodium sulfate) and concentrated in vacuo to afford the title compound i-8a. m/z (ES) 272 (MH)⁺.

Step B: Preparation of 2-methyl-5-pyrrolidin-3-yl-1,3,4-oxadiazole (i-9b)

A solution of i-9a (299 mg, 1.10 mmol) and phosphorous oxychloride (123 µL, 1.32 mmol) in acetonitrile (5.50 mL) was heated to reflux. After 1.5 h, the reaction mixture was cooled to rt and concentrated in vacuo to afford the title compound i-9b. m/z (ES) 154 (MH)⁺.

Following procedures similar to those described for the preparation of intermediate i-9b, the following compounds can be prepared.

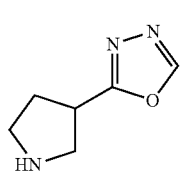
i-9d

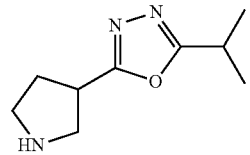
i-9e

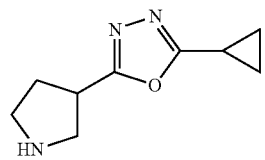
i-9f

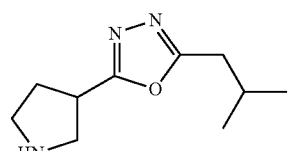
i-9g

Parent Ion m/z (MH)⁺ Data for Compounds i-9d: 140; i-9f: 180; i-9g: 196.

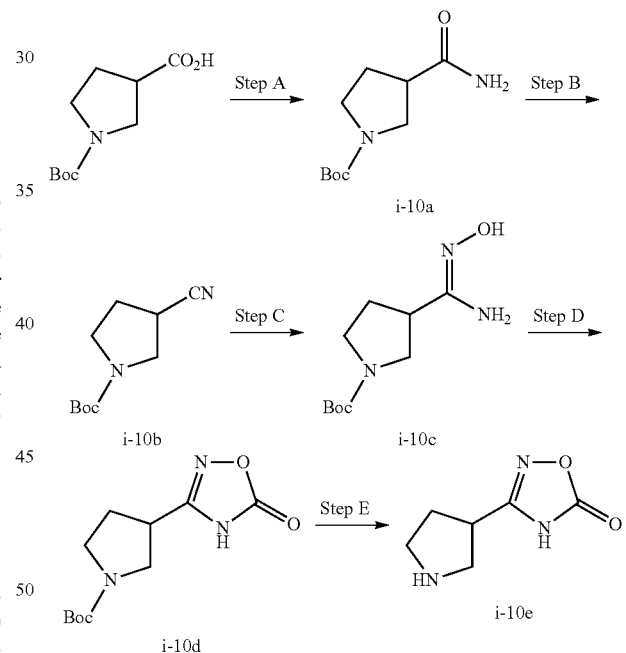

Preparation of i-10e

Step A: Preparation of tert-butyl 3-(aminocarbonyl)pyrrolidine-1-carboxylate (i-10a)

i-10a was prepared following procedures similar to those described for the preparation of i-9a, substituting methanolic ammonia for acetic hydrazide. m/z (ES) 215 (MH)⁺.

Step B: Preparation of tert-butyl 3-cyanopyrrolidine-1-carboxylate (i-10b)

Cyanuric chloride (214 mg, 1.16 mmol) was added to a stirred solution of i-10a (249 mg, 1.16 mmol) in DMF (5.80 mmol) at 0° C. After 2 h, the reaction mixture was quenched with satd. aq. NaHCO₃ and extracted with EtOAc. The combined organics were washed with 1.0 N NaOH and brine, dried (sodium sulfate) and concentrated in vacuo to afford the title compound i-10b. m/z (ES) 197 (MH)⁺. ¹H NMR (500 MHz, CDCl₃): δ 3.40-3.80 (m, 4H), 3.11 (m, 1H), 2.28 (m, 2H), 1.49 (s, 9H).

Step C: Preparation of tert-butyl 3-[(Z)-amino(hydroxyimino)methyl]pyrrolidine-1-carboxylate (i-10c)

A solution of i-10b (228 mg, 1.16 mmol) and hydroxylamine (213 μL, of a 50% w/v aq. solution, 3.48 mmol) in EtOH (5.80 mL) was heated to reflux. After 2 h, the reaction mixture was cooled to rt and concentrated in vacuo to afford the title compound i-10c. m/z (ES) 230 (MH)⁺.

Step D: Preparation of tert-butyl 3-(5-oxo-4,5-dihydro-1,2,4-oxadiazol-3-yl)pyrrolidine-1-carboxylate (i-10d)

Pyridine (29.0 μL, 0.360 mmol) was added to a stirred solution of i-10c (83.0 mg, 0.362 mmol) and triphosgene (193 mg, 0.652 mmol) in DCM (1.80 mL) at −78° C., and the resulting mixture was allowed to warm to rt. After 12 h, the reaction mixture was quenched with satd. aq. NH₄Cl and extracted with EtOAc. The combined organics were washed with brine, dried (sodium sulfate) and concentrated in vacuo. Purification of the crude residue by flash chromatography on silica gel (gradient elution; 0%-25% EtOAc/hexanes as eluent) afforded the title compound i-10d. m/z (ES) 256 (MH)⁺.

Step E: Preparation of 3-pyrrolidin-3-yl-1,2,4-oxadiazol-5(4H)-one (i-10e)

i-10e was prepared following procedures similar to those described for the preparation of i-5c, substituting i-10d for i-5b. m/z (ES) 156 (MH)⁺.

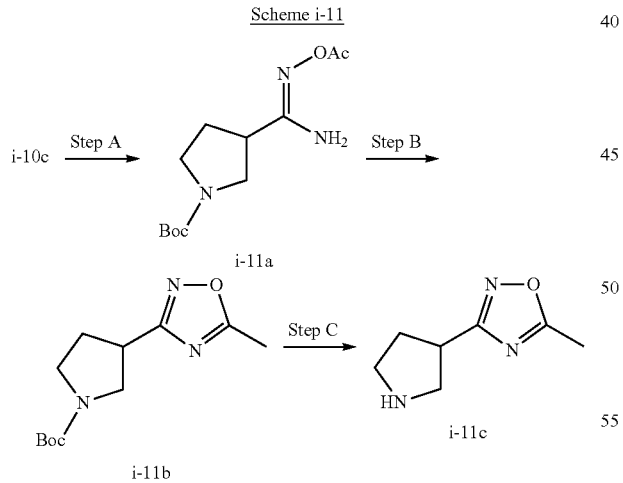

Scheme i-11

Preparation of i-11c

Step A: Preparation of tert-butyl 3-[[(acetyloxy)imino](amino)methyl]pyrrolidine-1-carboxylate (i-11a)

Acetic anhydride (36.2 μL, 0.384 mmol) was added to a stirred solution of i-10c (80.0 mg, 0.349 mmol) and triethylamine (68.0 μL, 0.488 mmol) in DCM (1.75 mL) at rt. After 1 h, the reaction mixture was quenched with satd. aq. NH₄Cl and extracted with EtOAc. The combined organics were washed with satd. aq. NaHCO₃ and brine, dried (sodium sulfate) and concentrated in vacuo to afford the title compound i-11a. m/z (ES) 272 (MH)⁺.

Step B: Preparation of tert-butyl 3-(5-methyl-1,2,4-oxadiazol-3-yl)pyrrolidine-1-carboxylate (i-11b)

A stirred solution of i-11a (95.0 mg, 0.349 mmol) in xylenes (3.50 mL) was heated to 120° C. After 12 h, the reaction mixture was concentrated in vacuo to afford the title compound i-11b. m/z (ES) 254 (MH)⁺.

Step C: Preparation of 5-methyl-3-pyrrolidin-3-yl-1,2,4-oxadiazole (i-11c)

i-11c was prepared following procedures similar to those described for the preparation of i-5c, substituting i-11b for i-5b. m/z (ES) 154 (MH)⁺.

Following procedures similar to those described for the preparation of intermediate i-11c, the following compounds can be prepared.

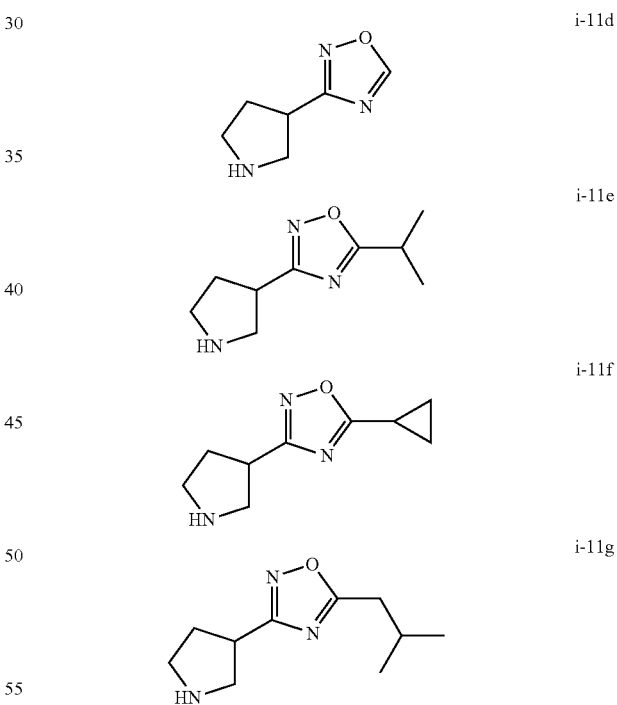

Scheme i-12

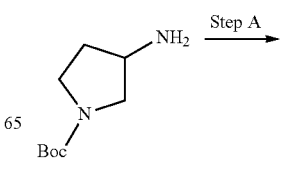

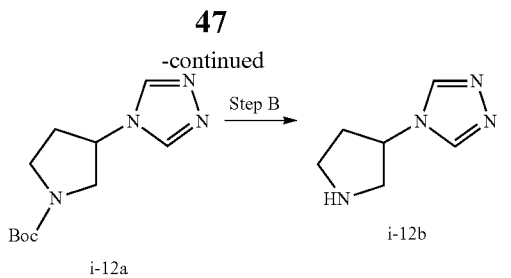

Preparation of i-12b

Step A: Preparation of tert-butyl 3-(4H-1,2,4-triazol-4-yl)pyrrolidine-1-carboxylate (i-12a)

A stirred solution of tert-butyl 3-aminopyrrolidine-1-carboxylate (848 µL, 5.00 mmol), i-12c (711 mg, 5.00 mmol) and pTSA (95.0 mg, 0.500 mmol) in toluene was heated to 95° C. After 10 h, the reaction mixture was cooled to rt, poured into satd. aq. NaHCO$_3$ and extracted with EtOAc. The combined organics were washed with brine, dried (sodium sulfate) and concentrated in vacuo to afford the title compound i-12a. m/z (ES) 239 (MH)$^+$. $^1$H NMR (500 MHz, CDCl$_3$): δ 8.23 (s, 2H), 4.84 (m, 1H), 3.50-3.70 (m, 4H), 2.50 (m, 1H), 2.22 (m, 1H), 1.51 (s, 9H).

Step B: Preparation of 4-pyrrolidin-3-yl-4H-1,2,4-triazole (i-12b)

i-12b was prepared following procedures similar to those described for the preparation of i-5c, substituting i-12a for i-5b. m/z (ES) 139 (MH)$^+$.

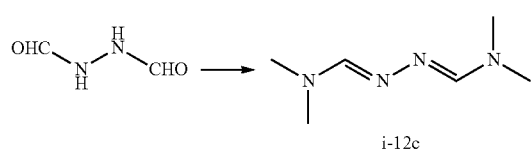

Preparation of N'-[(1E)-(dimethylamino)methylene]-N,N-dimethylhydrazonoformamide (i-12c)

Thionyl chloride (41.4 mL, 568 mmol) was added to a stirred solution of N'-formylformic hydrazide (20.0 g, 227 mmol) in DMF (227 mL) at 0° C., and the resulting mixture was allowed to warm to rt. After 72 h, the reaction mixture was diluted with water, quenched with solid sodium carbonate and extracted with DCM. The combined organics were dried (sodium sulfate) and concentrated in vacuo to afford the title compound i-12c. $^1$H NMR (500 MHz, CDCl$_3$): δ 7.77 (s, 2H), 2.93 (s, 6H).

Scheme i-13

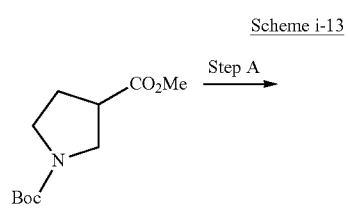

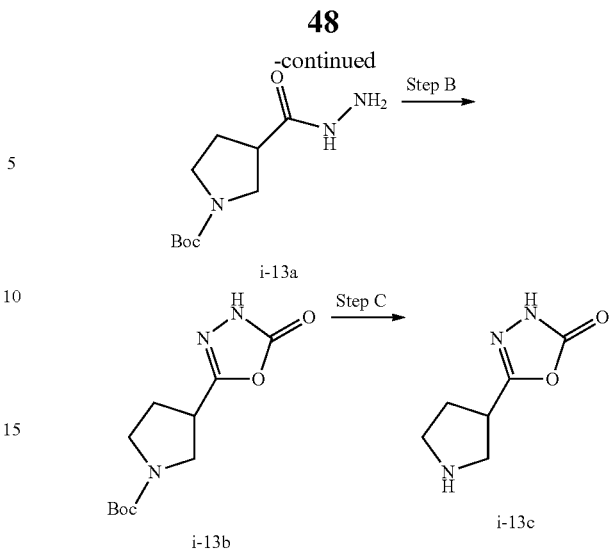

Preparation of i-13c

Step A: Preparation of tert-butyl 3-(hydrazinocarbonyl)pyrrolidine-1-carboxylate (i-13a)

A solution of 1-tert-butyl 3-methylpyrrolidine-1,3-dicarboxylate (1.00 equiv.) and hydrazine (excess of 50% aq. solution) in ethanol (0.2 M final conc.) is heated to reflux. After the reaction is deemed complete, the reaction mixture is cooled to rt and partially concentrated. The resulting mixture is diluted with EtOAc, and the resulting organics are washed with water and brine, dried (sodium sulfate) and concentrated in vacuo to afford the title compound i-13a.

Step B: Preparation of tert-butyl 3-(5-oxo-4,5-dihydro-1,3,4-oxadiazol-2-yl)pyrrolidine-1-carboxylate (i-13b)

Phosgene (1.50 equiv. of a 20% toluene solution) is added to a solution of i-13a (1.00 equiv.) and pyridine (4.00 equiv.) in DCM (0.1 M final conc.) at −78° C. After the reaction is deemed complete, the reaction mixture is quenched with said. aq. NaHCO$_3$ and extracted with EtOAc. The combined organics are washed with brine, dried (sodium sulfate) and concentrated in vacuo to afford the title compound i-13b.

Step C: Preparation of 5-pyrrolidin-3-yl-1,3,4-oxadiazol-2(3H)-one (i-13c)

i-13c can be prepared following procedures similar to those described for the preparation of i-5c, substituting i-13b for i-5b.

Scheme i-14

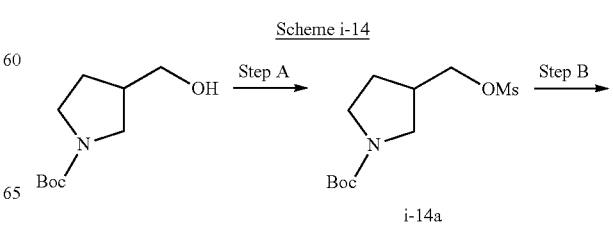

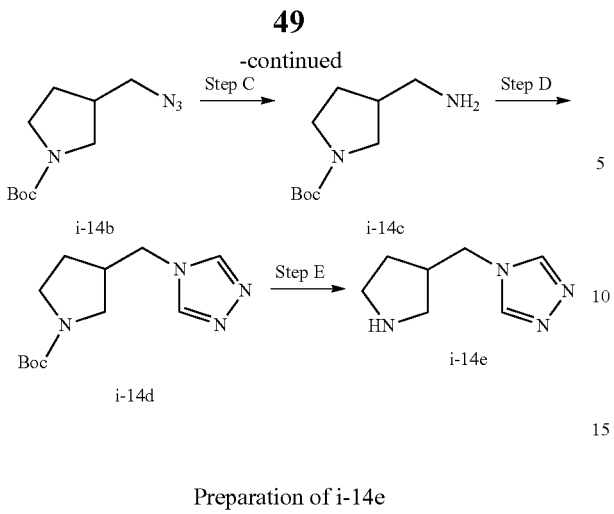

Preparation of i-14e

Step A: Preparation of tert-butyl 3-{[(methylsulfonyl)oxy]methyl}pyrrolidine-1-carboxylate (i-14a)

Mesyl chloride (106 μL, 1.37 mmol) was added to a stirred solution of tert-butyl 3-(hydroxymethyl)pyrrolidine-1-carboxylate (250 mg, 1.242 mmol) and triethylamine (225 μL, 1.62 mmol) in DCM at 0° C. After 20 min, the reaction mixture was diluted with DCM, washed with brine, dried (sodium sulfate) and concentrated in vacuo to afford the title compound i-14a. $^1$H NMR (500 MHz, CDCl$_3$): δ 4.19 (m, 2H), 3.20-3.60 (m, 3H), 3.17 (m, 1H), 3.05 (s, 3H), 2.65 (m, 1H), 2.07 (m, 1H), 1.74 (m, 1H), 1.48 (s, 9H).

Step B: Preparation of tert-butyl 3-(azidomethyl)pyrrolidine-1-carboxylate (i-14b)

A stirred suspension of i-14a (347 mg, 1.24 mmol) and sodium azide (322 mg, 4.97 mmol) in DMSO (6.00 mL) was heated to 50° C. overnight. The reaction mixture was cooled to rt, poured into water and extracted with EtOAc. The combined organics were washed with brine, dried (sodium sulfate) and concentrated in vacuo to afford the title compound i-14b. $^1$H NMR (500 MHz, CDCl$_3$): δ 3.30-3.65 (m, 6H), 3.08 (m, 1H), 2.45 (m, 1H), 2.04 (m, 1H), 1.65 (m, 1H), 1.49 (s, 9H).

Step C: Preparation of tert-butyl 3-(aminomethyl)pyrrolidine-1-carboxylate (i-14c)

A stirred suspension of i-14b (105 mg, 0.464 mmol) and 10 wt. % palladium on carbon (49.0 mg, 0.046 mmol) in methanol (4.50 mL) was stirred under hydrogen (1 Atm.) at rt for 1 h. The reaction mixture was diluted with EtOAc and filtered through a short column of Celite®. The Celite® column was rinsed with additional portions of EtOAc, and the combined organic fractions were dried (sodium sulfate) and concentrated in vacuo to afford the title compound i-14c. m/z (ES) 201 (MH)$^+$.

Step D: Preparation of tert-butyl 3-(4H-1,2,4-triazol-4-ylmethyl)pyrrolidine-1-carboxylate (i-14d)

i-14d was prepared following procedures similar to those described for the preparation of i-12a, substituting i-14c for tert-butyl 3-aminopyrrolidine-1-carboxylate. m/z (ES) 253 (MH)$^+$.

Step E: Preparation of 4-(pyrrolidin-3-ylmethyl)-4H-1,2,4-triazole (i-14e)

i-14e was prepared following procedures similar to those described for the preparation of i-5c, substituting i-14d for i-5b. m/z (ES) 153 (MH)$^+$.

Scheme i-15

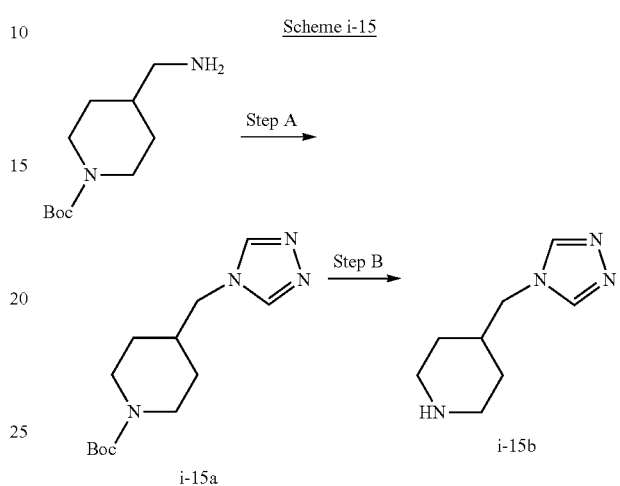

Preparation of 4-(4H-1,2,4-triazol-4-ylmethyl)piperidine (i-15b)

i-15b was prepared from tert-butyl 4-(aminomethyl)piperidine-1-carboxylate in two steps by following procedures, described for the preparation of 1-12a, substituting tert-butyl 4-(aminomethyl)piperidine-1-carboxylate for tert-butyl 3-aminopyrrolidine-1-carboxylate in Step A. The product of this reaction, i-15a was subjected to conditions described for the preparation of i-5c, substituting i-15a for i-5b. m/z (ES) 167 (MH)$^+$.

Scheme i-16

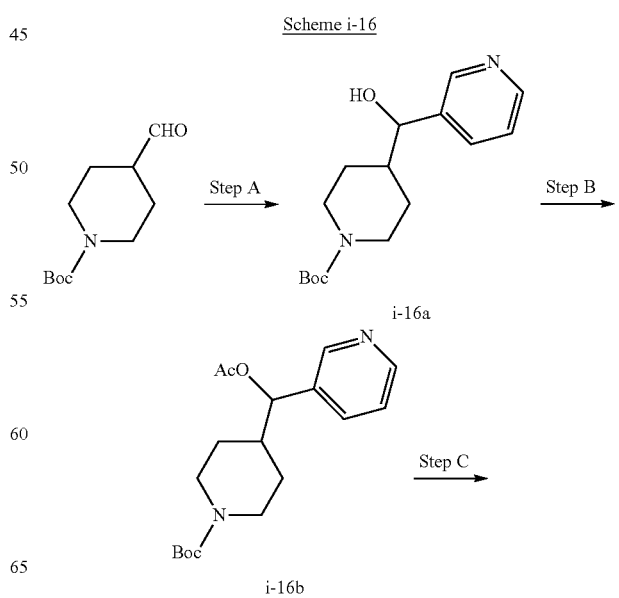

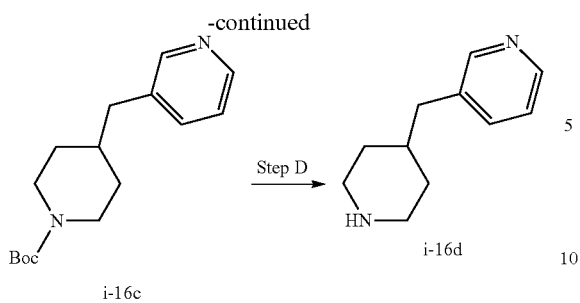

Following procedures similar to those described above for preparing intermediate i-16d, the following additional intermediates can be prepared.

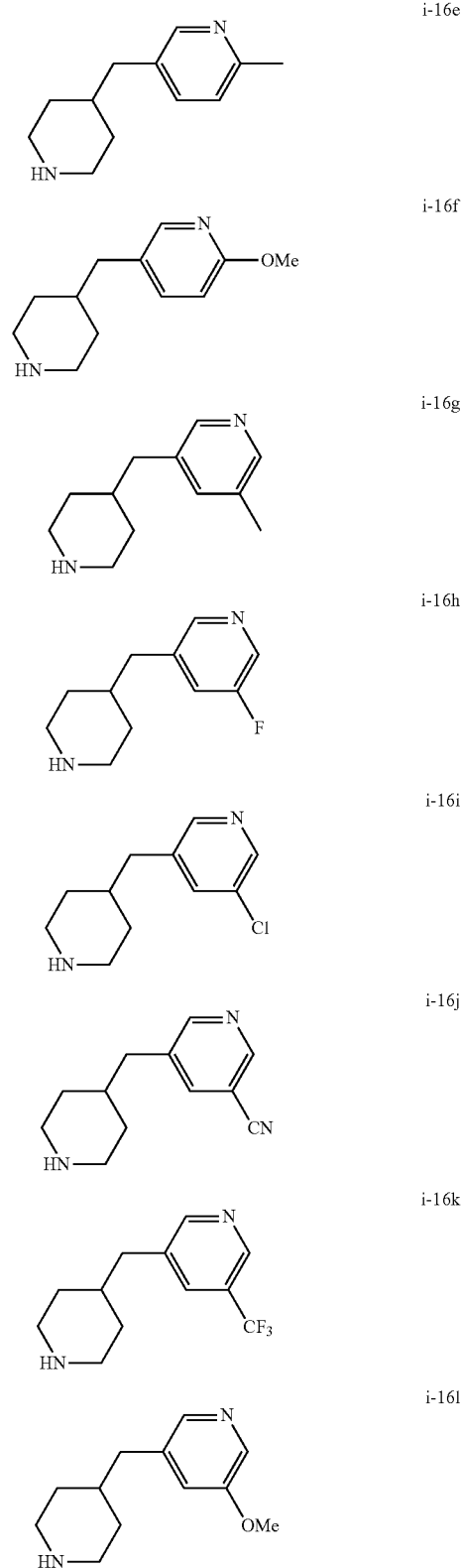

Preparation of i-16d

Step A: Preparation of tert-butyl 4-[hydroxy(pyridin-3-yl)methyl]piperidine-1-carboxylate (i-16a)

3-Bromopyridine (116 μL, 1.20 mmol) was added slowly dropwise to a stirred suspension of n-butyllithium (480 μL of a 2.5 M hexanes solution, 1.20 mmol) in THF (1.00 mL) at −78° C. After 15 min, tert-butyl 4-formylpiperidine-1-carboxylate (213 mg, 1.00 mmol) was added, and the resulting mixture was allowed to stir at −78° C. After 1 h, the reaction was quenched with 1.0 M HCl, poured into satd. aq. NaHCO$_3$ and extracted with EtOAc. The combined organics were washed with brine, dried (sodium sulfate) and concentrated in vacuo. Purification of the crude residue by flash chromatography on silica gel (gradient elution; 10%-100% EtOAc/DCM as eluent) afforded the title compound i-16a. $^1$H NMR (500 MHz, CDCl$_3$): δ 8.55 (m, 2H), 7.70 (d, 1H, J=8.0 Hz), 7.32 (dd, 1H, J=4.9, 7.4 Hz), 4.49 (m, 1H), 4.15 (m, 4H), 2.65 (m, 2H), 1.83 (m, 1H), 1.79 (m, 1H), 1.46 (s, 9H), 1.31 (m, 1H).

Step B: Preparation of tert-butyl 4-[(acetyloxy)(pyridin-3-yl)methyl]piperidine-1-carboxylate (i-16b)

Acetic anhydride (204 μL, 2.16 mmol) was added to a stirred solution of i-16a (158 mg, 0.540 mmol) and triethylamine (377 μL, 2.70 mmol) in DCE (2.70 mL). After 6 h, the reaction mixture was quenched with 0.5 M HCl and extracted with DCM. The combined organics were washed with satd. aq. NaHCO$_3$ and brine, dried (sodium sulfate) and concentrated in vacuo to afford the title compound i-16b. m/z (ES) 335 (MH)$^+$.

Step C: Preparation of tert-butyl 4-[(pyridin-3-yl)methyl]piperidine-1-carboxylate (i-16c)

A stirred suspension of i-16b (181 mg, 0.540 mmol), ammonium formate (141 μL, 2.87 mmol) and 10 wt. % palladium on carbon (57.0 mg, 0.054 mmol) in methanol (5.50 mL) was stirred at rt for 12 h. The reaction mixture was diluted with methanol and filtered through a short column of Celite®. The Celite® column was rinsed with additional portions of methanol, and the combined organic fractions were concentrated in vacuo to afford the title compound i-16c. m/z (ES) 277 (MH)$^+$.

Step D: Preparation of 3-(piperidin-4-ylmethyl)pyridine (i-16d)

i-16d was prepared following procedures similar to those described for the preparation of i-5c, substituting i-16c for i-5b. m/z (ES) 177 (MH)$^+$.

Scheme i-17

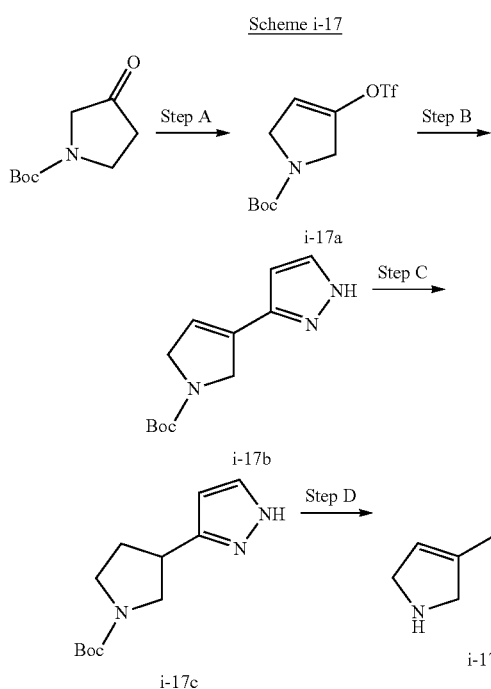

Preparation of i-17d

Step A: Preparation of tert-butyl 3-{[(trifluoromethyl)sulfonyl]oxy}-2,5-dihydro-1H-pyrrole-1-carboxylate (i-17a)

Lithium hexamethyldisilazane (5.50 mL of a 1.0 M ether solution, 5.50 mmol) was added to a solution of tert-butyl 3-oxopyrrolidine-1-carboxylate (925 mg, 5.00 mmol) in THF (15.0 mL) at −78° C. After 1 h and then a solution of 2-[N,N-bis(trifluoromethylsulfonyl)amino]-5-chloropyridine (2.16 g, 5.50 mmol) in THF (10.0 mL) was added dropwise, and the resulting mixture was allowed to stir at −78° C. After 2 h, the reaction mixture was quenched with satd. aq. NH$_4$Cl and extracted with EtOAc. The combined organics were washed with water and brine, dried (sodium sulfate), and concentrated in vacuo. Purification of the crude residue by flash chromatography on silica gel (gradient elution; 1%-2% EtOAc/petroleum ether as eluent) afforded the title compound i-17a.

Step B: Preparation of tert-butyl 3-(1H-pyrazol-3-yl)-2,5-dihydro-1H-pyrrole-1-carboxylate (i-17b)

A mixture of i-17a (317 mg, 1.00 mmol), 3-pyrazole boronic acid (123 mg, 1.10 mmol), [1,1'-bis(diphenylphosphino)ferrocene]dichloropalladium (II)-DCM complex (25.0 mg, 0.031 mmol) and sodium carbonate (2.00 mL of a 2.0 M aq. solution, 2.00 mmol) in dioxane (6.00 mL) was heated to 90° C. After 4 h, the reaction mixture was cooled to rt and filtered through a short column of Celite®. The Celite® column was rinsed with EtOAc, and the combined organics were washed with water and brine, dried (sodium sulfate) and concentrated in vacuo. Purification of the crude residue by flash chromatography on silica gel (gradient elution; 0%-23% EtOAc/hexanes as eluent) afforded the title compound i-17b. m/z (ES) 236 (MH)$^+$.

Step C: Preparation of tert-butyl 3-(1H-pyrazol-3-yl)-pyrrolidine-1-carboxylate (i-17c)

A stirred suspension of i-17b (165 mg, 0.700 mmol) and 10 wt. % palladium on carbon (20.0 mg, 0.022 mmol) in methanol (20.0 mL) was stirred under hydrogen (1 Atm.) at rt. After 1.5 h, the reaction mixture was diluted with methanol and filtered through a short column of Celite®. The Celite® column was rinsed with additional portions of methanol, and the combined organic fractions were concentrated in vacuo to afford the title compound i-17c. m/z (ES) 239 (MH)$^+$.

Step D: Preparation of 3-(1H-Pyrazol-3-yl)-pyrrolidine (i-17d)

i-17d was prepared following procedures similar to those described for the preparation of i-5c, substituting i-17c for i-5b. m/z (ES) 139 (MH)$^+$.

Scheme i-18

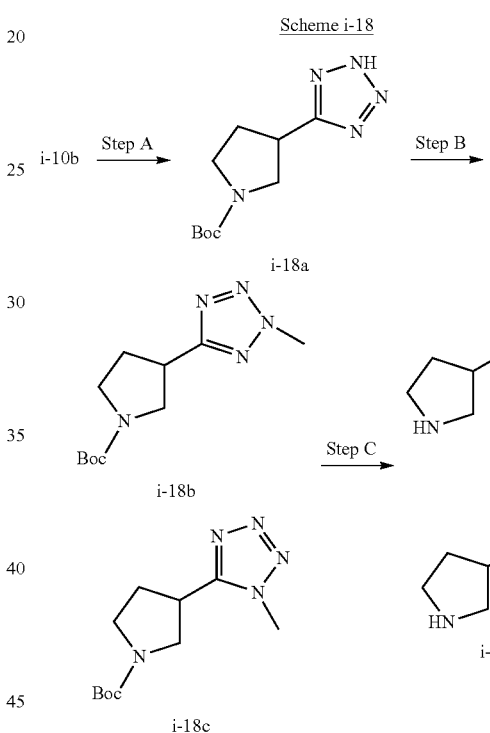

Preparation of i-18d and i-18e

Step A: Preparation of tert-butyl 3-(2H-tetrazol-5-yl)pyrrolidine-1-carboxylate (i-18a)

A mixture of i-10b (200 mg, 1.00 mmol), sodium azide (195 mg, 3.00 mmol) and ammonium chloride (109 mg, 3.00 mmol) in DMF (3.00 mL) was heated to 120° C. After 18 h, the reaction mixture was cooled to rt, and 1.0 M HCl was added to the stirring mixture. After an additional 30 min, the reaction mixture was diluted with water and extracted with DCM. The combined organics were washed with brine, dried (sodium sulfate) and concentrated in vacuo to afford the title compound i-18a. m/z (ES) 186 (MH)$^+$.

Step B: Preparation of tert-butyl 3-(2-methyl-2H-tetrazol-5-yl)pyrrolidine-1-carboxylate (i-18b)

Iodomethane (0.600 mmol) was added to a stirred solution of i-18a (0.500 mmol) and potassium carbonate (0.700 mmol)

in acetonitrile (5.00 mL), and the resulting mixture was heated to reflux. After 3 h, the reaction mixture was cooled to rt, filtered and concentrated in vacuo. The crude residue was dissolved in DCM, and the organics were washed with water and brine, dried (sodium sulfate) and concentrated in vacuo to afford the title compound, i-18b, and regioisomer, i-18c. m/z (ES) 254 (MH)$^+$.

Step C: Preparation of 2-methyl-5-pyrrolidin-3-yl-2H-tetrazole (i-18d)

i-18d and i-18e were prepared following procedures similar to those described for the preparation of i-5c, substituting i-18b and i-18c, respectively, for i-5b. m/z (ES) 154 (M1-1)$^+$.

Following procedures similar to those described above for preparing intermediates i-18d and i-18e, the following additional intermediates can be prepared from i-18a.

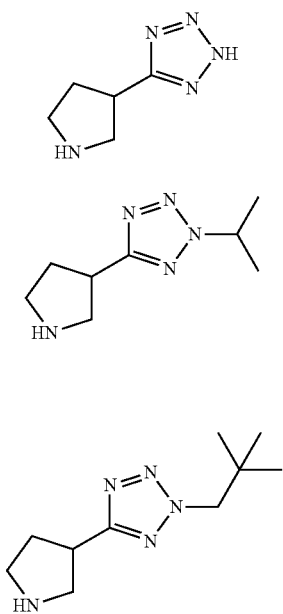

i-18f i-18g i-18i

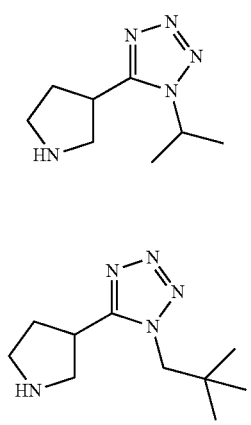

i-18h i-18j

Parent Ion m/z (MH)$^+$ Data for Compounds i-18f: 140; i-18g: 182; i-18i: 210.

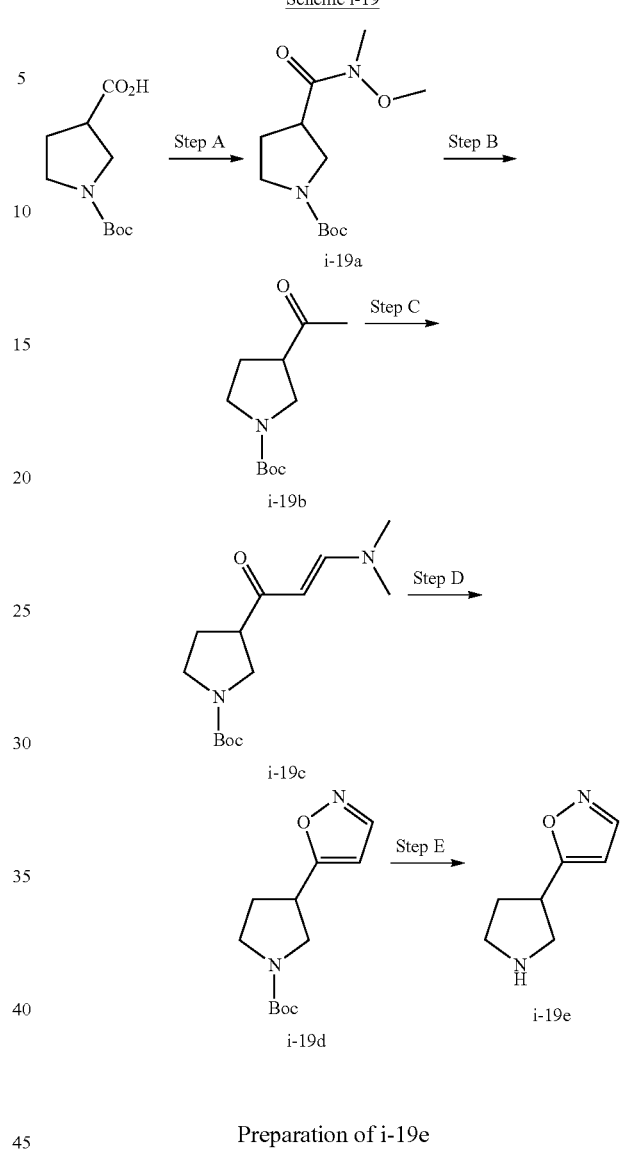

Scheme i-19

Preparation of i-19e

Step A: Preparation of tert-butyl 3-{[methoxy(methyl)amino]carbonyl}pyrrolidine-1-carboxylate (i-19a)

HATU (4.56 g, 12.0 mmol) was added to 1-(tert-butoxycarbonyl)pyrrolidine-3-carboxylic acid (2.15 g, 10.0 mmol), N,O-dimethylhydroxylamine hydrochloride (1.17 g, 12.0 mmol), and triethylamine (30.0 mmol) in DCM (50.0 mL), and the resulting mixture was allowed to stir at rt. After 12 h, the reaction mixture was diluted with DCM, and the combined organics were washed with water and brine, dried (sodium sulfate) and concentrated in vacuo to afford the title compound i-19a. m/z (ES) 259 (MH)$^+$.

Step B: Preparation of tert-butyl 3-acetylpyrrolidine-1-carboxylate (i-19b)

Methyl magnesium bromide (750 µL, of a 3.0 M ether solution, 2.25 mmol) was added to a stirred solution of i-19a (258 mg, 1.00 mmol) in THF (2.50 mL) at −78° C., and after 1 h, the reaction mixture was warmed slowly to 0° C. After 3 h, the reaction mixture was quenched with satd. aq. NH₄Cl, and the resulting mixture was extracted with EtOAc. The combined organics were washed with water and brine, dried (sodium sulfate) and concentrated in vacuo. Purification of the crude residue by flash chromatography on silica gel (gradient elution; 10%-20% EtOAc/petroleum ether as eluent) afforded the title compound i-19b. m/z (ES) 214 (MH)⁺.

Step C: Preparation of tert-butyl 3-[(2E)-3-(dimethylamino)prop-2-enoyl]pyrrolidine-1-carboxylate (i-19c)

A stirred solution of i-19b (213 mg, 1.00 mmol) and N,N,-dimethylformamide dimethylacetal (260 mg, 2.00 mmol) was heated to 85° C. After 8 h, the reaction mixture was cooled to rt and concentrated in vacuo to afford the title compound i-19c.

Step D: Preparation of tert-butyl 3-isoxazol-5-ylpyrrolidine-1-carboxylate (i-19d)

A stirred solution of i-19c (80.0 mg, 0.310 mmol) and hydroxylamine hydrochloride (22.9 mg, 0.330 mmol) in methanol (3.00 mL) was heated to reflux. After 7 h, the reaction mixture was cooled to rt, poured into water and extracted with EtOAc. The combined organics were washed with brine, dried (sodium sulfate) and concentrated in vacuo. Purification of the crude residue by preparative thin-layer chromatography on silica gel (50% EtOAc/petroleum ether as eluent) afforded the title compound i-19c. m/z (ES) 239 (MH)⁺.

Step E: Preparation of 3-isoxazol-5-ylpyrrolidine (i-19e)

i-19e was prepared following procedures similar to those described for the preparation of i-5c, substituting i-19d for i-5b. m/z (ES) 139 (MH)⁺.

Scheme i-20

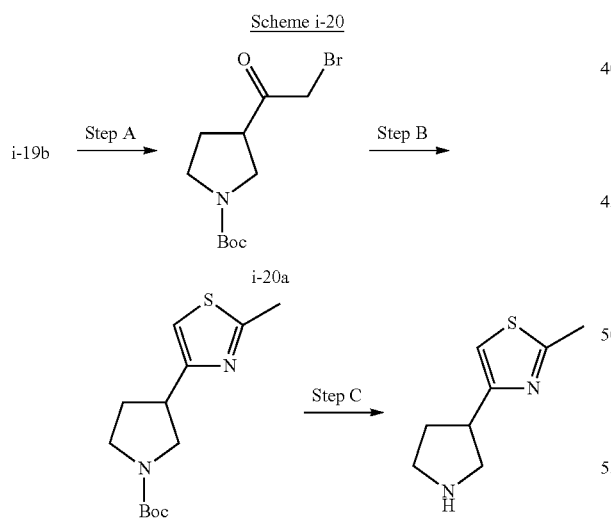

Preparation of i-20c

Step A: Preparation of tert-butyl 3-(bromoacetyl)pyrrolidine-1-carboxylate (i-20a)

Chlorotrimethylsilane (1.13 mL, 10.6 mmol) was added dropwise to a stirred solution of lithium hexamethyldisilylamide (1.20 ml of a 1.0 M THF solution, 1.20 mmol) in THF (40.0 mL) at −78° C. After 5 min, a solution of i-19b (213 mg, 1.00 mmol) in THF (4.00 mL) was added dropwise, and the resulting mixture was warmed to 0° C. over 30 min, at which point N-bromosuccinimide (210 mg, 1.21 mmol) was added. After 30 min, the reaction mixture was concentrated in vacuo, and the residue was dissolved in EtOAc. The organics were washed with water and brine, dried (magnesium sulfate) and concentrated in vacuo. Purification of the crude residue by preparative thin-layer chromatography on silica gel (30% EtOAc/petroleum ether as eluent) afforded the title compound i-20a. ¹H NMR (400 MHz, CDCl₃): δ 4.12 (s, 1H), 3.98 (s, 1H), 3.65-3.39 (m, 4H), 2.23-2.10 (m, 2H), 1.48 (s, 9H).

Step B: Preparation of tert-butyl 3-(2-methyl-1,3-thiazol-4-yl)pyrrolidine-1-carboxylate (i-20b)

A mixture of i-20a (60.0 mg, 0.210 mmol), thioacetamide (31.5 mg, 0.420 mmol) and sodium bicarbonate (35.8 mg, 0.420 mmol) in ethanol (1.00 mL) were heated in a sealed tube within a microwave reactor at 120° C. for 15 min. The reaction mixture was cooled to rt, concentrated in vacuo, and the resulting residue was partitioned between EtOAc and water. The layers were separated, and the organics were washed with satd. aq. NaHCO₃ and brine, dried (sodium sulfate) and concentrated in vacuo. Purification of the crude residue by preparative thin-layer chromatography on silica gel (50% EtOAc/petroleum ether as eluent) afforded the title compound i-20b.

Step C: Preparation of 2-methyl-4-pyrrolidin-3-yl-1,3-thiazole (i-20c)

i-20c was prepared following procedures similar to those described for the preparation of i-5c, substituting i-20b, for i-5b. m/z (ES) 169 (MH)⁺.

Scheme i-21

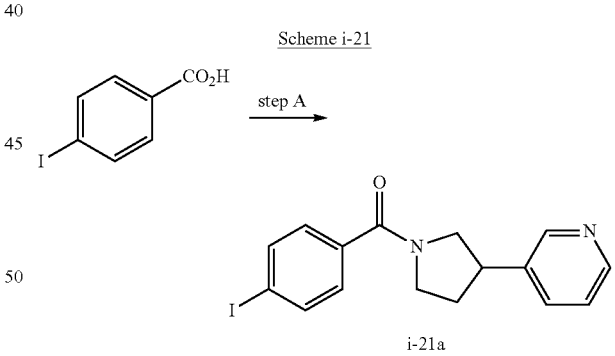

Preparation of i-21a

Step A: Preparation of 3-[1-(4-iodobenzoyl)pyrrolidin-3-yl]pyridine (i-21a)

i-5d (3.59 g, 24.2 mmol) was added to a stirred solution of 4-iodobenzoic acid (6.00 g, 24.2 mmol), N-(3-dimethylaminopropyl)-N'-ethylcarbodiimide hydrochloride (5.10 g, 26.6 mmol) and 1-hydroxybenzotriazole (3.70 g, 24.2 mmol) in DMF (100 mL). After 12 h, the reaction mixture was quenched with said, aq. NaHCO₃ and extracted with EtOAc. The organic layer was washed with water and brine, dried (sodium sulfate) and concentrated in vacuo to afford the title compound i-21a. m/z (ES) 379 (MH)+.
Following procedures similar to those described above for preparing intermediate i-21a, the following additional intermediates can be prepared.
TABLE i-21a
| Ex. i-21A | Ex. i-21B | Ex. i-21C | Ex. i-21D | R¹ |
|---|---|---|---|---|
| — | a | a | a | 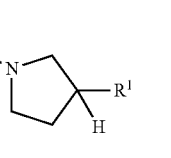 |
| b | b | b | b | 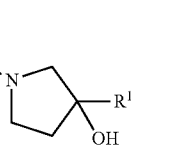 |
| c | c | c | c | 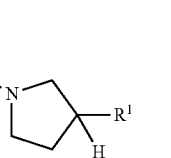 |
| d | d | d | d | 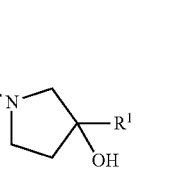 |
| e | e | e | e | 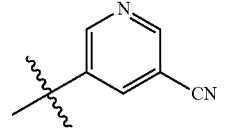 [SMILES: *c1cncc(C#N)c1] |
| f | f | f | f | 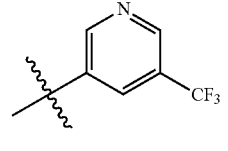 [SMILES: *c1cncc(C(F)(F)F)c1] |
| g | g | g | g | 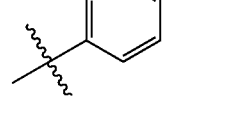 |
| h | h | h | h | 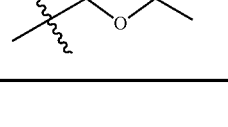 |
| i | i | i | i | 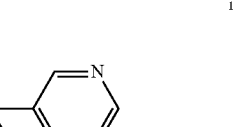 |
TABLE i-21b
| Ex. i-21E | Ex. i-21F | R |
|---|---|---|
| a | a | 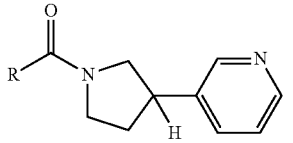 |
| b | b | 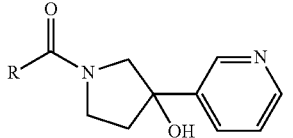 |

TABLE i-21b-continued

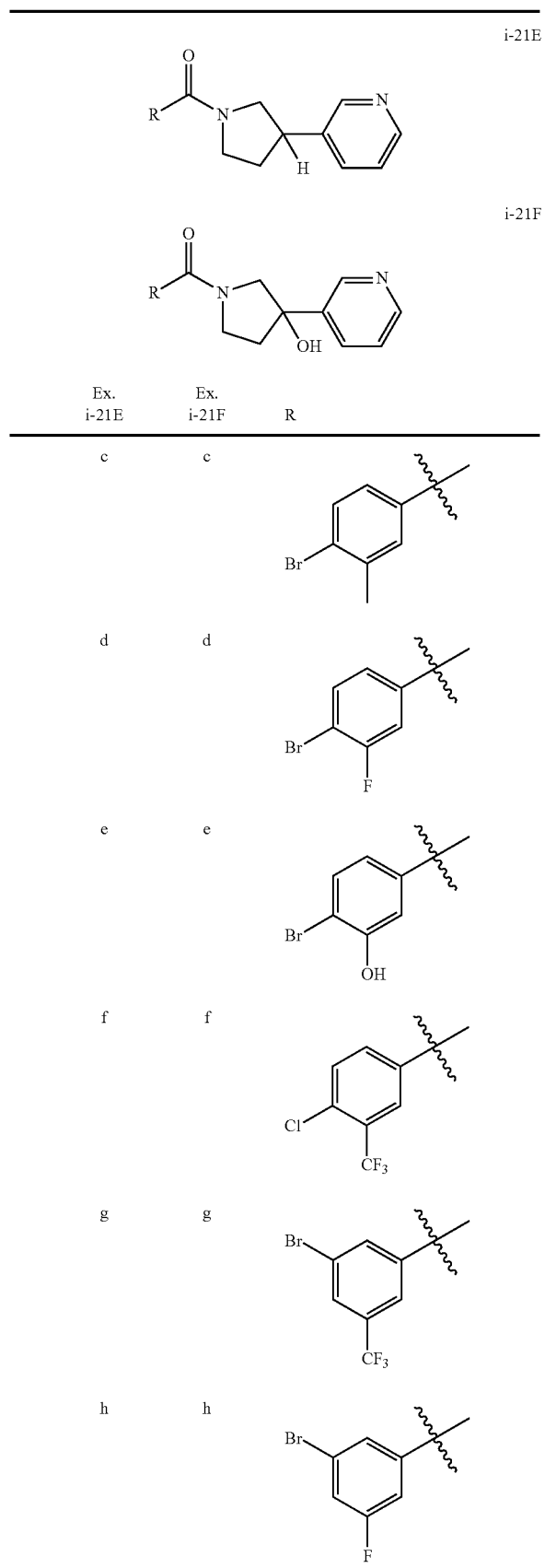

| Ex. i-21E | Ex. i-21F | R |
|---|---|---|
| c | c | (4-Br, 3-Me phenyl) |
| d | d | (4-Br, 3-F phenyl) |
| e | e | (4-Br, 3-OH phenyl) |
| f | f | (4-Cl, 3-CF₃ phenyl) |
| g | g | (3-Br, 5-CF₃ phenyl) |
| h | h | (3-Br, 5-F phenyl) |

TABLE i-21b-continued

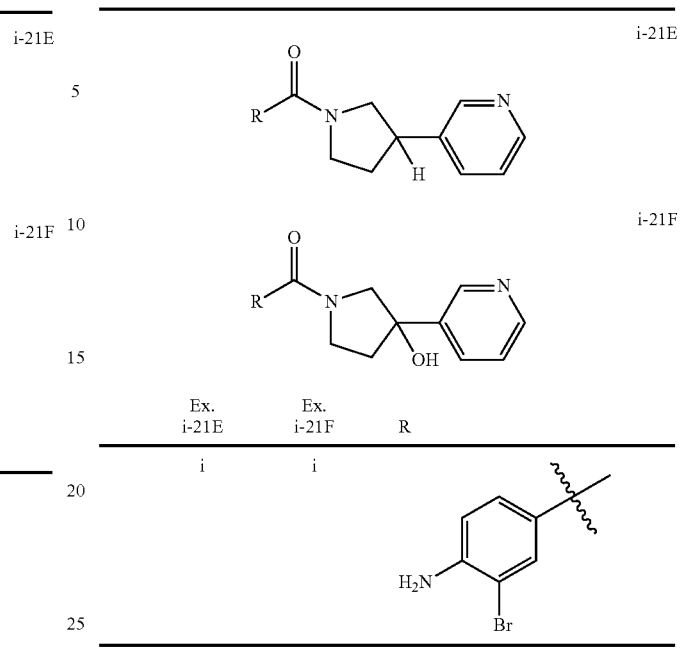

| Ex. i-21E | Ex. i-21F | R |
|---|---|---|
| i | i | (2-Br, 4-NH₂ phenyl) |

Parent Ion m/z (MH)⁺ Data for Compounds i-21Ea: 345; i-21Eb: 349; i-21Ec: 345; i-21Ed: 349; i-21Ee: 347; i-21Ef: 355; i-21Eg: 399; i-21Eh: 349; i-21Eh: 346.

Scheme i-22

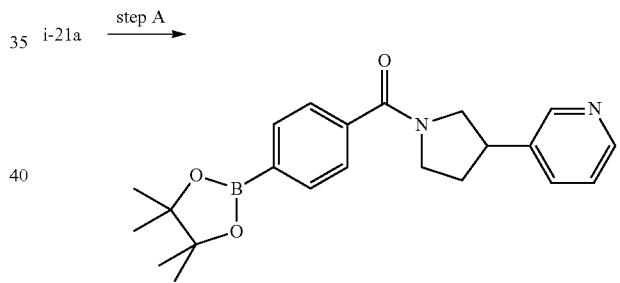

Preparation of i-22a

Step A: Preparation of 3-{1-[4-(4,4,5,5-tetramethyl-1,3,2-dioxaborolan-2-yl)benzoyl]pyrrolidin-3-yl}pyridine (i-22a)

A mixture of i-21a (700 mg, 1.85 mmol), bis(pinacolato)diboron (493 mg, 1.94 mmol), [1,1'-bis(diphenylphosphino)ferrocene]dichloropalladium (II)-DCM complex (151 mg, 0.185 mmol) and potassium acetate (545 mg, 5.55 mmol) in DMSO (15.0 mL) was heated to 70° C. After 5 h, the reaction mixture was cooled to rt, diluted with EtOAc and filtered through a short column of Celite®. The Celite® column was rinsed with EtOAc, and the combined organics were washed with brine, dried (sodium sulfate) and concentrated in vacuo to afford the title compound i-22a. m/z (ES) 379 (MH)⁺.

Following procedures similar to those described above for preparing intermediate i-22a, the following additional intermediates can be prepared.

TABLE i-22
i-22A
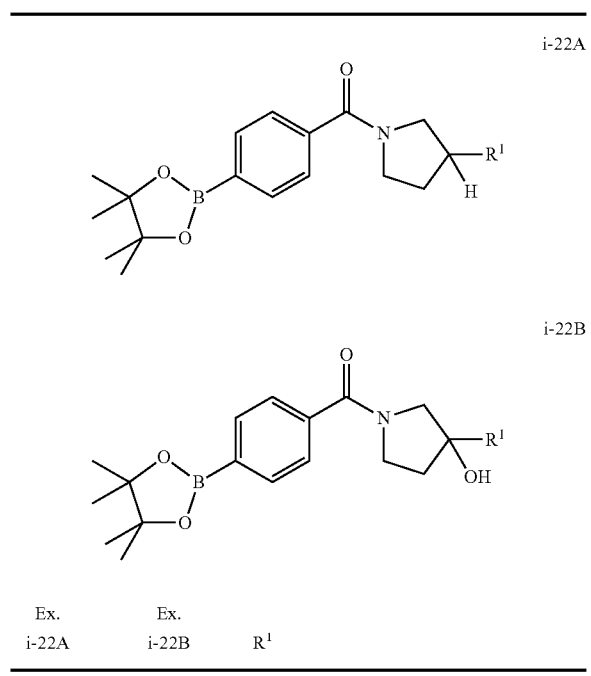
i-22B
| Ex. i-22A | Ex. i-22B | R¹ |
|---|---|---|
| — | a | 3-pyridyl |
| b | b | 5-methyl-3-pyridyl |
| c | c | 5-fluoro-3-pyridyl |
| d | d | 5-chloro-3-pyridyl |
| e | e | 5-methoxy-3-pyridyl |
| f | f | 5-cyano-3-pyridyl |
| g | g | 5-trifluoromethyl-3-pyridyl |
| h | h | 6-methoxy-3-pyridyl |
| i | i | 5-methyl-1,3,4-oxadiazol-2-yl |
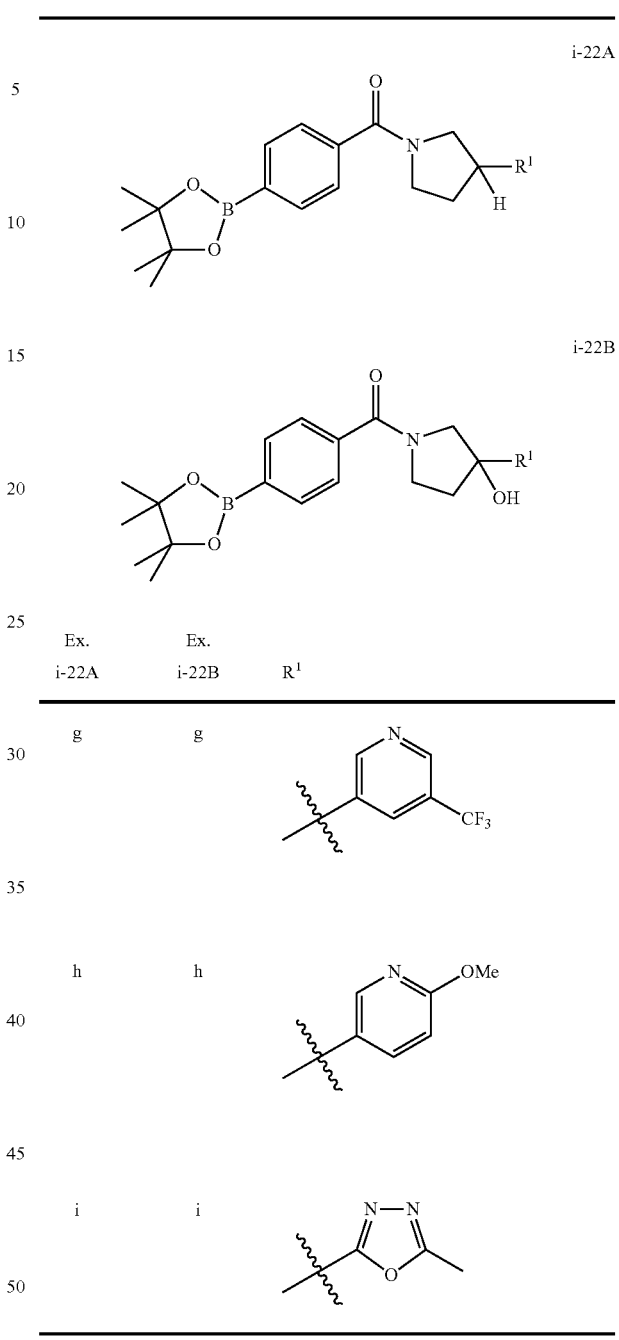
Scheme i-23
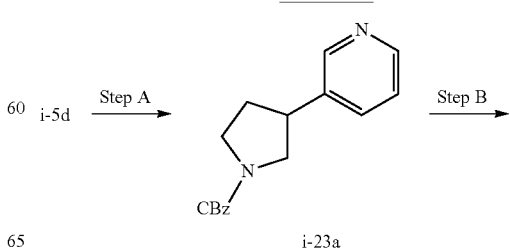

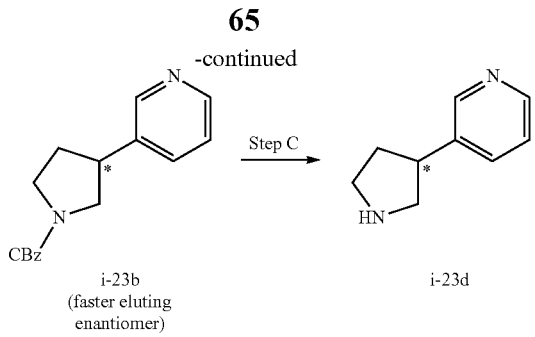

i-23b
(faster eluting enantiomer)

i-23d

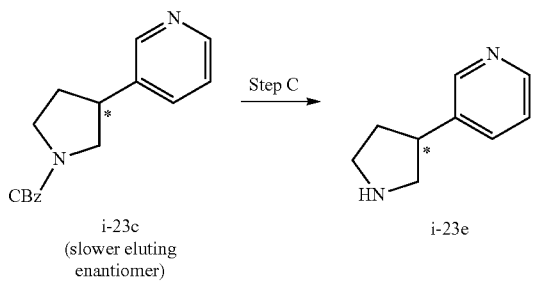

i-23c
(slower eluting enantiomer)

i-23e

\* = enantiomerically pure stereocenter for which the absolute stereochemistry has not been determined Preparation of i-23e Step A: Preparation of benzyl 3-pyridin-3-ylpyrrolidine-1-carboxylate (i-23a)

Benzyl chloroformate (53.6 µL, 0.375 mmol) was added to a stirred solution of i-5d (53.0 mg, 0.356 mmol) and triethylamine (74.8 µL, 0.536 mmol) in DCM (1.80 mL) at rt. After 12 h, the reaction mixture was concentrated in vacuo, and the resulting crude residue was purified by flash chromatography on silica gel (gradient elution; 50%-100% EtOAc/hexane as eluent) afforded the title compound i-23a. $^1$H NMR (500 MHz, CDCl$_3$): δ 8.54 (d, 2H, J=5.7 Hz), 7.57 (d, 1H, J=7.1 Hz), 7.30-7.43 (m, 6H), 5.20 (d, 2H, J=3.4 Hz), 3.98 (m, 1H), 3.71 (m, 1H), 3.55 (m, 1H), 3.44 (m, 2H), 2.36 (m, 1H), 2.04 (m, 1H). m/z (ES) 283 (MH)$^+$.

Step B: Preparation of (i-23b) and (i-23c)

Enantiomers i-23b and i-23c were separated using preparative normal phase chiral HPLC. A solution of i-23a in MeOH was injected onto a CHIRALCEL® OD-H (available from Chiral Technologies, Inc., Exton, Pa.) semi-preparative (250× 20 mm) HPLC column (eluting with 20% MeOH/CO$_2$ with a column temperature of 40° C. at 50 mL/min with UV detection at 220 nm). The enantiomers were separated with the faster eluting enantiomer i-23b having a retention time of 11.64 min and the slower eluting enantiomer i-23c having a retention time of 13.32 min. The separated fractions were concentrated to provide the enantiomers i-23b and i-23c.

Step C: Preparation of 3-pyrrolidin-3-ylpyridine (i-23d)

Palladium on carbon (19.6 mg, 10 wt. % on activated carbon) was added to a solution of i-23b (26.0 mg, 0.092 mmol) in methanol (1.80 mL), and the resulting mixture was hydrogenated (balloon pressure) for 1.5 h. The reaction mixture was filtered through a pad of Celite®, and the solid layer was rinsed with EtOAc. The combined filtrate was concentrated in vacuo to afford the title compound i-23d. m/z (ES) 149 (MH)$^+$.

Compound i-23e was prepared following similar procedures to those described above in step C, substituting i-23c for i-23b. m/z (ES) 149 (MH)$^+$.

In the Tables in the following Examples, compounds having mass spectral data were synthetically prepared.

EXAMPLE 1

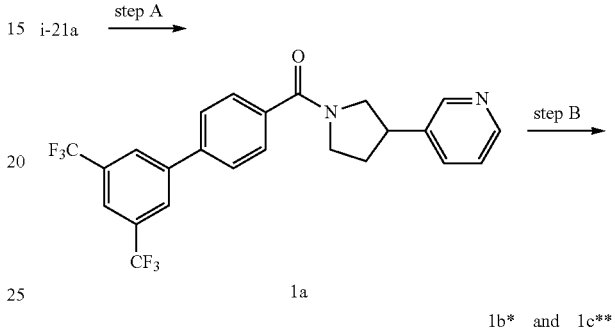

i-21a

1a

1b\* and 1c\*\*

\* = faster eluting enantiomer
\*\* = slower eluting enantiomer

Preparation of 1a

Step A: Preparation of 3-(1-{[3',5'-bis(trifluoromethyl)biphenyl-4-yl]carbonyl}pyrrolidin-3-yl)pyridine (1a)

[1,1'-Bis(diphenylphosphino)ferrocene]dichloropalladium(II) (77.0 mg, 0.106 mmol) was added to a solution of i-21a (400 mg, 1.06 mmol), 3,5-bistrifluorophenylboronic acid (327 mg, 1.27 mmol) and sodium carbonate (1.06 mL of a 2.0 M aq. solution, 2.12 mmol) in EtOH:toluene (7.50 mL of an 80:20 mixture, respectively) at rt. The resulting solution was heated to 125° C. in a sealed microwave vial for 12 min. After cooling to rt, the reaction mixture was filtered through a short column of Celite®, eluting with EtOAc. The filtrate was washed with water and brine, dried (sodium sulfate) and concentrated in vacuo. The crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 1a. m/z (ES) 465 (MH)$^+$.

Step B: Preparation of (1b) and (1c)

Enantiomers 1b and 1c were separated using preparative normal phase chiral HPLC. A solution of 1a in MeOH was injected onto a CHIRALCEL® OD-H (available from Chiral Technologies, Inc., Exton, Pa.) semi-preparative (250×20 mm) HPLC column (eluting with 30% $^i$PrOH/CO$_2$ with a column temperature of 40° C. at 50 mL/min with UV detection at 220 nm). The enantiomers were separated with the faster eluting enantiomer 1b having a retention time of 5.31 min and the slower eluting enantiomer 1c having a retention time of 9.59 min. The separated fractions were concentrated to provide the enantiomers 1b and 1c. For 1c: m/z (ES) 465 (MH)$^+$.

EXAMPLE 2

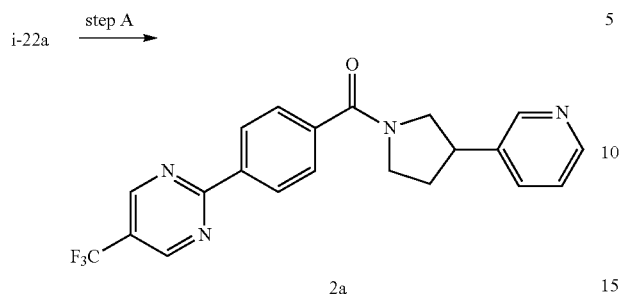

Preparation of 2a

Step A: Preparation of 2-{4-[(3-pyridin-3-ylpyrrolidin-1-yl)carbonyl]phenyl}-5-(trifluoromethyl)pyrimidine (2a)

[1,1'-Bis(diphenylphosphino)ferrocene]dichloropalladium(II) (14.7 mg, 0.020 mmol) was added to a solution of i-22a (38.0 mg, 0.100 mmol), 2-chloro-5-trifluoromethylpyrimidine (20.2 mg, 0.111 mmol) and sodium carbonate (100 μL of a 2.0 M aqueous solution, 0.200 mmol) in EtOH:toluene (1.00 mL of an 3:1 mixture, respectively) at rt. The resulting solution was heated to 125° C. in a sealed microwave vial for 15 min. After cooling to rt, the reaction mixture was filtered through a short column of Celite®, eluting with EtOAc. The filtrate was washed with water and brine, dried (sodium sulfate) and concentrated in vacuo. The crude residue was purified by preparative reversed phase HPLC on YMC Pack Pro C18 stationary phase (CH₃CN/H₂O as eluent, 0.05% TFA as modifier), followed by lyophilization of the purified fractions afforded the title compound 2a. m/z (ES) 399 (MH)⁺.

Following procedures as described above in Examples 1 and 2, the following compounds in Table 2, Table 2A, Table 2B and Table 2C can be prepared:

TABLE 2

2A/2B

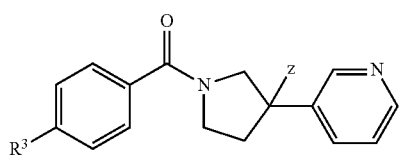

2C/2D

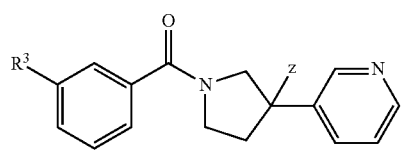

| Ex. 2A z = H | Ex. 2B z = OH | Ex. 2C z = H | Ex. 2D z = OH | R³ |
|---|---|---|---|---|
| a | a | a | a | Ph |
| b | b | b | b | 3,5-(Me)₂-phenyl |
| c | c | c | c | 2-F-phenyl |
| d | d | d | d | 3-F-phenyl |

TABLE 2-continued

2A/2B

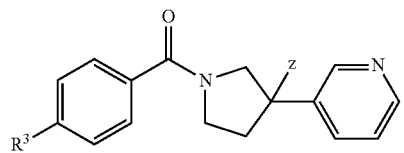

2C/2D

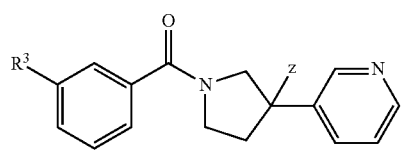

| Ex. 2A z = H | Ex. 2B z = OH | Ex. 2C z = H | Ex. 2D z = OH | R³ |
|---|---|---|---|---|
| e | e | e | e | 4-F-phenyl |
| f | f | f | f | 3,4-Cl₂-phenyl |
| g | g | g | g | 2,5-Cl₂-phenyl |
| h | h | h | h | 3,5-Cl₂-phenyl |
| i | i | i | i | 2,4-Cl₂-phenyl |
| j | j | j | j | 2,3,5-Cl₃-phenyl |
| k | k | k | k | 3-CF₃-phenyl |
| l | l | l | l | 4-CF₃-phenyl |
| — | m | m | m | 3,5-(CF₃)₂-phenyl |
| n | n | n | n | 3-OCF₃-phenyl |
| o | o | o | o | 4-OCF₃-phenyl |
| p | p | p | p | 2-OMe-phenyl |
| q | q | q | q | 2,4-(OEt)₂-phenyl |
| r | r | r | r | 3,5-(Me)₂-4-OMe-phenyl |
| s | s | s | s | 3,5-(Me)₂-4-OEt-phenyl |
| t | t | t | t | 3-F-5-CF₃-phenyl |
| u | u | u | u | 4-OMe-3-CF₃-phenyl |
| v | v | v | v | 3-OMe-5-CF₃-phenyl |
| w | w | w | w | 2-pyridyl |
| x | x | x | x | 3-pyridyl |
| y | y | y | y | 4-pyridyl |
| z | z | z | z | 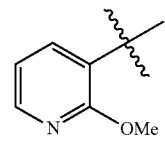 |
| aa | aa | aa | aa | 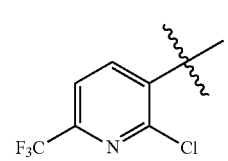 |
| ab | ab | ab | ab | 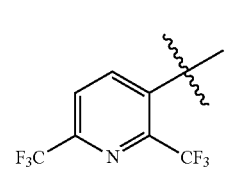 |
| ac | ac | ac | ac | 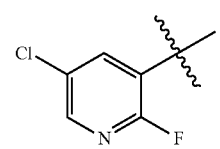 [SMILES: *c1cc(Cl)cnc1F] |

TABLE 2-continued
| Ex. 2A z = H | Ex. 2B z = OH | Ex. 2C z = H | Ex. 2D z = OH | R³ |
|---|---|---|---|---|
| ad | ad | ad | ad | 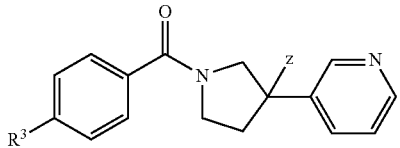 |
| ae | ae | ae | ae | 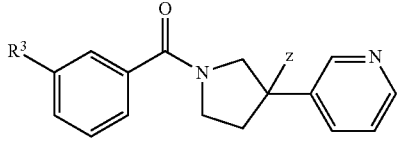 |
| af | af | af | af | 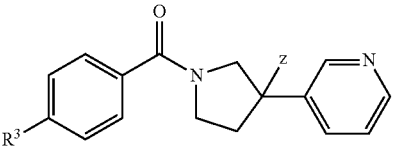 |
| ag | ag | ag | ag | 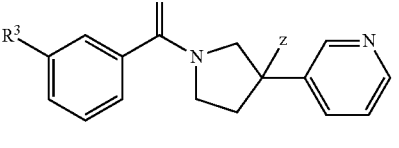 |
| ah | ah | ah | ah | 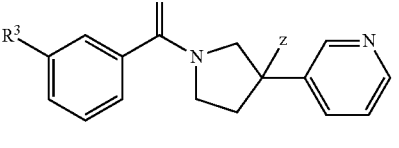 |
| ai | ai | ai | ai | 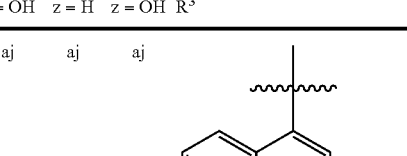 |
TABLE 2-continued
| Ex. 2A z = H | Ex. 2B z = OH | Ex. 2C z = H | Ex. 2D z = OH | R³ |
|---|---|---|---|---|
| aj | aj | aj | aj | 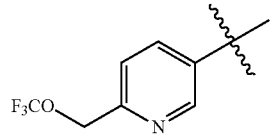 [SMILES: *c1ccc(COC(F)(F)F)nc1] |
| ak | ak | ak | ak | 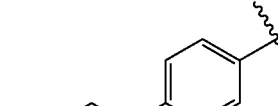 |
| al | al | al | al | 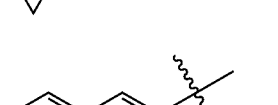 |
| am | am | am | am | 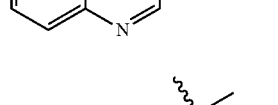 |
| — | an | an | an | 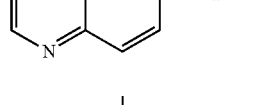 |
| ao | ao | ao | ao | 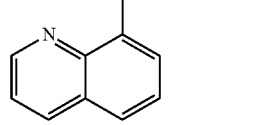 |
| ap | ap | ap | ap | 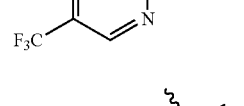 |

TABLE 2-continued

2A/2B

2C/2D

| Ex. 2A z = H | Ex. 2B z = OH | Ex. 2C z = H | Ex. 2D z = OH | R³ |
|---|---|---|---|---|
| aq | aq | aq | aq | 2,3-dihydrobenzofuran-5-yl |
| ar | ar | ar | ar | benzo[1,3]dioxol-5-yl |
| as | as | as | as | 5-methyl-1,3,4-oxadiazol-2-yl-phenyl |
| at | at | at | at | pyrazol-1-yl |
| au | au | au | au | 3,5-dimethylpyrazol-1-yl |

Table 2. Parent Ion m/z (MH)⁺ Data for Compounds
For 2Aa: 3-[1-(biphenyl-4-ylcarbonyl)pyrrolidin-3-yl]pyridine: m/z (ES)=329 (MH)⁺
For 2Ab: 3-{1-[(3',5'-dimethylbiphenyl-4-yl)carbonyl]pyrrolidin-3-yl}pyridine: m/z (ES)=357 (MH)⁺
For 2Ad: 3-{1-[(3'-fluorobiphenyl-4-yl)carbonyl]pyrrolidin-3-yl}pyridine: m/z (ES)=347 (MH)⁺
For 2Ae: 3-{1-[(4'-fluorobiphenyl-4-yl)carbonyl]pyrrolidin-3-yl}pyridine: m/z (ES)=347 (MH)⁺
For 2Af: 3-{1-[(3',4'-dichlorobiphenyl-4-yl)carbonyl]pyrrolidin-3-yl}pyridine: m/z (ES)=397 (MH)⁺
For 2Ag: 3-{1-[(2',5'-dichlorobiphenyl-4-yl)carbonyl]pyrrolidin-3-yl}pyridine: m/z (ES)=397 (MH)⁺
For 2Ah: 3-{1-[(3',5'-dichlorobiphenyl-4-yl)carbonyl]pyrrolidin-3-yl}pyridine: m/z (ES)=397 (MH)⁺
For 2Ai: 3-{1-[(2',4'-dichlorobiphenyl-4-yl)carbonyl]pyrrolidin-3-yl}pyridine: m/z (ES)=397 (MH)⁺
For 2Aj: 3-{1-[(2',3',5'-trichlorobiphenyl-4-yl)carbonyl]pyrrolidin-3-yl}pyridine: m/z (ES)=431 (MH)⁺
For 2Ak: 3-(1-{[3'-(trifluoromethyl)biphenyl-4-yl]carbonyl}pyrrolidin-3-yl)pyridine: m/z (ES)=397 (MH)⁺
For 2Al: 3-(1-{[4'-(trifluoromethyl)biphenyl-4-yl]carbonyl}pyrrolidin-3-yl)pyridine: m/z (ES)=397 (MH)⁺
For 2An: 3-(1-{[3'-(trifluoromethoxy)biphenyl-4-yl]carbonyl}pyrrolidin-3-yl)pyridine: m/z (ES)=413 (MH)⁺
For 2Ao: 3-(1-{[4'-(trifluoromethoxy)biphenyl-4-yl]carbonyl}pyrrolidin-3-yl)pyridine: m/z (ES)=413 (MH)⁺
For 2Ap: 3-{1-[(2'-methoxybiphenyl-4-yl)carbonyl]pyrrolidin-3-yl}pyridine: m/z (ES)=359 (MH)⁺
For 2Aq: 3-{1-[(2',4'-diethoxybiphenyl-4-yl)carbonyl]pyrrolidin-3-yl}pyridine: m/z (ES)=417 (MH)⁺
For 2Ar: 3-{1-[(4'-methoxy-3',5'-dimethylbiphenyl-4-yl)carbonyl]pyrrolidin-3-yl}pyridine: m/z (ES)=387 (MH)⁺
For 2As: 3-{1-[(4'-ethoxy-3',5'-dimethylbiphenyl-4-yl)carbonyl]pyrrolidin-3-yl}pyridine: m/z (ES)=401 (MH)⁺
For 2At: 3-(1-{[3'-fluoro-5'-(trifluoromethyl)biphenyl-4-yl]carbonyl}pyrrolidin-3-yl)pyridine: m/z (ES)=415 (MH)⁺
For 2Au: 3-(1-{[4'-methoxy-3'-(trifluoromethyl)biphenyl-4-yl]carbonyl}pyrrolidin-3-yl)pyridine: m/z (ES)=427 (MH)⁺
For 2Av: 3-(1-{[3'-methoxy-5'-(trifluoromethyl)biphenyl-4-yl]carbonyl}pyrrolidin-3-yl)pyridine: m/z (ES)=427 (MH)⁺
For 2Ax: 3-[1-(4-pyridin-3-ylbenzoyl)pyrrolidin-3-yl]pyridine: m/z (ES)=330 (MH)⁺
For 2Ay: 3-[1-(4-pyridin-4-ylbenzoyl)pyrrolidin-3-yl]pyridine: m/z (ES)=330 (MH)⁺
For 2Az: 2-methoxy-3-{4-[(3-pyridin-3-ylpyrrolidin-1-yl)carbonyl]phenyl}pyridine: m/z (ES)=360 (MH)⁺
For 2Aaa: 2-chloro-3-{4-[(3-pyridin-3-ylpyrrolidin-1-yl)carbonyl]phenyl}-6-trifluoromethyl)pyridine: m/z (ES)=432 (MH)⁺
For 2Aab: 3-{4-[(3-pyridin-3-ylpyrrolidin-1-yl)carbonyl]phenyl}-2,6-bis(trifluoromethyl)pyridine: m/z (ES)=466 (MH)⁺
For 2Aac: 5-chloro-2-fluoro-3-{4-[(3-pyridin-3-ylpyrrolidin-1-yl)carbonyl]phenyl}pyridine: m/z (ES)=382 (MH)⁺
For 2Aad: 5-{4-[(3-pyridin-3-ylpyrrolidin-1-yl)carbonyl]phenyl}-2-[(trifluoromethoxy)methyl]pyridine: m/z (ES)=428 (MH)⁺
For 2Aae: 2-(cyclopropylmethoxy)-5-{4-[(3-pyridin-3-ylpyrrolidin-1-yl)carbonyl]phenyl}pyridine: m/z (ES)=400 (MH)⁺
For 2Aaf: 3-{4-[(3-pyridin-3-ylpyrrolidin-1-yl)carbonyl]phenyl}quinoline: m/z (ES)=380 (MH)⁺
For 2Aag: 6-{4-[(3-pyridin-3-ylpyrrolidin-1-yl)carbonyl]phenyl}quinoline: m/z (ES)=380 (MH)⁺
For 2Aah: 8-{4-[(3-pyridin-3-ylpyrrolidin-1-yl)carbonyl]phenyl}quinoline: m/z (ES)=380 (MH)⁺
For 2Aai: 5,6-difluoro-2-methyl-8-{4-[(3-pyridin-3-ylpyrrolidin-1-yl)carbonyl]phenyl}quinoline: m/z (ES)=430 (MH)⁺
For 2Aaj: 5-{4-[(3-pyridin-3-ylpyrrolidin-1-yl)carbonyl]phenyl}isoquinoline: m/z (ES)=380 (MH)⁺
For 2Aak: 5-{4-[(3-pyridin-3-ylpyrrolidin-1-yl)carbonyl]phenyl}pyrimidine: m/z (ES)=331 (MH)⁺
For 2Aal: 5-{4-[(3-pyridin-3-ylpyrrolidin-1-yl)carbonyl]phenyl}pyrimidin-2-amine: m/z (ES)=346 (MH)⁺
For 2Aam: 2-methoxy-5-{4-[(3-pyridin-3-ylpyrrolidin-1-yl)carbonyl]phenyl}pyrimidine: m/z (ES)=361 (MH)⁺
For 2Aao: 5-{4-[(3-pyridin-3-ylpyrrolidin-1-yl)carbonyl]phenyl}pyrazin-2-amine: m/z (ES)=346 (MH)⁺
For 2Aap: 3-[1-({4'-[(trifluoromethoxy)methyl]biphenyl-4-yl}carbonyl)pyrrolidin-3-yl]pyridine: m/z (ES)=427 (MH)⁺

For 2Aaq: 3-{1-[4-(2,3-dihydro-1-benzofuran-5-yl)benzoyl]pyrrolidin-3-yl}pyridine: m/z (ES)=371 (MH)+

For 2Aar: 3-{1-[4-(1,3-benzodioxol-5-yl)benzoyl]pyrrolidin-3-yl}pyridine: m/z (ES)=373 (MH)+

For 2Aas: 3-(1-{[3'-(5-methyl-1,3,4-oxadiazol-2-yl)biphenyl-4-yl]carbonyl}pyrrolidin-3-yl)pyridine: m/z (ES)=411 (MH)+

For 2Aat: 3-{1-[4-(1H-pyrazol-1-yl)benzoyl]pyrrolidin-3-yl}pyridine: m/z (ES)=319 (MH)+

For 2Aau: 3-{1-[4-(3,5-dimethyl-1H-pyrazol-1-yl)benzoyl]pyrrolidin-3-yl}pyridine: m/z (ES)=347 (MH)+

For 2Bm: 1-{[3',5'-bis(trifluoromethyl)biphenyl-4-yl]carbonyl}-3-pyridin-3-ylpyrrolidin-3-ol: m/z (ES)=481 (MH)+

For 2Ca: 3-[1-(biphenyl-3-ylcarbonyl)pyrrolidin-3-yl]pyridine: m/z (ES)=329 (MH)+

For 2Cd: 3-{1-[(3'-fluorobiphenyl-3-yl)carbonyl]pyrrolidin-3-yl}pyridine: m/z (ES)=347 (MH)+

For 2Ce: 3-{1-[(4'-fluorobiphenyl-3-yl)carbonyl]pyrrolidin-3-yl}pyridine: m/z (ES)=347 (MH)+

For 2 Cm: 3-(1-{[3',5'-bis(trifluoromethyl)biphenyl-3-yl]carbonyl}pyrrolidin-3-yl)pyridine: m/z (ES)=465 (MH)+

For 2Cn: 3-(1-{[3'-(trifluoromethoxy)biphenyl-3-yl]carbonyl}pyrrolidin-3-yl)pyridine: m/z (ES)=413 (MH)+

For 2Co: 3-(1-{[4'-(trifluoromethoxy)biphenyl-3-yl]carbonyl}pyrrolidin-3-yl)pyridine: m/z (ES)=413 (MH)+

For 2Cx: 3-[1-(3-pyridin-3-ylbenzoyl)pyrrolidin-3-yl]pyridine: m/z (ES)=330 (MH)+

For 2Cy: 3-[1-(3-pyridin-4-ylbenzoyl)pyrrolidin-3-yl]pyridine: m/z (ES)=330 (MH)+

For 2Caf: 3-{3-[(3-pyridin-3-ylpyrrolidin-1-yl)carbonyl]phenyl}quinoline: m/z (ES)=380 (MH)+

For 2Cag: 6-{3-[(3-pyridin-3-ylpyrrolidin-1-yl)carbonyl]phenyl}quinoline: m/z (ES)=380 (MH)+

For 2Cah: 8-{3-[(3-pyridin-3-ylpyrrolidin-1-yl)carbonyl]phenyl}quinoline: m/z (ES)=380 (MH)+

For 2Caj: 5-{3-[(3-pyridin-3-ylpyrrolidin-1-yl)carbonyl]phenyl}isoquinoline: m/z (ES)=380 (MH)+

For 2Cao: 5-{3-[(3-pyridin-3-ylpyrrolidin-1-yl)carbonyl]phenyl}pyrazin-2-amine: m/z (ES) 346 (MH)+

TABLE 2A

2E/2F

| Ex. 2E z = H | Ex. 2F z = OH | R² | R³ |
|---|---|---|---|
| a | a | F | Ph |
| b | b | F | 3,5-(CF₃)₂-phenyl |
| c | c | Me | Ph |
| d | d | Me | 3,5-(CF₃)₂-phenyl |
| e | e | Me | 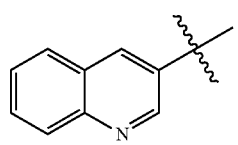 [SMILES: *c1cnc2ccccc2c1] |
| f | f | Me | |

TABLE 2A-continued

2E/2F

Table 2A. Parent Ion m/z (MH)+ Data for Compounds

For 2Ea: 3-{1-[(3-fluorobiphenyl-4-yl)carbonyl]pyrrolidin-3-yl}pyridine: m/z (ES)=347 (MH)+

For 2Eb: 3-(1-{[3-fluoro-3',5'-bis(trifluoromethyl)biphenyl-4-yl]carbonyl}pyrrolidin-3-yl)pyridine: m/z (ES)=483 (MH)+

For 2Ec: 3-{1-[(3-methylbiphenyl-4-yl}carbonyl]pyrrolidin-3-yl}pyridine: m/z (ES)=343 (MH)+

For 2Ed: 3-(1-{[3-methyl-3',5'-bis(trifluoromethyl)biphenyl-4-yl]carbonyl}pyrrolidin-3-yl)pyridine: m/z (ES)=479 (MH)+

For 2Ee: 3-{3-methyl-4-[(3-pyridin-3-ylpyrrolidin-1-yl)carbonyl]phenyl}quinoline: m/z (ES)=394 (MH)+

For 2Ef: 8-{3-methyl-4-[(3-pyridin-3-ylpyrrolidin-1-yl)carbonyl]phenyl}quinoline: m/z (ES)=394 (MH)+

TABLE 2B

2G/2H

| Ex. 2G z = H | Ex. 2H z = OH | R² | R³ |
|---|---|---|---|
| a | a | F | Ph |
| b | b | F | 3,5-(CF₃)₂-phenyl |
| c | c | Me | Ph |
| d | d | Me | 3,5-(CF₃)₂-phenyl |
| e | e | CF₃ | 3,5-(CF₃)₂-phenyl |
| f | f | OCF₃ | 3,5-(CF₃)₂-phenyl |
| g | g | Ph | NH₂ |
| h | h | Ph | I |

Table 2B. Parent Ion m/z (MH)+ Data for Compounds

For 2Ga: 3-{1-[(2-fluorobiphenyl-4-yl)carbonyl]pyrrolidin-3-yl}pyridine: m/z (ES)=347 (MH)+

For 2Gb: 3-(1-{[2-fluoro-3',5'-bis(trifluoromethyl)biphenyl-4-yl]carbonyl}pyrrolidin-3-yl)pyridine: m/z (ES)=483 (MH)+

For 2Gc: 3-{1-[(2-methylbiphenyl-4-yl)carbonyl]pyrrolidin-3-yl}pyridine: m/z (ES)=343 (MH)+

For 2Gd: 3-(1-{[2-methyl-3',5'-bis(trifluoromethyl)biphenyl-4-yl]carbonyl}pyrrolidin-3-yl)pyridine: m/z (ES)=479 (MH)+

For 2Ge: 3-(1-{[2,3',5'-tris(trifluoromethyl)biphenyl-4-yl]carbonyl}pyrrolidin-3-yl)pyridine: m/z (ES)=533 (MH)+

For 2Gf: 3-(1-{[2-(trifluoromethoxy)-3',5'-bis(trifluoromethyl)biphenyl-4-yl]carbonyl}pyrrolidin-3-yl)pyridine: m/z (ES)=549 (MH)+

For 2Gg: 5-[(3-pyridin-3-ylpyrrolidin-1-yl)carbonyl]biphenyl-2-amine: m/z (ES)=344 (MH)+

For 2Gh: 3-{1-[(6-iodobiphenyl-3-yl)carbonyl]pyrrolidin-3-yl}pyridine: m/z (ES)=455 (MH)+

TABLE 2C

2I/2J

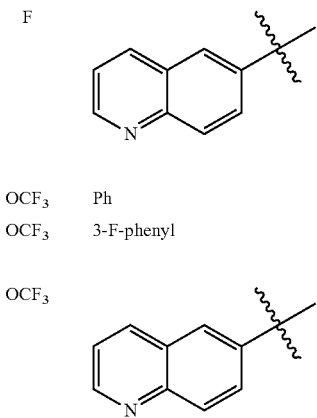

| Ex. 2I z = H | Ex. 2J z = OH | R² | R³ |
|---|---|---|---|
| a | a | F | Ph |
| b | b | F | 3-F-phenyl |
| c | c | F | 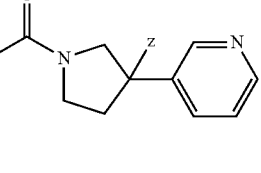 |
| d | d | OCF₃ | Ph |
| e | e | OCF₃ | 3-F-phenyl |
| f | f | OCF₃ | (6-quinolinyl) |
| h | h | CF₃ | Ph |
| i | i | CF₃ | 3-F-phenyl |
| j | j | CF₃ | 3-CF₃-phenyl |
| k | k | CF₃ | 4-CF₃-phenyl |
| l | l | CF₃ | 3,5-(CF₃)₂-phenyl |
| m | m | CF₃ | (5-pyrimidinyl) |
| n | n | CF₃ | (6-quinolinyl) |

TABLE 2C-continued

2I/2J

| Ex. 2I z = H | Ex. 2J z = OH | R² | R³ |
|---|---|---|---|
| o | o | CF₃ | (5-indolyl) |

Table 2C. Parent Ion m/z (MH)+ Data for Compounds

For 2Ia: 3-{1-[(5-fluorobiphenyl-3-yl)carbonyl]pyrrolidin-3-yl}pyridine: m/z (ES)=347 (MH)+

For 2Ib: 3-{1-[(3',5-difluorobiphenyl-3-yl)carbonyl]pyrrolidin-3-yl}pyridine: m/z (ES)=365 (MH)+

For 2Ic: 6-{3-fluoro-5-[(3-pyridin-3-ylpyrrolidin-1-yl)carbonyl]phenyl}quinoline: m/z (ES)=398 (MH)+

For 2Id: 3-(1-{[5-(trifluoromethoxy)biphenyl-3-yl]carbonyl}pyrrolidin-3-yl)pyridine: m/z (ES)=413 (MH)+

For 2Ie: 3-(1-{[3'-fluoro-5-(trifluoromethoxy)biphenyl-3-yl]carbonyl}pyrrolidin-3-yl)pyridine: m/z (ES)=431 (MH)+

For 2If: 6-[3-[(3-pyridin-3-ylpyrrolidin-1-yl)carbonyl]-5-(trifluoromethoxy)phenyl]quinoline: m/z (ES)=464 (MH)+

For 2Ih: 3-(1-{[5-(trifluoromethyl)biphenyl-3-yl]carbonyl}pyrrolidin-3-yl)pyridine: m/z (ES)=397 (MI-1)+

For 2Ii: 3-(1-{[3'-fluoro-5-(trifluoromethyl)biphenyl-3-yl]carbonyl}pyrrolidin-3-yl)pyridine: m/z (ES)=415 (MH)+

For 2Ij: 3-(1-{[3',5-bis(trifluoromethyl)biphenyl-3-yl]carbonyl}pyrrolidin-3-yl)pyridine: m/z (ES)=465 (MH)+

For 2Ik: 3-(1-{[4',5-bis(trifluoromethyl)biphenyl-3-yl]carbonyl}pyrrolidin-3-yl)pyridine: m/z (ES)=465 (MH)+

For 2Il: 3-(1-{[3',5,5'-tris(trifluoromethyl)biphenyl-3-yl]carbonyl}pyrrolidin-3-yl)pyridine: m/z (ES)=533 (MH)+

For 2Im: 5-[3-[(3-pyridin-3-ylpyrrolidin-1-yl)carbonyl]-5-(trifluoromethyl)phenyl]pyrimidine: m/z (ES)=399 (MH)+

For 2In: 6-[3-[(3-pyridin-3-ylpyrrolidin-1-yl)carbonyl]-5-(trifluoromethyl)phenyl]quinoline: m/z (ES)=448 (MH)+

For 2Io: 5-[3-[(3-pyridin-3-ylpyrrolidin-1-yl)carbonyl]-5-(trifluoromethyl)phenyl]-1H-indole: m/z (ES)=436 (MH)+

EXAMPLE 3

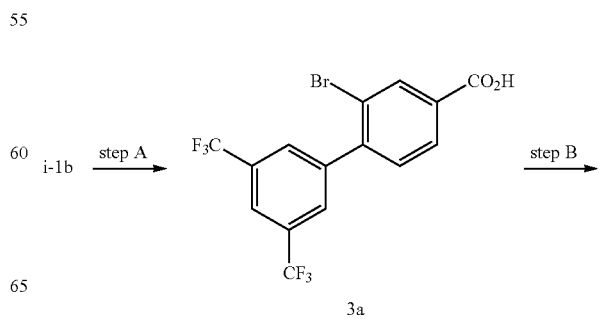

3a

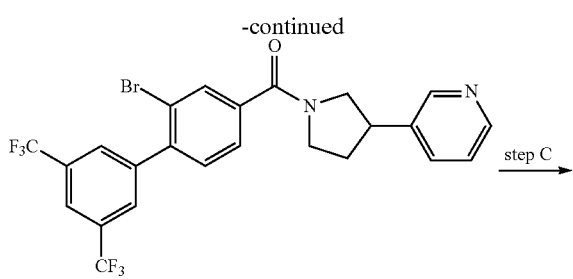

3b

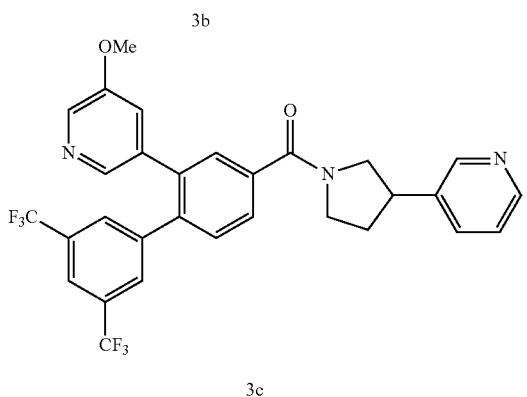

3c

Preparation of 3c

Step A: Preparation of 2-bromo-3',5'-bis(trifluoromethyl)biphenyl-4-carboxylic acid (3a)

Lithium hydroxide hydrate (65.0 mg, 2.72 mmol) was added to a stirred solution of i-1b (580 mg, 1.36 mmol) in dioxane:water (7.50 mL of a 2:1 mixture, respectively). After the reaction was deemed complete, the reaction mixture was quenched with 1.0 M HCl and extracted with EtOAc. The combined organics were washed with brine, dried (sodium sulfate) and concentrated in vacuo to afford the title compound 3a.

Step B: Preparation of 3-(1-{[2-bromo-3',5'-bis(trifluoromethyl)biphenyl-4-yl]carbonyl}pyrrolidin-3-yl)pyridine (3b)

i-5d (179 mg, 1.21 mmol) was added to a stirred solution of 3a (500 mg, 1.21 mmol), N-(3-dimethylaminopropyl)-N-ethylcarbodiimide hydrochloride (255 mg, 1.33 mmol) and 1-hydroxybenzotriazole 185 mg, 1.21 mmol) in DMF (8.00 mL). After 4 h, the reaction mixture was quenched with said, aq. $NaHCO_3$ and extracted with EtOAc. The organic layer was washed with water and brine, dried (sodium sulfate) and concentrated in vacuo. The resulting crude residue was purified by column chromatography on silica gel (gradient elution; 0%-5% methanol/EtOAc as eluent) to afford the title compound 3b. m/z (ES) 543 $(MH)^+$.

Step C: Preparation of 3-methoxy-5-[4-[(3-pyridin-3-ylpyrrolidin-1-yl)carbonyl]-3',5'-bis(trifluoromethyl)biphenyl-2-yl]pyridine (3c)

[1,1'-Bis(diphenylphosphino)ferrocene]dichloropalladium(II) (13.7 mg, 0.019 mmol) was added to a solution of 3b (51.0 mg, 0.094 mmol), 3-methoxy-5-(4,4,5,5-tetramethyl-1,3,2-dioxaborolan-2-yl)pyridine (24.3 mg, 0.103 mmol) and sodium carbonate (94.0 µL, of a 2.0 M aqueous solution, 0.188 mmol) in EtOH:toluene (1.25 mL of an 80:20 mixture, respectively) at rt. The resulting solution was heated to 125° C. in a sealed microwave vial for 12 min. After cooling to rt, the reaction mixture was filtered through a short column of Celite®, eluting with EtOAc. The filtrate was washed with water and brine, dried (sodium sulfate) and concentrated in vacuo. The crude residue was purified by preparative reversed phase HPLC on YMC Pack Pro C18 stationary phase ($CH_3CN/H_2O$ as eluent, 0.05% TFA as modifier), followed by lyophilization of the purified fractions afforded the title compound 3c. m/z (ES) 572 $(MH)^+$.

Following procedures as described above in Example 3, steps A and B, the following compounds in Table 3A and 3B can be prepared:

TABLE 3A

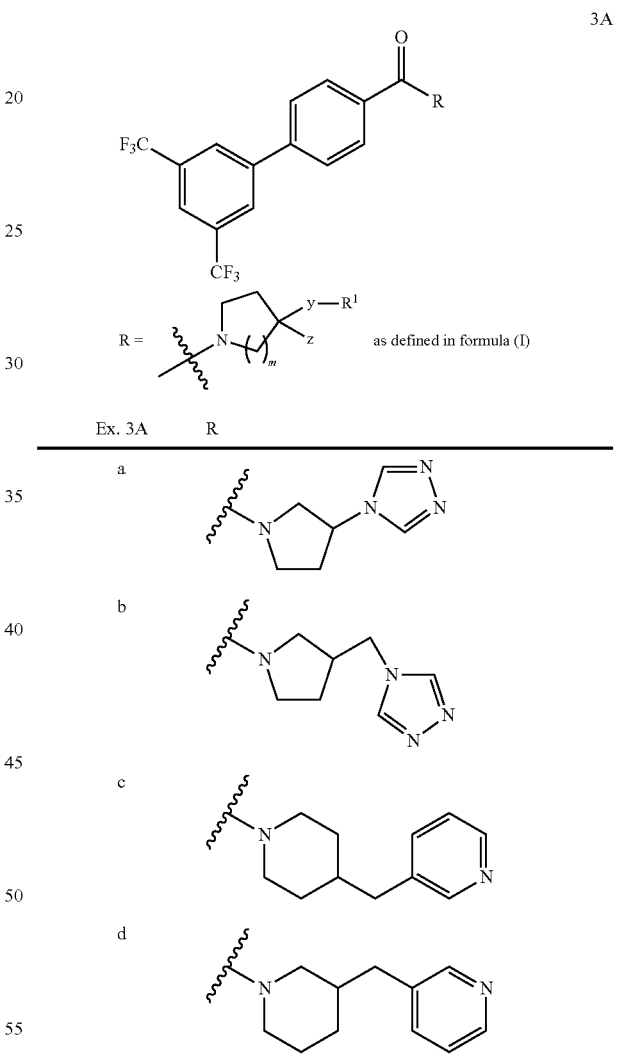

| Ex. 3A | R |
|---|---|
| a | (1,2,4-triazol-1-yl pyrrolidine) |
| b | (1,2,4-triazol-4-ylmethyl pyrrolidine) |
| c | (pyridin-3-ylmethyl piperidine, 4-substituted) |
| d | (pyridin-3-ylmethyl piperidine, 3-substituted) |

Table 3A. Parent Ion m/z $(MH)^+$ Data for Compounds

For 3Aa: 4-(1-{[3',5'-bis(trifluoromethyl)biphenyl-4-yl]carbonyl}pyrrolidin-3-yl)-4H-1,2,4-triazole: m/z (ES)=455 $(MH)^+$ For 3Ab: 4-[(1-{[3',5'-bis(trifluoromethyl)biphenyl-4-yl]carbonyl}pyrrolidin-3-yl)methyl]-4H-1,2,4-triazole: m/z (ES)=469 $(MH)^+$ For 3Ac: 3-[(1-{[3',5'-bis(trifluoromethyl)biphenyl-4-yl]carbonyl}piperidin-4-yl)methyl]pyridine: m/z (ES)=493 $(MH)^+$ For 3Ad: 3-[(1-{[3',5'-bis(trifluoromethyl)biphenyl-4-yl]carbonyl}piperidin-3-yl)methyl]pyridine: m/z (ES)=493 (MH)+

TABLE 3B

| Ex. 3B | Ex. 3C | Ex. 3D | R¹ |
|---|---|---|---|
| — | a | a | 3-pyridyl |
| b | b | b | 5-methylpyridin-3-yl |
| c | c | c | 5-fluoropyridin-3-yl |
| d | d | d | 5-chloropyridin-3-yl |
| e | e | e | 5-cyanopyridin-3-yl |
| f | f | f | 5-(trifluoromethyl)pyridin-3-yl |
| g | g | g | 5-methoxypyridin-3-yl |
| h | h | h | 6-methoxypyridin-3-yl |
| i | i | i | 5-methyl-1,3,4-oxadiazol-2-yl |

Table 3B. Parent Ion m/z (MH)+ Data for Compounds

For 3Bb: 3-(1-{[3',5'-bis(trifluoromethyl)biphenyl-4-yl]carbonyl}pyrrolidin-3-yl)-5-methylpyridine: m/z (ES)=479 (MH)+

For 3Bc: 3-(1-{[3',5'-bis(trifluoromethyl)biphenyl-4-yl]carbonyl}pyrrolidin-3-yl)-5-fluoropyridine: m/z (ES) 483 (MH)+

For 3Bg: 3-(1-{[3',5'-bis(trifluoromethyl)biphenyl-4-yl]carbonyl}pyrrolidin-3-yl)-5-methoxypyridine: adz (ES)=495 (MH)+

For 3Bi: 2-(1-{[3',5'-bis(trifluoromethyl)biphenyl-4-yl]carbonyl}pyrrolidin-3-yl)-5-methyl-1,3,4-oxadiazole: m/z (ES)=470 (MH)+

For 3Ca: 3-(1-{[3',5'-bis(trifluoromethyl)biphenyl-4-yl]carbonyl}-3-fluoropyrrolidin-3-yl)pyridine: m/z (ES)=483 (MH)+

For 3Dc: 1-{[3',5'-bis(trifluoromethyl)biphenyl-4-yl]carbonyl}-3-(5-fluoropyridin-3-yl)pyrrolidin-3-ol: m/z (ES)=499 (MH)+

For 3Dd: 1-{[3',5'-bis(trifluoromethyl)biphenyl-4-yl]carbonyl}-3-(5-chloropyridin-3-yl)pyrrolidin-3-ol: m/z (ES)=515 (MH)+

For 3De: 5-(1-{[3',5'-bis(trifluoromethyl)biphenyl-4-yl]carbonyl}-3-hydroxypyrrolidin-3-yl)nicotinonitrile: m/z (ES)=506 (MH)+

For 3Df: 1-{[3',5'-bis(trifluoromethyl)biphenyl-4-yl]carbonyl}-3-[5-(trifluoromethyl)pyridin-3-yl]pyrrolidin-3-ol: m/z (ES)=549 (MH)+

For 3Dh: 1-{[3',5'-bis(trifluoromethyl)biphenyl-4-yl]carbonyl}-3-(6-methoxypyridin-3-yl)pyrrolidin-3-ol: m/z (ES)=511 (MH)+

Following procedures as described above in Example 3, steps A through C, the following compounds in Table 3C and 3D can be prepared:
TABLE 3C
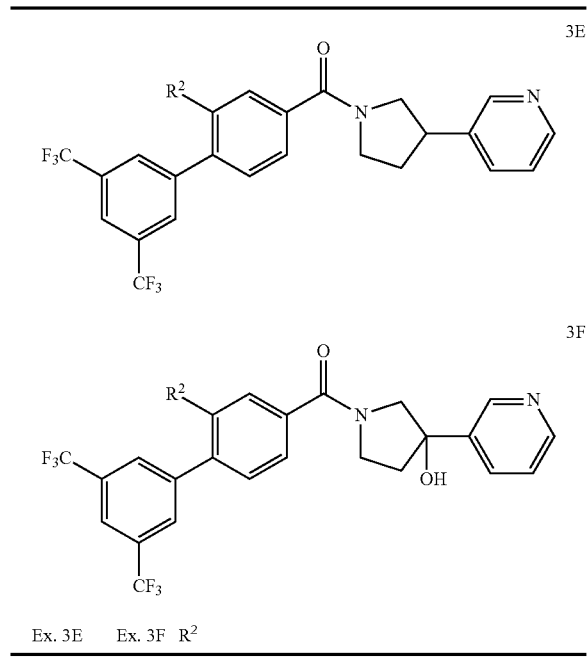
| Ex. 3E | Ex. 3F | R² |
|---|---|---|
| a | a | Ph |
| b | b | 3-F—Ph |
| c | c | 4-F—Ph |
| d | d | 4-OCF₃—Ph |
| e | e | 3-pyridyl |
| f | f | 4-pyridyl |
| g | g | 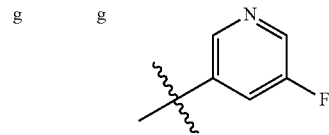 |
| h | h | 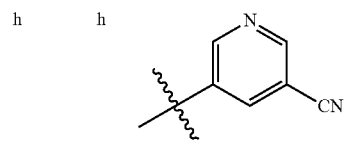 |
| i | i | 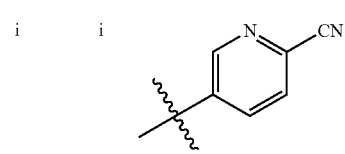 |
| j | j | 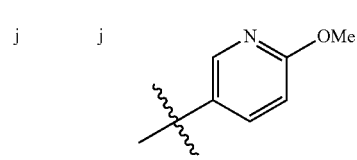 |
| k | k | 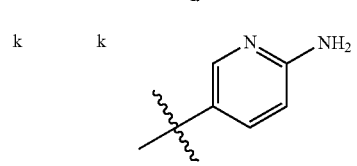 |
TABLE 3C-continued
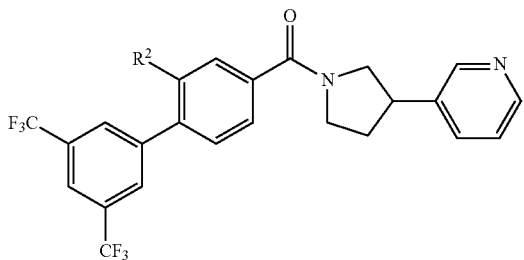
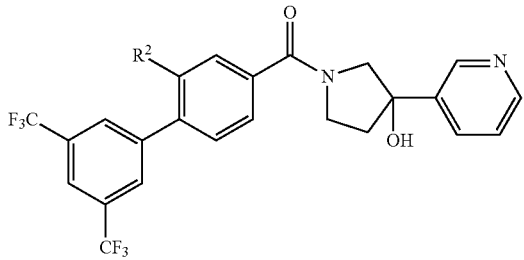
| Ex. 3E | Ex. 3F | R² |
|---|---|---|
| l | l | 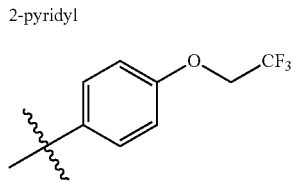 |
| m | m | 2-pyridyl |
| n | n |  |
| o | o |  |
| p | p |  |
| q | q |  |
| r | r |  |

TABLE 3C-continued

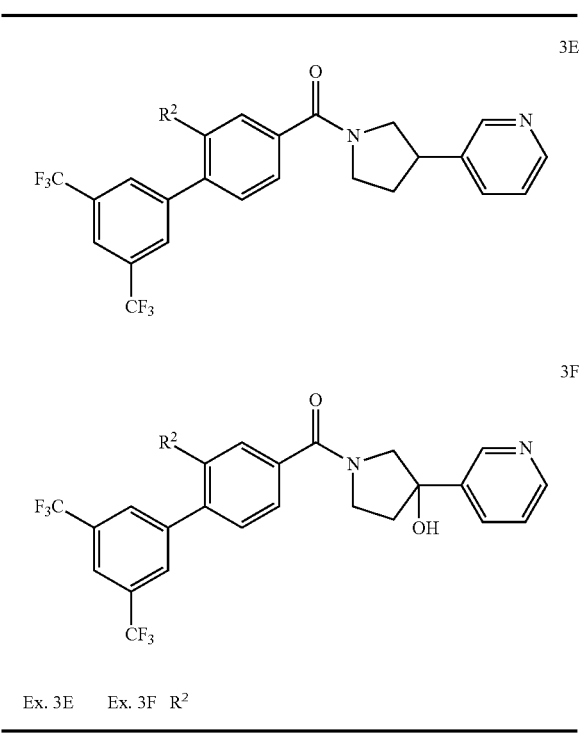

3E

3F

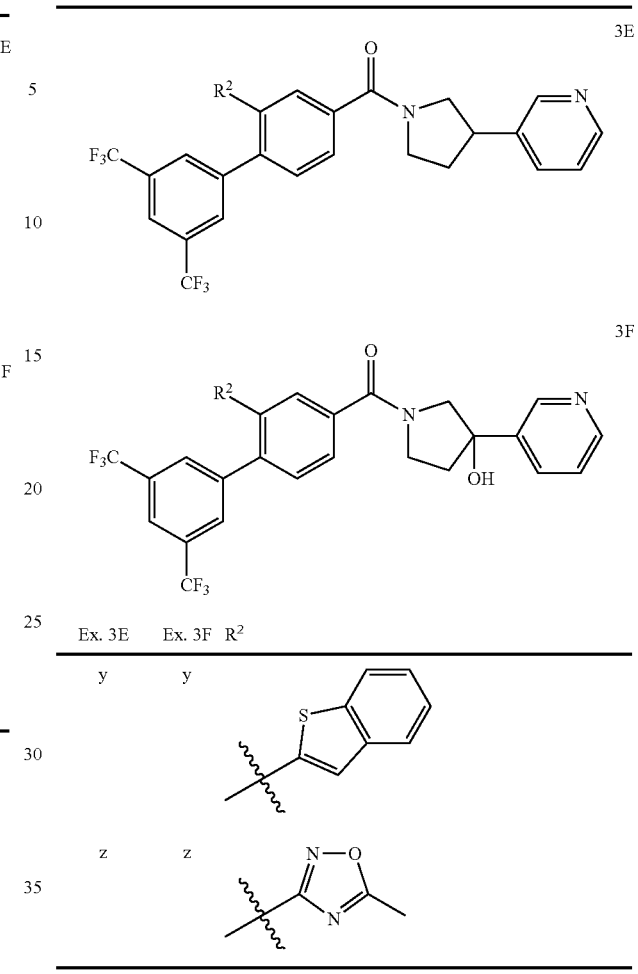

3E

3F

| Ex. 3E | Ex. 3F | R² |
|---|---|---|
| s | s | pyrimidine-OMe |
| t | t | pyrimidine-CF₃ |
| u | u | pyrazine-NH₂ |
| v | v | oxazole |
| w | w | pyrazole (3-yl) |
| x | x | pyrazole (4-yl) |

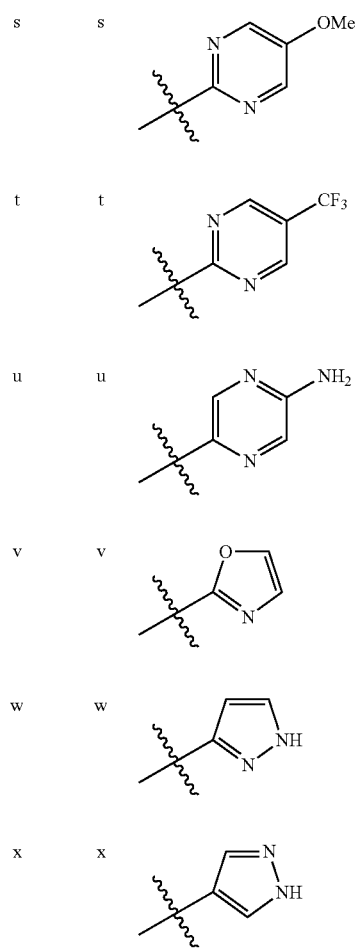

| Ex. 3E | Ex. 3F | R² |
|---|---|---|
| y | y | benzothiophene |
| z | z | 5-methyl-1,2,4-oxadiazole |

Table 3C. Parent Ion m/z (MH)⁺ Data for Compounds

For 3Ea: 3-(1-{[3,5-bis(trifluoromethyl)-1,1':2',1''-terphenyl-4'-yl]carbonyl}pyrrolidin-3-yl)pyridine: m/z (ES)=541 (MH)⁺

For 3Eb: 3-(1-{[3''-fluoro-3,5-bis(trifluoromethyl)-1,1':2',1''-terphenyl-4'-yl]carbonyl}pyrrolidin-3-yl)pyridine: m/z (ES)=559 (MH)⁺

For 3Ec: 3-(1-{[4''-fluoro-3,5-bis(trifluoromethyl)-1,1':2',1''-terphenyl-4'-yl]carbonyl}pyrrolidin-3-yl)pyridine: m/z (ES)=559 (MH)⁺

For 3Ed: 3-(1-{[4''-(trifluoromethoxy)-3,5-bis(trifluoromethyl)-1,1':2',1''-terphenyl-4'-yl]carbonyl}pyrrolidin-3-yl)pyridine: m/z (ES)=625 (MH)⁺

For 3Ee: 3-(1-{[2-pyridin-3-yl-3',5'-bis(trifluoromethyl)biphenyl-4-yl]carbonyl}pyrrolidin-3-yl)pyridine: m/z (ES)=542 (MH)⁺

For 3Ef: 3-(1-{[2-pyridin-4-yl-3',5'-bis(trifluoromethyl)biphenyl-4-yl]carbonyl}pyrrolidin-3-yl)pyridine: m/z (ES)=542 (MH)⁺

For 3Eg: 3-fluoro-5-[4-[(3-pyridin-3-ylpyrrolidin-1-yl)carbonyl]-3',5'-bis(trifluoromethyl)biphenyl-2-yl]pyridine: m/z (ES)=560 (MH)⁺

For 3Eh: 5-[4-[(3-pyridin-3-ylpyrrolidin-1-yl)carbonyl]-3',5'-bis(trifluoromethyl)biphenyl-2-yl]nicotinonitrile: m/z (ES)=567 (MH)⁺

For 3Ei: 5-[4-[(3-pyridin-3-ylpyrrolidin-1-yl)carbonyl]-3',5'-bis(trifluoromethyl)biphenyl-2-yl]pyridine-2-carbonitrile: m/z (ES)=567 (MH)+

For 3Ej: 2-methoxy-5-[4-[(3-pyridin-3-ylpyrrolidin-1-yl)carbonyl]-3',5'-bis(trifluoromethyl)biphenyl-2-yl]pyridine: m/z (ES)=572 (MH)+

For 3Ek: 5-[4-[(3-pyridin-3-ylpyrrolidin-1-yl)carbonyl]-3',5'-bis(trifluoromethyl)biphenyl-2-yl]pyridin-2-amine: m/z (ES)=557 (MH)+

For 3El: 2-methoxy-3-[4-[(3-pyridin-3-ylpyrrolidin-1-yl)carbonyl]-3',5'-bis(trifluoromethyl)biphenyl-2-yl]pyridine: m/z (ES)=572 (MH)+

For 3Em: 2-[4-[(3-pyridin-3-ylpyrrolidin-1-yl)carbonyl]-3',5'-bis(trifluoromethyl)biphenyl-2-yl]pyridine: m/z (ES)=542 (MH)+

For 3En: 3-(1-{[4''-(2,2,2-trifluoroethoxy)-3,5-bis(trifluoromethyl)-1,1':2',1''-terphenyl-4'-yl]carbonyl}pyrrolidin-3-yl)pyridine: m/z (ES)=639 (MH)+

For 3Eo: 5-[4-[(3-pyridin-3-ylpyrrolidin-1-yl)carbonyl]-3',5'-bis(trifluoromethyl)biphenyl-2-yl]-2-(2,2,2-trifluoroethoxy)pyridine: m/z (ES)=640 (MH)+

For 3Ep: 2-(cyclopropylmethoxy)-5-[4-[(3-pyridin-3-ylpyrrolidin-1-yl)carbonyl]-3',5'-bis(trifluoromethyl)biphenyl-2-yl]pyridine: m/z (ES)=612 (MH)+

For 3Eq: 5-[4-[(3-pyridin-3-ylpyrrolidin-1-yl)carbonyl]-3',5'-bis(trifluoromethyl)biphenyl-2-yl]pyrimidine: m/z (ES)=543 (MH)+

For 3Er: 5-[4-[(3-pyridin-3-ylpyrrolidin-1-yl)carbonyl]-3',5'-bis(trifluoromethyl)biphenyl-2-yl]pyrimidine-2-amine: m/z (ES)=558 (MH)+

For 3Es: 5-methoxy-2-[4-[(3-pyridin-3-ylpyrrolidin-1-yl)carbonyl]-3',5'-bis(trifluoromethyl)biphenyl-2-yl]pyrimidine: m/z (ES)=573 (MH)+

For 3Et: 2-[4-[(3-pyridin-3-ylpyrrolidin-1-yl)carbonyl]-3',5'-bis(trifluoromethyl)biphenyl-2-yl]-5-(trifluoromethyl)pyrimidine: m/z (ES)=611 (MH)+

For 3Eu: 5-[4-[(3-pyridin-3-ylpyrrolidin-1-yl)carbonyl]-3',5'-bis(trifluoromethyl)biphenyl-2-yl]pyrazin-2-amine: m/z (ES)=558 (MH)+

For 3Ev: 3-(1-{[2-(1,3-oxazol-2-yl)-3',5'-bis(trifluoromethyl)biphenyl-4-yl]carbonyl}pyrrolidin-3-yl)pyridine: m/z (ES)=532 (MH)+

For 3Ew: 3-(1-{[2-(1H-pyrazol-3-yl)-3',5'-bis(trifluoromethyl)biphenyl-4-yl]carbonyl}pyrrolidin-3-yl)pyridine: m/z (ES)=531 (MH)+

For 3Ex: 3-(1-{[2-(1H-pyrazol-4-yl)-3',5'-bis(trifluoromethyl)biphenyl-4-yl]carbonyl}pyrrolidin-3-yl)pyridine: m/z (ES)=531 (MH)+

For 3Ey: 3-(1-{[2-(1-benzothien-2-yl)-3',5'-bis(trifluoromethyl)biphenyl-4-yl]carbonyl}pyrrolidin-3-yl)pyridine: m/z (ES)=597 (MH)+

For 3Ez: 3-(1-{[2-(5-methyl-1,2,4-oxadiazol-3-yl)-3',5'-bis(trifluoromethyl)biphenyl-4-yl]carbonyl}pyrrolidin-3-yl)pyridine: m/z (ES)=547 (MH)+

(Compound 3Ez was prepared as a single enantiomer, for which the absolute stereochemistry was not determined, substituting i-23e for i-5d.)

For 3Fe: 3-pyridin-3-yl-1-{[2-pyridin-3-yl-3',5'-bis(trifluoromethyl)biphenyl-4-yl]carbonyl}pyrrolidin-3-ol: m/z (ES)=558 (MH)+

For 3Fq: 3-pyridin-3-yl-1-{[2-pyrimidin-5-yl-3',5'-bis(trifluoromethyl)biphenyl-4-yl]carbonyl}pyrrolidin-3-ol: m/z (ES)=559 (MH)+

TABLE 3D

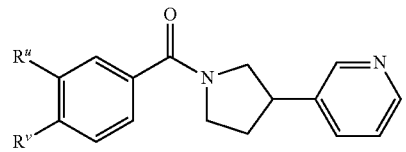

3G

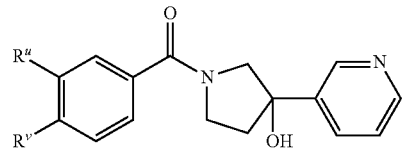

3H $R^u$ and $R^v$ = either $R^2$ or $R^3$ as defined in formula (I), such that only one each of $R^2$ and $R^3$ are present.

| Ex. 3G | Ex. 3H | $R^u$ | $R^v$ |
|---|---|---|---|
| a | a | Ph | Me |
| b | b | 3-F—Ph | Me |
| c | c | CF$_3$ | Ph |
| d | d | Ph | OMe |
| e | e | 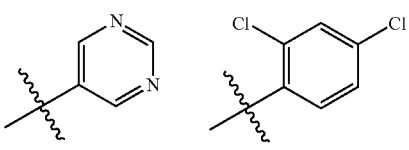 pyrimidin-5-yl | 2,4-dichlorophenyl |
| f | f | pyrimidin-5-yl | 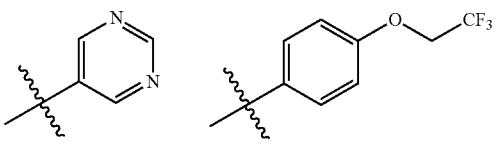 4-(2,2,2-trifluoroethoxy)phenyl |
| g | g | pyrimidin-5-yl | 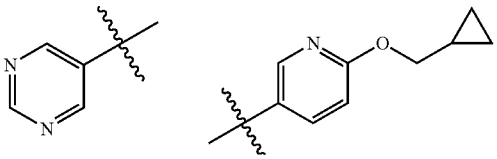 6-(cyclopropylmethoxy)pyridin-3-yl |
| h | h | Ph | 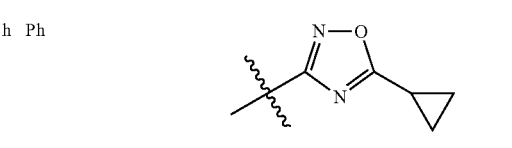 5-cyclopropyl-1,2,4-oxadiazol-3-yl |
| i | i | Ph | 3,5-(Me)$_2$-phenyl |
| j | j | 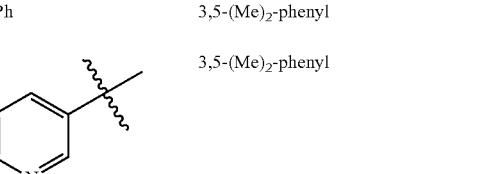 pyridin-3-yl | 3,5-(Me)$_2$-phenyl |
| k | k | 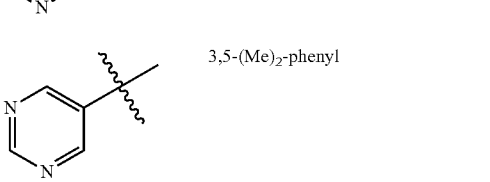 pyrimidin-5-yl | 3,5-(Me)$_2$-phenyl |

TABLE 3D-continued

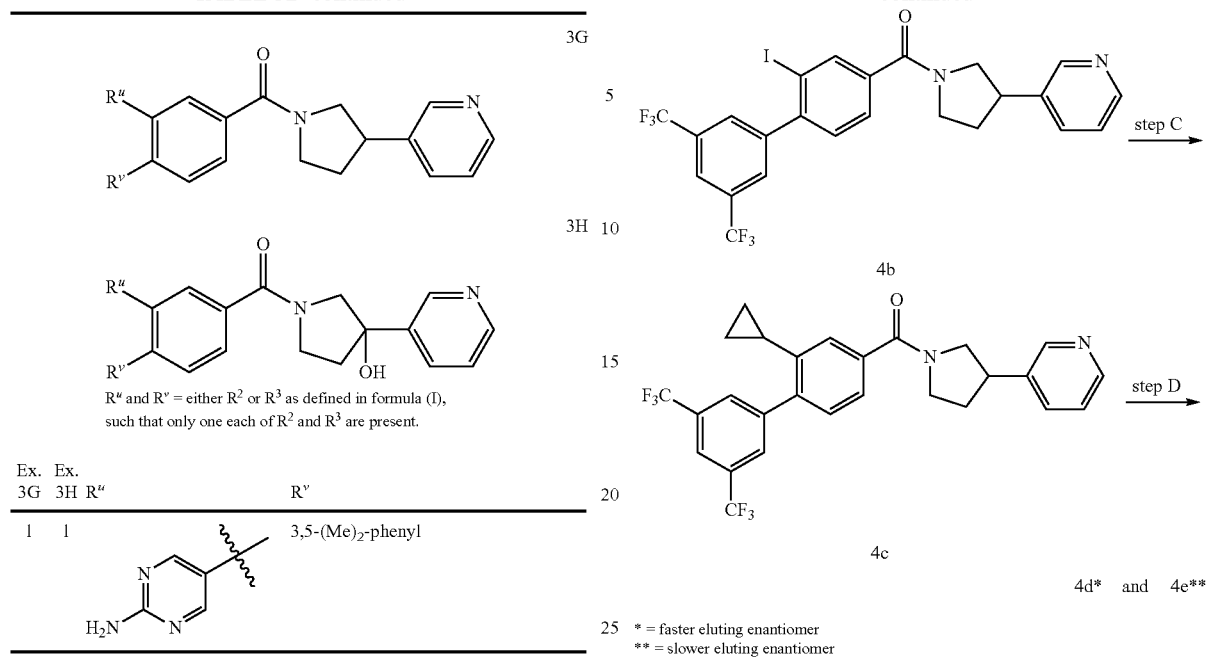

R<sup>u</sup> and R<sup>v</sup> = either R² or R³ as defined in formula (I), such that only one each of R² and R³ are present.

| Ex. 3G | Ex. 3H | R<sup>u</sup> | R<sup>v</sup> |
|---|---|---|---|
| 1 | 1 | 2-amino-pyrimidin-5-yl | 3,5-(Me)₂-phenyl |

Table 3D. Parent Ion m/z (MH)⁺ Data for Compounds

For 3Ga: 3-{1-[(6-methylbiphenyl-3-yl)carbonyl]pyrrolidin-3-yl}pyridine: m/z (ES)=343 (MH)⁺
For 3 Gb: 3-{1-[(3'-fluoro-6-methylbiphenyl-3-yl)carbonyl]pyrrolidin-3-yl}pyridine: m/z (ES)=361 (MH)⁺
For 3Gc: 3-(1-{[2-(trifluoromethyl)biphenyl-4-yl]carbonyl}pyrrolidin-3-yl)pyridine: m/z (ES)=397 (MH)⁺
For 3Gd: 3-{1-[(2-methoxybiphenyl-4-yl)carbonyl]pyrrolidin-3-yl}pyridine: m/z (ES)=359 (MH)⁺
For 3Ge: 5-{2',4'-dichloro-4-[(3-pyridin-3-ylpyrrolidin-1-yl)carbonyl]biphenyl-2-yl}pyrimidine: m/z (ES)=475 (MH)⁺
For 3 Gf: 5-[4-[(3-pyridin-3-ylpyrrolidin-1-yl)carbonyl]-4'-(2,2,2-trifluoroethoxy)biphenyl-2-yl]pyrimidine: m/z (ES)=505 (NIH)⁺
For 3Gg: 5-{2-[6-(cyclopropylmethoxy)pyridin-3-yl]-5-[(3-pyridin-3-ylpyrrolidin-1-yl)carbonyl]phenyl}pyrimidine: m/z (ES)=478 (MH)⁺
For 3Gh: 3-(1-{[6-(5-cyclopropyl-1,2,4-oxadiazol-3-yl)biphenyl-3-yl]carbonyl}pyrrolidin-3-yl)pyridine: m/z (ES)=437 (MH)⁺
For 3Gj: 3-{1-[(3',5'-dimethyl-2-pyridin-3-ylbiphenyl-4-yl)carbonyl]pyrrolidin-3-yl}pyridine: m/z (ES)=434 (MH)⁺
For 3Gk: 5-{3',5'-dimethyl-4-[(3-pyridin-3-ylpyrrolidin-1-yl)carbonyl]biphenyl-2-yl}pyrimidine: m/z (ES)=435 (MH)⁺

EXAMPLE 4

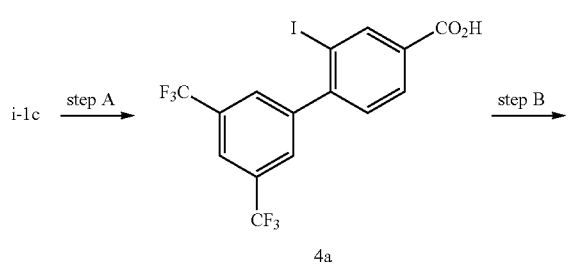

* = faster eluting enantiomer
** = slower eluting enantiomer

Preparation of 4c

Step A: Preparation of 2-iodo-3',5'-bis(trifluoromethyl)biphenyl-4-carboxylic acid (4a)

Compound 4a was prepared following procedures similar to those described for the preparation of compound 3a, substituting i-1c for i-1b, Step B: Preparation of 3-(1-{[2-iodo-3',5'-bis(trifluoromethyl)biphenyl-4-yl]carbonyl}pyrrolidin-3-yl)pyridine (4b)

Compound 4b was prepared following procedures similar to those described for the preparation of compound 3b, substituting 4a for 3a. m/z (ES) 591 (MH)⁺.

Step C: Preparation of 3-(1-{[2-cyclopropyl-3',5'-bis(trifluoromethyl)biphenyl-4-yl]carbonyl}pyrrolidin-3-yl)pyridine (4c)

Palladium acetate (8.00 mg, 0.036 mmol) was added to a solution of 4b (210 mg, 0.356 mmol), cyclopropylboronic acid (36.7 mg, 0.427 mmol), tricyclohexylphosphine (20.0 mg, 0.071 mmol) and potassium phosphate tribasic (227 mg, 1.07 mmol) in toluene:water (3.15 mL of an 20:1 mixture, respectively) at rt. The resulting solution was heated to 100° C. After approximately 24 h, the reaction was cooled to rt, diluted with EtOAc and filtered through a short column of Celite®, eluting with EtOAc. The resulting crude residue was purified by column chromatography on silica gel (gradient elution; 0%-1% methanol/EtOAc as eluent) to afford the title compound 4c. m/z (ES) 505 (MH)⁺.

Step D: Preparation of (4d) and (4e)

Enantiomers 4d and 4e were separated using preparative normal phase chiral HPLC. A solution of 1a in MeOH was injected onto a CHIRALCEL® OD-H (available from Chiral Technologies, Inc., Exton, Pa.) semi-preparative (250×20 mm) HPLC column (eluting with 20% $^i$PrOH/CO$_2$ with a column temperature of 40° C. at 50 mL/min with UV detection at 220 nm). The enantiomers were separated with the faster eluting enantiomer 4d having a retention time of 8.63 min and the slower eluting enantiomer 4e having a retention time of 9.59 min. The separated fractions were concentrated to provide the enantiomers 4d and 4e. For 4e: m/z (ES) 505 (MH)$^+$.

Following procedures as described above in Example 4, the following compounds in Table 4 can be prepared:

TABLE 4

4A

4B

4C $R^u$ and $R^v$ = either $R^2$ or $R^3$ as defined in formula (I), such that only one of each $R^2$ and $R^3$ are present.

| Ex. 4A | Ex. 4B | Ex. 4C | $R^u$ | $R^v$ |
|--------|--------|--------|-------|-------|
| —      | a      | a      | $^c$Pr | 3,5-(CF$_3$)$_2$-phenyl |
| b      | b      | b      | $^c$Pr | Ph |
| c      | c      | c      | Ph    | $^c$Pr |

Table 4. Parent Ion m/z (MH)$^+$ Data for Compounds

For 4Ab: 3-{1-[(2-cyclopropylbiphenyl-4-yl)carbonyl]pyrrolidin-3-yl}pyridine: m/z (ES)=369 (MH)$^+$ For 4Ac: 3-{1-[(6-cyclopropylbiphenyl-3-yl)carbonyl]pyrrolidin-3-yl}pyridine: m/z (ES)=369 (MH)$^+$ For 4Ba: 1-{[2-cyclopropyl-3',5'-bis(trifluoromethyl)biphenyl-4-yl]carbonyl}-3-pyridin-3-ylpyrrolidin-3-ol: m/z (ES)=521 (MH)$^+$ For 4Ca: 2-(1-{[2-cyclopropyl-3',5'-bis(trifluoromethyl)biphenyl-4-yl]carbonyl}pyrrolidin-3-yl)-5-methyl-1,3,4-oxadiazole: m/z (ES)=510 (MH)$^+$

EXAMPLE 5

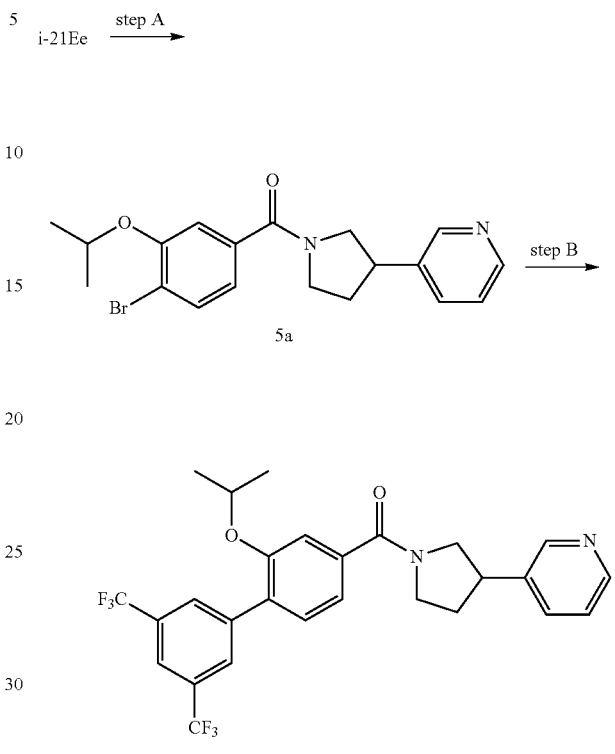

Preparation of 5b

Step A: Preparation of 3-[1-(4-bromo-3-isopropoxybenzoyl)pyrrolidin-3-yl]pyridine (5a)

2-Iodopropane was added to a stirred solution of i-21Ee (144 mg, 0.415 mmol) and cesium carbonate (162 mg, 0.498 mmol) in DMF (2.00 mL), and the resulting mixture was heated to 50° C. After 2 h, the reaction mixture was cooled to rt and partitioned between EtOAc and water. The organics were washed with water and brine, dried (sodium sulfate) and concentrated in vacuo to afford the title compound 5a. m/z (ES) 389 (MH)$^+$.

Step B: Preparation of 3-(1-{[2-isopropoxy-3',5'-bis(trifluoromethyl)biphenyl-4-yl]carbonyl}pyrrolidin-3-yl)pyridine (5b)

Compound 5b was prepared following procedures similar to those described for the preparation of compound 1a, substituting 5a for i-21a. m/z (ES) 523 (MH)$^+$.

Following procedures as described above in Example 5, the following compounds in Table 5 can be prepared:

TABLE 5

5A

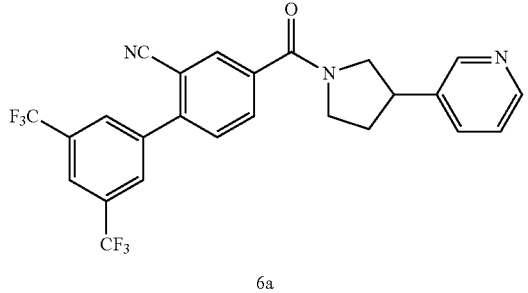

5B

| Ex. 5A | Ex. 5B | R⁹ |
|---|---|---|
| a | a | Me |
| b | b | Et |
| — | c | ᶦPr |
| d | d | Bn |

Table 5, Parent Ion m/z (W)⁺ Data for Compounds

For 5Aa: 3-(1-{[2-methoxy-3',5'-bis(trifluoromethyl)biphenyl-4-yl]carbonyl}pyrrolidin-3-yl)pyridine: m/z (ES)=495 (MH)⁺

For 5Ab: 3-(1-{[2-ethoxy-3',5'-bis(trifluoromethyl)biphenyl-4-yl]carbonyl}pyrrolidin-3-yl)pyridine: m/z (ES)=509 (MH)⁺

For 5Ad: 3-(1-{[2-(benzyloxy)-3',5'-bis(trifluoromethyl)biphenyl-4-yl]carbonyl}pyrrolidin-3-yl)pyridine: m/z (ES)=571 (MH)⁺

EXAMPLE 6

4b —step A→

Step A: Preparation of 4-[(3-pyridin-3-ylpyrrolidin-1-yl)carbonyl]-3',5'-bis(trifluoromethyl)biphenyl-2-carbonitrile (6a)

Copper(I) cyanide (42.9 mg, 0.479 mmol) was added to a stirred solution of 4b (200 mg, 0.368 mmol) in DMSO (4.00 mL), and the resulting mixture was heated to 180° C. for 12 h. The reaction mixture was cooled to rt, quenched with satd. aq. NH₄Cl and extracted with EtOAc. The combined organics were washed with water and brine, dried (sodium sulfate) and concentrated in vacuo. The resulting crude residue was purified by preparative reversed phase HPLC on YMC Pack Pro C18 stationary phase (CH₃CN/H₂O as eluent, 0.05% TFA as modifier), followed by lyophilization of the purified fractions to afford the title compound 6a. m/z (ES) 490 (MH)⁺.

Following procedures as described above in Example 6, the following compounds in Table 6 can be prepared:

TABLE 6

6A

6B

Rᵘ and Rᵛ = either R² or R³ as defined in formula (I), such that only one each of R² and R³ are present.

| Ex. 6A | Ex. 6B | Rᵘ | Rᵛ |
|---|---|---|---|
| — | a | CN | 3,5-(CF₃)₂-phenyl |
| b | b | CN | Ph |
| c | c | Ph | CN |

Table 6. Parent Ion m/z (MH)⁺ Data for Compounds

For 6Ab: 4-[(3-pyridin-3-ylpyrrolidin-1-yl)carbonyl]biphenyl-2-carbonitrile: m/z (ES)=354 (MH)⁺

For 6Ac: 5-[(3-pyridin-3-ylpyrrolidin-1-yl)carbonyl]biphenyl-2-carbonitrile: m/z (ES)=354 (MH)⁺

EXAMPLE 7

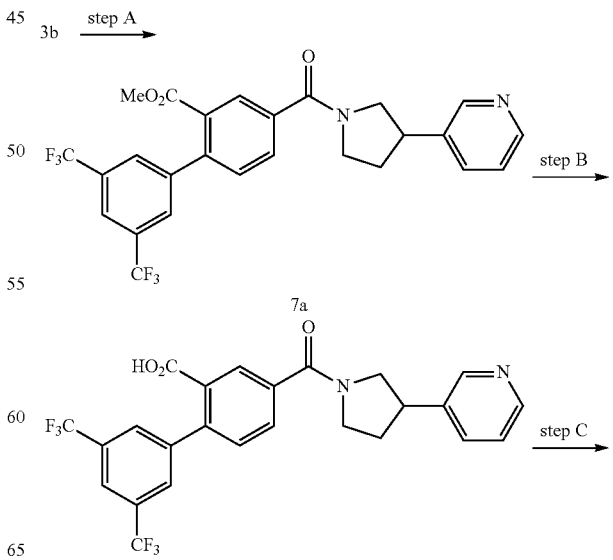

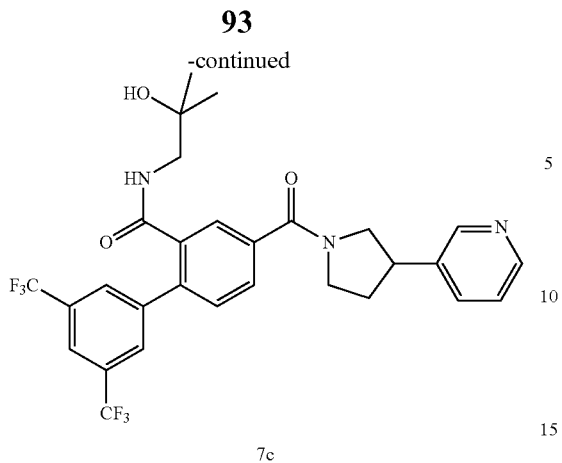

7c

Preparation of 7c

Step A: Preparation of methyl 4-[(3-pyridin-3-ylpyrrolidin-1-yl)carbonyl]-3',5'-bis(trifluoromethyl)biphenyl-2-carboxylate (7a)

Compound 7a was prepared following procedures similar to those described for the preparation of compound i-3d (scheme i-3, step D), substituting 3b for i-3c. m/z (ES) 523 (MH)+.

Step B: Preparation of 4-[(3-pyridin-3-ylpyrrolidin-1-yl)carbonyl]-3',5'-bis(trifluoromethyl)biphenyl-2-carboxylic acid (7b)

Compound 7b was prepared following procedures similar to those described for the preparation of compound 3a (example 3, step A), substituting 7a for i-1b. m/z (ES) 509 (MH)+.

Step C: Preparation of N-(2-hydroxy-2-methylpropyl)-4-[(3-pyridin -3-ylpyrrolidin-1-yl)carbonyl]-3',5'-bis(trifluoromethyl)biphenyl-2-carboxamide (7c)

Compound 7c was prepared following procedures similar to those described for the preparation of compound i-21a (scheme i-21, step A), substituting 7b for 4-iodobenzoic acid. m/z (ES) 580 (MH)+.

Preparation of 7d

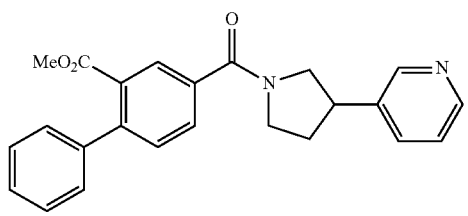

7d

Compound 7d was prepared following procedures described by substituting i-1Ad for i-1b in Example 3, step A and substituting the product of that reaction for 3a in Example 3, step B. The amide product of the aforementioned reaction was substituted for 3b in Example 7, step A to afford compound 7d. m/z (ES) 387 (MH)+.

Following procedures as described above in Example 7, the following compounds in Table 7 can be prepared:

TABLE 7

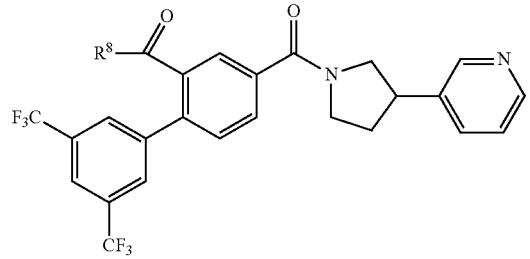

7A

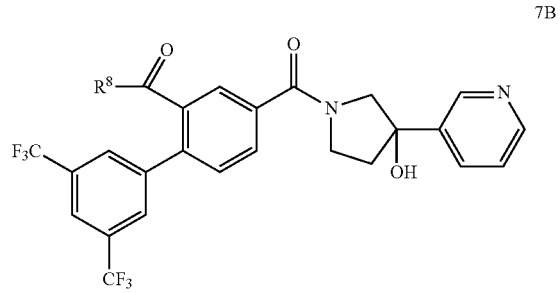

7B

| Ex. 7A | Ex. 7B | R⁸ |
|--------|--------|-----|
| — | a | —OMe |
| — | b | ⟶NH–CH₂–C(CH₃)₂–OH |
| c | c | ⟶NH–cyclopropyl |
| d | d | ⟶NH–CH₂–C(CH₃)₃ |
| e | e | ⟶N-morpholine |

Table 7. Parent Ion m/z (MH)+ Data for Compounds

For 7Ac: N-cyclopropyl-4-[(3-pyridin-3-ylpyrrolidin-1-yl)carbonyl]-3',5'-bis(trifluoromethyl)biphenyl-2-carboxamide: m/z (ES)=548 (MH)+

For 7Ae: 4-{[4-[(3-pyridin-3-ylpyrrolidin-1-yl)carbonyl]-3',5'-bis(trifluoromethyl)biphenyl-2-yl]carbonyl}morpholine: m/z (ES)=578 (MH)+

EXAMPLE 8

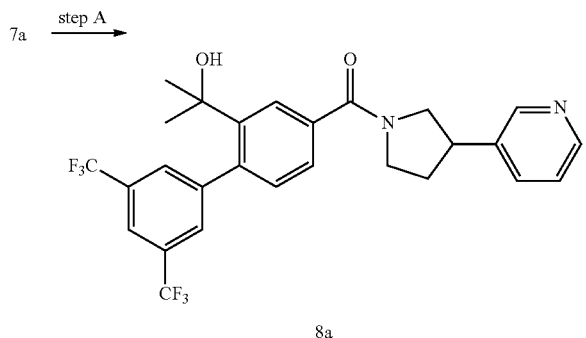

Preparation of 2-[4-[(3-pyridin-3-ylpyrrolidin-1-yl)carbonyl]-3',5'-bis(trifluoromethyl)biphenyl-2-yl]propan-2-ol (8a)

7a (50.0 mg in 500 μL THF, 0.096 mmol) was added to a stirred solution of lithium chloride (28.4 mg, 0.670 mmol) and methylmagnesium bromide (480 μL of a 1.4 M (75:25) toluene:THF solution, 0.670 mmol) at 0° C. After 2 h, the reaction mixture was quenched with said. aq. NH$_4$Cl and extracted with EtOAc. The combined organics were washed with brine, dried (sodium sulfate) and concentrated in vacuo. The resulting crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 8a. m/z (ES) 523 (MH)$^+$.

EXAMPLE 9

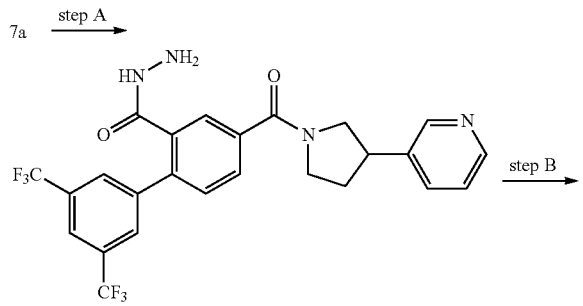

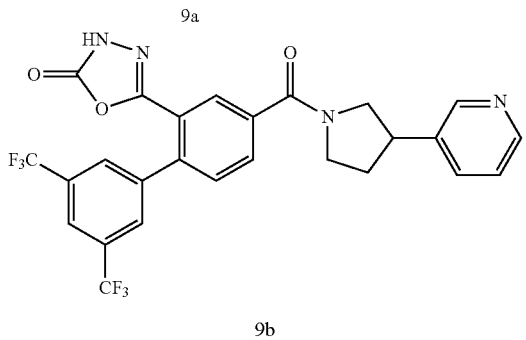

Preparation of 9b

Step A: Preparation of 4-[(3-pyridin-3-ylpyrrolidin-1-yl)carbonyl]-3',5'-bis(trifluoromethyl)biphenyl-2-carbohydrazide (9a)

A solution of 7a (160 mg, 0.300 mmol) and hydrazine hydrate (286 μL, 9.18 mmol) in ethanol:toluene (2.70 mL of an 8:1 mixture, respectively) was heated to 100° C. in a sealed microwave vial for 10 min, An additional aliquot of hydrazine hydrate (200 μL, 6.42 mmol) was added, and the resulting mixture was heated to 135° C. in a sealed microwave vial for 15 min. The reaction mixture was cooled to rt and partitioned between EtOAc and water. The combined organics were washed with water and brine, dried (sodium sulfate) and concentrated in vacuo to afford the title compound 9a. m/z (ES) 523 (MH)$^+$.

Step B: Preparation of 5-[4-[(3-pyridin-3-ylpyrrolidin-1-yl)carbonyl]-3',5'-bis(trifluoromethyl)biphenyl-2-yl]-1,3,4-oxadiazol-2(3H)-one Phosgene (284 μL of a 1.89 M toluene solution, 0.537 mmol) was added dropwise to a stirred solution of 9a (140 mg, 0.268 mmol) in DCM (2.50 mL) at −78° C. After 2 h, the reaction mixture was quenched with said. aq. NaHCO$_3$ and extracted with EtOAc. The combined organics were washed with brine, dried (sodium sulfate) and concentrated in vacuo. The resulting crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 9b. m/z (ES) 549 (MH)$^+$.

EXAMPLE 10

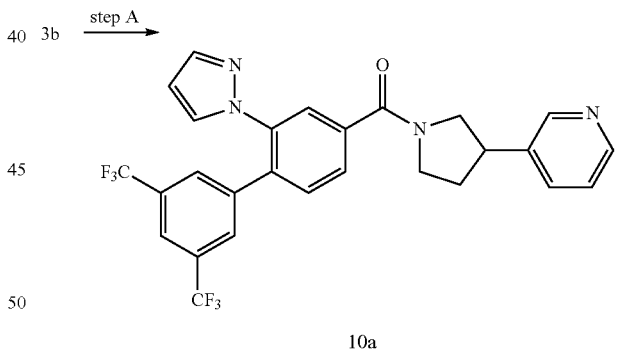

Preparation of 10a

Step A: Preparation of 3-(1-{[2-(1H-pyrazol-1-yl)-3',5'-bis(trifluoromethyl)biphenyl-4-yl]carbonyl}pyrrolidin-3-yl)pyridine (10a)

A solution of 3b (54.0 mg, 0.099 mmol), pyrazole (50.7 mg, 0.745 mmol), salicylaldoxime (19.8 mg, 0.145 mmol), copper(I) oxide (16.6 mg, 0.116 mmol) and cesium carbonate (265 mg, 0.812 mmol) in acetonitrile (1.00 mL) was heated to 120° C. in a sealed microwave vial for a total of 60 min. The reaction mixture was cooled to rt, concentrated in vacuo, and the resulting crude residue was purified by preparative reversed phase HPLC on YMC Pack Pro C18 stationary phase (CH₃CN/H₂O as eluent, 0.05% TFA as modifier), followed by lyophilization of the purified fractions to afford the title compound 10a. m/z (ES) 531 (MH)⁺.

EXAMPLE 11

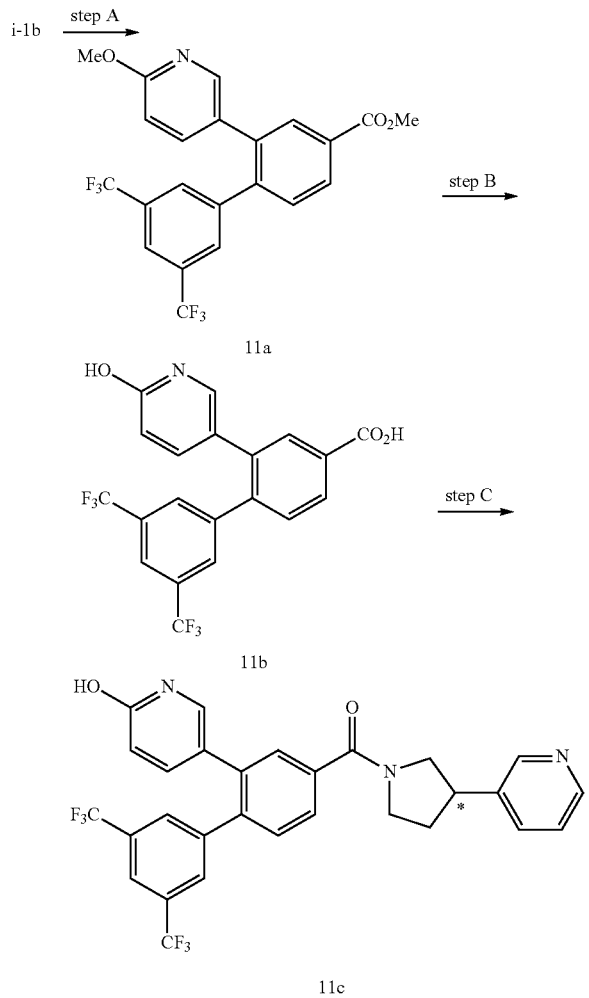

* = enantiomerically pure stereocenter for which the absolute stereochemistry was not determined Preparation of 11c Step A: Preparation of methyl 2-(6-methoxypyridin-3-yl)-3',5'-bis(trifluoromethyl)biphenyl-4-carboxylate (11a)

Compound 11a was prepared following procedures similar to those described in Example 1, step A, substituting i-1b for i-21a. m/z (ES) 456 (MH)⁺.

Step B: Preparation of 2-(6-hydroxypyridin-3-yl)-3',5'-bis(trifluoromethyl)biphenyl-4-carboxylic acid (11b)

A solution of 11a (240 mg, 0.527 mmol) in hydrobromic acid (5.00 mL of a 33 wt. % acetic acid solution) was heated to 60° C. in a sealed tube. After 20 h, the reaction mixture was cooled to rt and was added to said. aq. NaHCO₃. The resulting mixture was extracted with EtOAc, and combined organics were concentrated in vacuo to give a crude residue that was purified by preparative reversed phase HPLC on YMC Pack Pro C18 stationary phase (CH₃CN/H₂O as eluent, 0.05% TFA as modifier), followed by lyophilization of the purified fractions to afford the title compound 11b. m/z (ES) 428 (MH)⁺.

Step C: Preparation of 5-[4-[(3-pyridin-3-ylpyrrolidin-1-yl)carbonyl]-3',5'-bis(trifluoromethyl)biphenyl-2-yl]pyridin-2-ol (11c)

Compound 11c was prepared following procedures similar to those described in Example 3, step B, substituting 11b for 3a and i-23e for i-5d. m/z (ES) 558 (MH)⁺.

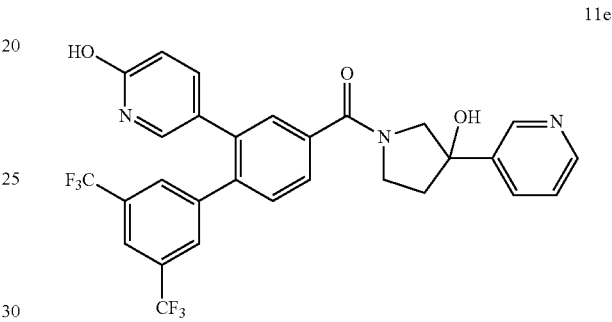

Compound 11e was prepared following procedures similar to those described in Example 3, step B, substituting 11b for 3a and i-6c for i-5d, respectively. m/z (ES) 574 (MH)⁺.

PAF Binding Assay

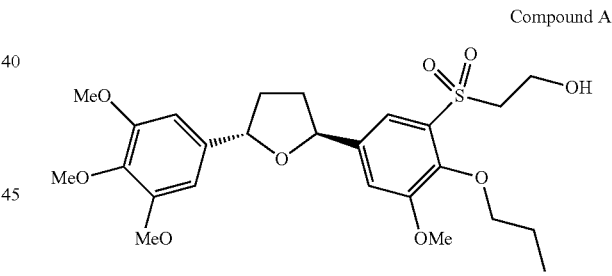

PAFR was derived from membranes from CHO cells overexpressing the full-length human PAFR. Supernatant from the cell homogenate pellet (3000×g) is pelleted (35000×g), and the resulting pellet is resuspended in a Tris HCl buffer (50 mM Tris HCl pH 7.4, 5 mM MgCl₂, 30% glycerol) to afford a parent PAFR stock that is diluted in PAF binding buffer (50 mM HEPES pH 7.0, 10 mM MgCl₂, 5 mM CaCl₂, 5 mM D-(+)glucose, 0.25% fatty-acid free BSA) to afford a PAFR assay stock (120 µg/mL) prior to each use.

Binding buffer (48 µL) and competitor compound (i.e., the compound to be tested) in DMSO (2 µL) were added to a 96-well plate. Cold PAF C-18 (200 nM final concentration) was used to determine non-specific binding. 25000 cpm of ³H-PAF (25 µL, of a stock solution in PAF binding buffer) was added to all wells, and the plates sealed and shaken at rt for 5 min. PAFR assay stock (3 µg/well) was added, and the plate was sealed and shaken at rt for 2 h. SPA beads[1] (10 µL of a 25 mg/mL suspension in binding buffer) were added to all wells, and the plates were sealed and shaken for 30 min. The plates were centrifuged (1900 rpm for 5 min.), allowed to stand for 30 min. and read on a Microbeta TriLux counter.

Specific binding is defined as total binding minus non-specific binding. Total binding was the amount of $^3$H-PAF bound to SPA beads in the absence of competitor; non-specific binding was $^3$H-PAF bound in the presence of 30 µM Compound A.[2] The $IC_{50}$ values were obtained by computer analysis of the experimental data.[3] Percent inhibition was calculated as 100−[(Sample−Non-specific bound)/(Total bound−Non-specific bound)×100].

Most of the representative tested compounds of this invention were determined to have an $IC_{50}$<500 nM. Preferred compounds had an $IC_{50} \leq 85$ nM, and most preferred compounds had an $IC_{50} \leq 15$ nM.

REFERENCES: 1. Wheat Germ Agglutinin (WGA) PVT SPA Scintillation Beads; GE Healthcare. 2. Hwang, S. B., et al. *J. Lipid Mediat.* 1993, 7, 115-134. 3. Kinetic, EBDA, Ligand, Lowry. A collection of Radioligand Binding Analysis Programs by G. A. MacPherson. Elsevier-BIOSOFT.

What is claimed is:

1. A compound having structural Formula I:

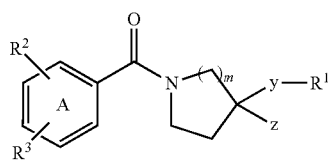

I and the pharmaceutically acceptable salts thereof wherein:
$R^1$ is selected from the group consisting of:
  (a) 5-membered heterocyclic ring containing 1 to 4 heteroatoms selected from 1 to 4 of N, zero to 1 of O, and zero to 1 of S, optionally substituted with $R^7$, and
  (b) pyridyl, optionally substituted with $R^7$;
$R^2$ is selected from the group consisting of:
  (a) —H,
  (b) chloro,
  (c) fluoro,
  (d) —$C_{1-6}$alkyl optionally substituted with one or more substituents selected from the group consisting of (i) hydroxy, (ii) methoxy, (iii) fluoro,
    (iv) phenyl optionally substituted with one or more substituents selected from the group consisting of —F, —Cl, —OH, —$OC_{1-4}$alkyl optionally substituted with fluoro, and —$C_{1-4}$alkyl optionally substituted with fluoro,
    (v) 5-membered heterocyclic ring containing 1 to 4 heteroatoms selected from 1 to 4 of N, zero to 1 of O, and zero to 1 of S, optionally substituted with $R^5$, and
    (vi) 6-membered heterocyclic ring containing 1 to 2 of N, optionally substituted with $R^5$,
  (e) —$C_{3-6}$cycloalkyl optionally substituted with one or more substituents selected from the group consisting of fluoro, hydroxy, and methoxy,
  (f) phenyl optionally substituted with $R^{5a}$,
  (g) 5-membered heterocyclic ring containing 1 to 4 heteroatoms selected from 1 to 4 of N, zero to 1 of O, and zero to 1 of S, optionally substituted with $R^5$,
  (h) 6-membered heterocyclic ring containing 1 to 2 of N, optionally substituted with $R^5$,
  (i) 9-membered ortho-fused bicyclic heterocyclic ring system containing 1 to 4 heteroatoms selected from 1 to 4 of N and 1 to 2 of O, optionally substituted with one to three of $R^5$,
  (j) 10-membered ortho-fused bicyclic heterocyclic ring system containing 1 to 4 of N, optionally substituted with one to three of $R^5$,
  (k) cyano,
  (l) —$CO_2R^8$,
  (m) —$OR^9$,
  (n) —(CO)$NR^{10}R^{11}$,
  (o) —$NR^{10}R^{11}$,
  (p) —NHC(O)$R^8$,
  (q) —$NHSO_2R^{12}$,
  (r) —NHC(O)$OR^{12}$, and
  (s) —NHC(O)$NR^{10}R^{11}$;
$R^3$ is selected from the group consisting of
  (a) phenyl substituted with one to three of $R^4$,
  (b) 5-membered heterocyclic ring containing 1 to 4 heteroatoms selected from 1 to 4 of N, zero to 1 of O, and zero to 1 of S, substituted with one to three of $R^4$,
  (c) 6-membered heterocyclic ring containing 1 to 2 of N, substituted with one to three of $R^4$,
  (d) 9-membered ortho-fused bicyclic heterocyclic ring containing 1 to 4 heteroatoms selected from 1 to 4 of N and 1 to 2 of O, substituted with one to three of $R^4$, and
  (e) 10-membered ortho-fused bicyclic heterocyclic ring containing 1 to 4 of N, substituted with one to three of $R^4$;
$R^4$ is independently selected at each occurrence from the group consisting of
  (a) —H,
  (b) fluoro,
  (c) chloro,
  (d) 5-membered heterocyclic ring containing 1 to 4 heteroatoms selected from 1 to 4 of N, zero to 1 of O, and zero to 1 of S, optionally substituted with —OH, —$NH_2$, —$CH_3$ or —$CF_3$,
  (e) —$OC_{1-6}$alkyl optionally substituted with —$C_{3-6}$cycloalkyl or one or more of fluoro,
  (f) —$C_{1-6}$alkyl optionally substituted with one or more substituents selected from the group consisting of —$C_{3-6}$cycloalkyl, methoxy, —$OCF_3$, hydroxy and fluoro,
  (g) —$NR^{10}R^{11}$,
  (h) —$C_{3-6}$cycloalkyl optionally substituted with one of more of fluoro,
  (i) —CN, and
  (j) —OH;
$R^5$ is independently selected at each occurrence from the group consisting of —F, —Cl, hydroxy, cyano, oxo, —$C_{1-4}$alkyl optionally substituted with fluoro, —$NR^{10}R^{11}$, —$CO_2R^8$, —$SO_2R^{10}R^{11}$, —$CONR^{10}R^{11}$, —$OC_{1-6}$alkyl optionally substituted with —$C_{3-6}$cycloalkyl or fluoro, and —$C_{3-6}$cycloalkyl optionally substituted with one or more substituents selected from the group consisting of —F, —OH, —$OCH_3$, and —$OCF_3$;
$R^{5a}$ is independently selected at each occurrence from the group consisting of —F, —Cl, hydroxy, cyano, —$NR^{10}R^{11}$, —$C_{1-4}$alkyl optionally substituted with fluoro, —$CONR^{10}R^{11}$, —$OC_{1-6}$alkyl optionally substituted with —$C_{3-6}$cycloalkyl or fluoro, and —$C_{3-6}$cycloalkyl optionally substituted with one or more substituents selected from the group consisting of —F, —OH, —$OCH_3$, and —$OCF_3$;

$R^7$ is selected independently at each occurrence from the group consisting of —F, —Cl, hydroxy, cyano, oxo, amino, —$C_{1-6}$alkyl optionally substituted with fluoro, —$C_{3-6}$cycloalkyl optionally substituted with fluoro, and —$OC_{1-6}$alkyl optionally substituted with fluoro;

$R^8$ is independently selected at each occurrence from the group consisting of —H, —$C_{1-6}$alkyl optionally substituted with phenyl, phenyl optionally substituted with $R^{5a}$, and —$C_{3-6}$cycloalkyl;

$R^9$ is selected from the group consisting of:
 (a) —H,
 (b) —$C_{1-4}$alkyl optionally substituted with one or more substituents selected from the group consisting of (i) hydroxy, (ii) fluoro, (iii) phenyl optionally substituted with one or more substituents selected from the group consisting of —F, —Cl, —$OCH_3$, —$CF_3$ and —$OCF_3$, and
 (c) —$C_{3-6}$cycloalkyl optionally substituted with one or more substituents selected from the group consisting of fluoro, hydroxy, and —$C_{1-4}$alkyl optionally substituted with fluoro;

$R^{10}$ and $R^{11}$ are each independently selected at each occurrence from the group consisting of
 (a) —H,
 (b) —$C_{1-6}$alkyl optionally substituted with one or more substituents selected from the group consisting of (i) hydroxy, (ii) fluoro, (iii) phenyl optionally substituted with one or more substituents selected from the group consisting of —F, —Cl, —$OCH_3$, —$CF_3$ and —$OCF_3$, and
 (c) —$C_{3-6}$cycloalkyl optionally substituted with one or more substituents selected from the group consisting of fluoro, hydroxy, and —$C_{1-4}$alkyl optionally substituted with fluoro;

or $R^{10}$ and $R^{11}$ together with the nitrogen to which they are both attached represent a ring selected from the group consisting of azetidinyl, pyrrolidinyl, piperidinyl, piperazinyl and morpholinyl, wherein the ring is optionally substituted with a substituent selected from the group consisting of —$CH_3$, —$CF_3$, —F and —OH;

$R^{12}$ is independently selected at each occurrence from the group consisting of
 (a) —$C_{1-4}$alkyl optionally substituted with one or more substituents selected from the group consisting of (i) fluoro, (ii) cyano, (iii) hydroxy, (iv) —$OCH_3$ and (v) —$OCF_3$, and
 (b) phenyl optionally substituted with one or more of $R^{5a}$;

m is the integer 1 (one);
y is a bond;
z is selected from the group consisting of —H, fluoro, hydroxy, and —$C_{1-4}$alkyl optionally substituted with one or more substituents selected from —OH and —F; and $R^{6a}$ and $R^{6b}$ are independently selected at each occurrence from the group consisting of —H, hydroxy, —OC(O)$C_{1-4}$-alkyl, and —$OC_{1-4}$alkyl optionally substituted with one or more of fluoro;

or $R^{6a}$ and $R^{6b}$ are joined together with the carbon to which they are both attached to form a —$C_{3-6}$cycloalk-diyl ring.

2. The compound of claim 1 wherein $R^1$ is selected from the group consisting of pyridyl, oxadiazolyl, tetrazolyl, triazolyl, pyrazolyl, thiazolyl and isoxazolyl, each of which is optionally substituted with $R^7$.

3. The compound of claim 2 wherein $R^1$ is selected from pyridyl optionally mono-substituted with $R^7$, and oxadiazolyl optionally mono-substituted with $R^7$.

4. The compound of claim 3 wherein $R^1$ is unsubstituted pyridyl.

5. The compound of claim 3 wherein $R^3$ is selected from the group consisting of phenyl, pyridinyl, pyridazinyl, pyrimidinyl, pyrazinyl, pyrazolyl, imidazolyl, quinolinyl, isoquinolinyl, indolyl, benzofuranyl, and benzodioxolyl, each of which is optionally substituted with one to three of $R^4$.

6. The compound of claim 1 wherein $R^2$ is selected from the group consisting of:
 (a) phenyl optionally substituted with $R^{5a}$,
 (b) 5-membered heterocyclic ring containing 1 to 4 heteroatoms selected from 1 to 4 of N, zero to 1 of O, and zero to 1 of S, optionally substituted with $R^5$,
 (c) 6-membered heterocyclic ring containing 1 to 2 of N, optionally substituted with $R^5$,
 (d) 9-membered ortho-fused bicyclic heterocyclic ring system containing 3 to 4 of N, optionally substituted with one to three of $R^5$,
 (e) 10-membered ortho-fused bicyclic heterocyclic ring system containing 1 to 4 of N, optionally substituted with one to three of $R^5$,
 (f) —$C_{1-6}$alkyl substituted with a substituent selected from the group consisting of
  (i) phenyl optionally substituted with one or more substituents selected from the group consisting of —F, —Cl, —OH, —$C_{1-4}$alkyl optionally substituted with one or more of fluoro, and —$OC_{1-4}$alkyl optionally substituted with one or more of fluoro, and
  (ii) a 5-membered heterocyclic ring containing 1 to 4 heteroatoms selected from 1 to 4 of N, zero to 1 of O, and zero to 1 of S, optionally substituted with $R^5$, and
  (iii) 6-membered heterocyclic ring containing 1 to 2 of N, optionally substituted with $R^5$,
 (g) cyano, (h) —$CO_2R^8$, (i) —$OR^9$, (j) —(CO)$NR^{10}R^{11}$, (k) —$NR^{10}R^{11}$, (l) —NHC(O)$R^8$, (m) —$NHSO_2R^{12}$, (n) —NHC(O)$OR^{12}$ and (o) —NHC(O)$NR^{10}R^{11}$.

7. The compound of claim 6 wherein $R^2$ is selected from the group consisting of:
 (a) phenyl optionally substituted with $R^{5a}$,
 (b) 5-membered heterocyclic ring containing 1 to 4 heteroatoms selected from 1 to 4 of N, zero to 1 of O, and zero to 1 of S, optionally substituted with $R^5$,
 (c) 6-membered heterocyclic ring containing 1 to 2 of N, optionally substituted with $R^5$,
 (d) 9-membered ortho-fused bicyclic heterocyclic ring system containing 3 to 4 of N, optionally substituted with one to three of $R^5$, and
 (e) 10-membered ortho-fused bicyclic heterocyclic ring system containing 1 to 4 of N, optionally substituted with one to three of $R^5$.

8. The compound of claim 6 wherein $R^2$ is selected from the group consisting of: cyano, —$CO_2R^8$, —$OR^9$, —(CO)$NR^{10}R^{11}$, —$NR^{10}R^{11}$, —NHC(O)$R^8$, —$NHSO_2R^{12}$, —NHC(O)$OR^{12}$ and —NHC(O)$NR^{10}R^{11}$.

9. The compound of claim 1 wherein $R^3$ is phenyl substituted with one to three of $R^4$ and is attached to ring "A" at the 4-position:

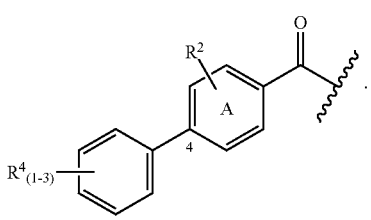

10. The compound of claim 9 wherein $R^2$ is attached to ring "A" at the 3-position, and $R^4$ is attached to ring "B" at the 3- and 5-positions:

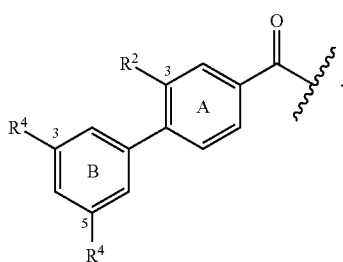

11. The compound of claim 10 having structural Formula IV:

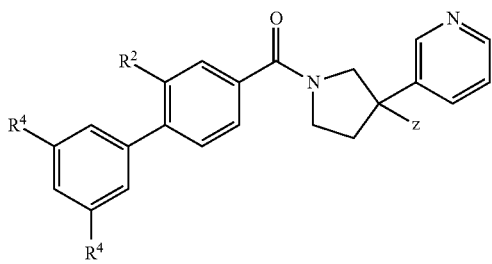

and pharmaceutically acceptable salts thereof.

12. The compound of claim 11 wherein:
z is selected from the group consisting of —H, —F and —OH;
$R^2$ is selected from the group consisting of (a) a heterocyclic ring selected from the group consisting of pyridyl, imidizolyl, pyrimidyl and pyrazinyl, wherein the heterocyclic ring is optionally substituted with a substituent selected from the group consisting of —NH$_2$, —OCH$_3$, —OH, —CN and —F; (b) —OCF$_3$, (c) cyclopropyl and (d) —H; and
$R^4$ is selected from the group consisting of —CH$_3$, CF$_3$ and —OCH$_3$.

13. The compound of claim 1 wherein $R^2$ is selected from the group consisting of:
(a) —H, (b) chloro, (c) fluoro, (d) —C$_{1-6}$alkyl optionally substituted with one or more substituents selected from the group consisting of hydroxy, methoxy, fluoro and chloro, and
(e) —C$_{3-6}$cycloalkyl optionally substituted with one or more substituents selected from the group consisting of hydroxy, methoxy, fluoro and chloro.

14. The compound of claim 1 having structural Formula V

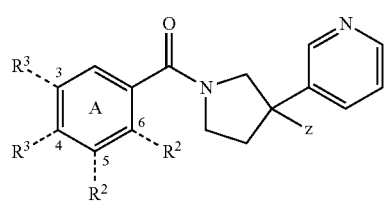

and the pharmaceutically acceptable salts thereof wherein:
z is —H or —OH;
$R^2$ is bonded to the "A" ring phenyl at either the 5- or the 6-position and is selected from the group consisting of —H, —F, —CH$_3$, —CF$_3$, —OCF$_3$, and phenyl optionally substituted with $R^{5a}$; and
$R^3$ is bonded to the "A" ring phenyl at either the 3- or the 4-position and is selected from the group consisting of:
(a) phenyl substituted with one to three of $R^4$,
(b) 5-membered heterocyclic ring containing 1 to 4 heteroatoms selected from 1 to 4 of N, zero to 1 of O, and zero to 1 of S, substituted with one to three of $R^4$,
(c) 6-membered heterocyclic ring containing 1 to 2 of N, substituted with one to three of $R^4$,
(d) 9-membered ortho-fused bicyclic heterocyclic ring containing 1 to 4 heteroatoms selected from 1 to 4 of N and 1 to 2 of O, substituted with one to three of $R^4$, and
(e) 10-membered ortho-fused bicyclic heterocyclic ring containing 1 to 4 of N, substituted with one to three of $R^4$.

15. The compound of claim 14 selected from those wherein:
(a) $R^2$ is —H;
(b) $R^3$ is present at the 4-position of ring A, and $R^2$ at the 6-position of ring A is not —H;
(c) $R^3$ is present at the 4-position of ring A, and the $R^2$ at the 5-position of ring A is not —H; or
(d) $R^3$ is present at the 3-position of ring A, and the $R^2$ at the 5-position of ring A is not —H.

16. The compound of claim 1 selected from the group consisting of:
5-{4-[(3-pyridin-3-ylpyrrolidin-1-yl)carbonyl]phenyl}-2-[(trifluoromethoxy)methyl]pyridine;
2-(cyclopropylmethoxy)-5-{4-[(3-pyridin-3-ylpyrrolidin-1-yl)carbonyl]phenyl}pyridine;
3-[1-({4'-[(trifluoromethoxy)methyl]biphenyl-4-yl}carbonyl)pyrrolidin-3-yl]pyridine;
3-{1-[4-(2,3-dihydro-1-benzofuran-5-yl)benzoyl]pyrrolidin-3-yl}pyridine;
3-{1-[4-(1,3-benzodioxol-5-yl)benzoyl]pyrrolidin-3-yl}pyridine;
3-(1-{[3'-(5-methyl-1,3,4-oxadiazol-2-yl)biphenyl-4-yl]carbonyl}pyrrolidin-3-yl)pyridine;
1-{[3',5'-bis(trifluoromethyl)biphenyl-4-yl]carbonyl}-3-pyridin-3-ylpyrrolidin-3-ol;
3-(1-{[2-(trifluoromethoxy)-3',5'-bis(trifluoromethyl)biphenyl-4-yl]carbonyl}pyrrolidin-3-yl)pyridine;
5-[(3-pyridin-3-ylpyrrolidin-1-yl)carbonyl]biphenyl-2-amine;
3-(1-{[5-(trifluoromethoxy)biphenyl-3-yl]carbonyl}pyrrolidin-3-yl)pyridine;
3-(1-{[3'-fluoro-5-(trifluoromethoxy)biphenyl-3-yl]carbonyl}pyrrolidin-3-yl)pyridine;
6-[3-[(3-pyridin-3-ylpyrrolidin-1-yl)carbonyl]-5-(trifluoromethoxy)phenyl]quinoline;

3-methoxy-5-[4-[(3-pyridin-3-ylpyrrolidin-1-yl)carbo-nyl]-3',5'-bis(trifluoromethyl)biphenyl-2-yl]pyridine;
3-(1-{[3',5'-bis(trifluoromethyl)biphenyl-4-yl]carbonyl}-3-fluoropyrrolidin-3-yl)pyridine;
1-{[3',5'-bis(trifluoromethyl)biphenyl-4-yl]carbonyl}-3-(5-chloropyridin-3-yl)pyrrolidin-3-ol;
1-{[3',5'-bis(trifluoromethyl)biphenyl-4-yl]carbonyl}-3-(5-chloropyridin-3-yl)pyrrolidin-3-ol;
5-(1-{[3',5'-bis(trifluoromethyl)biphenyl-4-yl]carbonyl}-3-hydroxypyrrolidin-3-yl)nicotinonitrile;
1-{[3',5'-bis(trifluoromethyl)biphenyl-4-yl]carbonyl}-3-[5-(trifluoromethyl)pyridin-3-yl]pyrrolidin-3-ol;
1-{[3',5'-bis(trifluoromethyl)biphenyl-4-yl]carbonyl}-3-(6-methoxypyridin-3-yl)pyrrolidin-3-ol;
3-(1-{[3,5-bis(trifluoromethyl)-1,1':2',1''-terphenyl-4'-yl]carbonyl}pyrrolidin-3-yl)pyridine;
3-(1-{[3''-fluoro-3,5-bis(trifluoromethyl)-1,1':2',1''-terphenyl-4'-yl]carbonyl}pyrrolidin-3-yl)pyridine;
3-(1-{[4''-fluoro-3,5-bis(trifluoromethyl)-1,1':2',1''-terphenyl-4'-yl]carbonyl}pyrrolidin-3-yl)pyridine;
3-(1-{[4''-(trifluoromethoxy)-3,5-bis(trifluoromethyl)-1,1':2',1''-terphenyl-4'-yl]carbonyl}pyrrolidin-3-yl)pyridine;
3-(1-{[2-pyridin-3-yl-3',5'-bis(trifluoromethyl)biphenyl-4-yl]carbonyl}pyrrolidin-3-yl)pyridine;
3-(1-{[2-pyridin-4-yl-3',5'-bis(trifluoromethyl)biphenyl-4-yl]carbonyl}pyrrolidin-3-yl)pyridine;
3-fluoro-5-[4-[(3-pyridin-3-ylpyrrolidin-1-yl)carbonyl]-3',5'-bis(trifluoromethyl)biphenyl-2-yl]pyridine;
5-[4-[(3-pyridin-3-ylpyrrolidin-1-yl)carbonyl]-3',5'-bis(trifluoromethyl)biphenyl-2-yl]nicotinonitrile;
5-[4-[(3-pyridin-3-ylpyrrolidin-1-yl)carbonyl]-3',5'-bis(trifluoromethyl)biphenyl-2-yl]pyridine-2-carbonitrile;
2-methoxy-5-[4-[(3-pyridin-3-ylpyrrolidin-1-yl)carbo-nyl]-3',5'-bis(trifluoromethyl)biphenyl-2-yl]pyridine;
5-[4-[(3-pyridin-3-ylpyrrolidin-1-yl)carbonyl]-3',5'-bis(trifluoromethyl)biphenyl-2-yl]pyridin-2-amine;
2-methoxy-3-[4-[(3-pyridin-3-ylpyrrolidin-1-yl)carbo-nyl]-3',5'-bis(trifluoromethyl)biphenyl-2-yl]pyridine;
2-[4-[(3-pyridin-3-ylpyrrolidin-1-yl)carbonyl]-3',5'-bis(trifluoromethyl)biphenyl-2-yl]pyridine;
3-(1-{[4''-(2,2,2-trifluoroethoxy)-3,5-bis(trifluorom-ethyl)-1,1':2',1''-terphenyl-4'-yl]carbonyl}pyrrolidin-3-yl)pyridine;
5-[4-[(3-pyridin-3-ylpyrrolidin-1-yl)carbonyl]-3',5'-bis(trifluoromethyl)biphenyl-2-yl]-2-(2,2,2-trifluoroet-hoxy)pyridine;
2-(cyclopropylmethoxy)-5-[4-[(3-pyridin-3-ylpyrrolidin-1-yl)carbonyl]-3',5'-bis(trifluoromethyl)biphenyl-2-yl]pyridine;
5-[4-[(3-pyridin-3-ylpyrrolidin-1-yl)carbonyl]-3',5'-bis(trifluoromethyl)biphenyl-2-yl]pyrimidine;
5-[4-[(3-pyridin-3-ylpyrrolidin-1-yl)carbonyl]-3',5'-bis(trifluoromethyl)biphenyl-2-yl]pyrimidin-2-amine;
5-methoxy-2-[4-[(3-pyridin-3-ylpyrrolidin-1-yl)carbo-nyl]-3',5'-bis(trifluoromethyl)biphenyl-2-yl]pyrimi-dine;
2-[4-[(3-pyridin-3-ylpyrrolidin-1-yl)carbonyl]-3',5'-bis(trifluoromethyl)biphenyl-2-yl]-5-(trifluoromethyl)py-rimidine;
5-[4-[(3-pyridin-3-ylpyrrolidin-1-yl)carbonyl]-3',5'-bis(trifluoromethyl)biphenyl-2-yl]pyrazin-2-amine;
3-(1-{[2-(1,3-oxazol-2-yl)-3',5'-bis(trifluoromethyl)bi-phenyl-4-yl]carbonyl}pyrrolidin-3-yl)pyridine;
3-(1-{[2-(1H-pyrazol-3-yl)-3',5'-bis(trifluoromethyl)bi-phenyl-4-yl]carbonyl}pyrrolidin-3-yl)pyridine;
3-(1-{[2-(1H-pyrazol-4-yl)-3',5'-bis(trifluoromethyl)bi-phenyl-4-yl]carbonyl}pyrrolidin-3-yl)pyridine;
3-(1-{[2-(1-benzothien-2-yl)-3',5'-bis(trifluoromethyl)bi-phenyl-4-yl]carbonyl}pyrrolidin-3-yl)pyridine;
3-(1-{[2-(5-methyl-1,2,4-oxadiazol-3-yl)-3',5'-bis(trif-luoromethyl)biphenyl-4-yl]carbonyl}pyrrolidin-3-yl)pyridine;
3-pyridin-3-yl-1-{[2-pyridin-3-yl-3',5'-bis(trifluorom-ethyl)biphenyl-4-yl]carbonyl}pyrrolidin-3-ol;
3-pyridin-3-yl-1-{[2-pyrimidin-5-yl-3',5'-bis(trifluorom-ethyl)biphenyl-4-yl]carbonyl}pyrrolidin-3-ol;
3-{1-[(2-methoxybiphenyl-4-yl)carbonyl]pyrrolidin-3-yl}pyridine;
5-{2',4'-dichloro-4-[(3-pyridin-3-ylpyrrolidin-1-yl)carbo-nyl]biphenyl-2-yl}pyrimidine;
5-[4-[(3-pyridin-3-ylpyrrolidin-1-yl)carbonyl]-4'-(2,2,2-trifluoroethoxy)biphenyl-2-yl]pyrimidine;
5-{2-[6-(cyclopropylmethoxy)pyridin-3-yl]-5-[(3-pyri-din-3-ylpyrrolidin-1-yl)carbonyl]phenyl}pyrimidine;
3-(1-{[6-(5-cyclopropyl-1,2,4-oxadiazol-3-yl)biphenyl-3-yl]carbonyl}pyrrolidin-3-yl)pyridine;
3-{1-[(3',5'-dimethyl-2-pyridin-3-ylbiphenyl-4-yl)carbo-nyl]pyrrolidin-3-yl}pyridine;
5-{3',5'-dimethyl-4-[(3-pyridin-3-ylpyrrolidin-1-yl)car-bonyl]biphenyl-2-yl}pyrimidine;
3-(1-{[2-isopropoxy-3',5'-bis(trifluoromethyl)biphenyl-4-yl]carbonyl}pyrrolidin-3-yl)pyridine;
3-(1-{[2-methoxy-3',5'-bis(trifluoromethyl)biphenyl-4-yl]carbonyl}pyrrolidin-3-yl)pyridine;
3-(1-{[2-ethoxy-3',5'-bis(trifluoromethyl)biphenyl-4-yl]carbonyl}pyrrolidin-3-yl)pyridine;
3-(1-{[2-(benzyloxy)-3',5'-bis(trifluoromethyl)biphenyl-4-yl]carbonyl}pyrrolidin-3-yl)pyridine;
4-[(3-pyridin-3-ylpyrrolidin-1-yl)carbonyl]-3',5'-bis(trif-luoromethyl)biphenyl-2-carbonitrile;
4-[(3-pyridin-3-ylpyrrolidin-1-yl)carbonyl]biphenyl-2-carbonitrile;
5-[(3-pyridin-3-ylpyrrolidin-1-yl)carbonyl]biphenyl-2-carbonitrile;
methyl 4-[(3-pyridin-3-ylpyrrolidin-1-yl)carbonyl]-3',5'-bis(trifluoromethyl)biphenyl-2-carboxylate;
4-[(3-pyridin-3-ylpyrrolidin-1-yl)carbonyl]-3',5'-bis(trif-luoromethyl)biphenyl-2-carboxylic acid;
N-(2-hydroxy-2-methylpropyl)-4-[(3-pyridin-3-ylpyrroli-din-1-yl)carbonyl]-3',5'-bis(trifluoromethyl)biphenyl-2-carboxamide;
methyl 4-[(3-pyridin-3-ylpyrrolidin-1-yl)carbonyl]biphe-nyl-2-carboxylate;
N-cyclopropyl-4-[(3-pyridin-3-ylpyrrolidin-1-yl)carbo-nyl]-3',5'-bis(trifluoromethyl)biphenyl-2-carboxamide;
4-{[4-[(3-pyridin-3-ylpyrrolidin-1-yl)carbonyl]-3',5'-bis(trifluoromethyl)biphenyl-2-yl]carbonyl}morpholine;
2-[4-[(3-pyridin-3-ylpyrrolidin-1-yl)carbonyl]-3',5'-bis(trifluoromethyl)biphenyl-2-yl]propan-2-ol;
4-[(3-pyridin-3-ylpyrrolidin-1-yl)carbonyl]-3',5'-bis(trif-luoromethyl)biphenyl-2-carbohydrazide;
5-[4-[(3-pyridin-3-ylpyrrolidin-1-yl)carbonyl]-3',5'-bis(trifluoromethyl)biphenyl-2-yl]-1,3,4-oxadiazol-2 (3H)-one;
3-(1-{[2-(1H-pyrazol-1-yl)-3',5'-bis(trifluoromethyl)bi-phenyl-4-yl]carbonyl}pyrrolidin-3-yl)pyridine;
5-[4-[(3-pyridin-3-ylpyrrolidin-1-yl)carbonyl]-3',5'-bis(trifluoromethyl)biphenyl-2-yl]pyridin-2-ol; and
5-[4-[(3-hydroxy-3-pyridin-3-ylpyrrolidin-1-yl)carbo-nyl]-3',5'-bis(trifluoromethyl)biphenyl-2-yl]pyridin-2-ol;
and the pharmaceutically acceptable salts thereof.

17. The compound of claim 1 selected from the group consisting of:
- 3-(1-{[3',5'-bis(trifluoromethyl)biphenyl-4-yl] carbonyl}pyrrolidin-3-yl)pyridine;
- 2-{4-[(3-pyridin-3-ylpyrrolidin-1-yl)carbonyl]phenyl}-5-(trifluoromethyl)pyrimidine;
- 3-[1-(biphenyl-4-ylcarbonyl)pyrrolidin-3-yl]pyridine;
- 3-{1-[(3',5'-dimethylbiphenyl-4-yl)carbonyl]pyrrolidin-3-yl}pyridine;
- 3-{1-[(3'-fluorobiphenyl-4-yl)carbonyl]pyrrolidin-3-yl}pyridine;
- 3-{1-[(4'-fluorobiphenyl-4-yl)carbonyl]pyrrolidin-3-yl}pyridine;
- 3-{1-[(3',4'-dichlorobiphenyl-4-yl)carbonyl]pyrrolidin-3-yl}pyridine;
- 3-{1-[(2',5'-dichlorobiphenyl-4-yl)carbonyl]pyrrolidin-3-yl}pyridine;
- 3-{1-[(3',5'-dichlorobiphenyl-4-yl)carbonyl]pyrrolidin-3-yl}pyridine;
- 3-{1-[(2',4'-dichlorobiphenyl-4-yl)carbonyl]pyrrolidin-3-yl}pyridine;
- 3-{1-[(2',3',5'-trichlorobiphenyl-4-yl)carbonyl]pyrrolidin-3-yl}pyridine;
- 3-(1-{[3'-(trifluoromethyl)biphenyl-4-yl] carbonyl}pyrrolidin-3-yl)pyridine;
- 3-(1-{[4'-(trifluoromethyl)biphenyl-4-yl] carbonyl}pyrrolidin-3-yl)pyridine;
- 3-(1-{[3'-(trifluoromethoxy)biphenyl-4-yl] carbonyl}pyrrolidin-3-yl)pyridine;
- 3-(1-{[4'-(trifluoromethoxy)biphenyl-4-yl] carbonyl}pyrrolidin-3-yl)pyridine;
- 3-{1-[(2'-methoxybiphenyl-4-yl)carbonyl]pyrrolidin-3-yl}pyridine;
- 3-{1-[(2',4'-diethoxybiphenyl-4-yl)carbonyl]pyrrolidin-3-yl}pyridine;
- 3-{1-[(4'-methoxy-3',5'-dimethylbiphenyl-4-yl)carbonyl] pyrrolidin-3-yl}pyridine;
- 3-{1-[(4'-ethoxy-3',5'-dimethylbiphenyl-4-yl)carbonyl] pyrrolidin-3-yl}pyridine;
- 3-(1-{[3'-fluoro-5'-(trifluoromethyl)biphenyl-4-yl] carbonyl}pyrrolidin-3-yl)pyridine;
- 3-(1-{[4'-methoxy-3'-(trifluoromethyl)biphenyl-4-yl] carbonyl}pyrrolidin-3-yl)pyridine;
- 3-(1-{[3'-methoxy-5'-(trifluoromethyl)biphenyl-4-yl] carbonyl}pyrrolidin-3-yl)pyridine;
- 3-[1-(4-pyridin-3-ylbenzoyl)pyrrolidin-3-yl]pyridine;
- 3-[1-(4-pyridin-4-ylbenzoyl)pyrrolidin-3-yl]pyridine;
- 2-methoxy-3-{4-[(3-pyridin-3-ylpyrrolidin-1-yl)carbonyl]phenyl}pyridine;
- 2-chloro-3-{4-[(3-pyridin-3-ylpyrrolidin-1-yl)carbonyl] phenyl}-6-trifluoromethyl)pyridine;
- 3-{4-[(3-pyridin-3-ylpyrrolidin-1-yl)carbonyl]phenyl}-2,6-bis(trifluoromethyl)pyridine;
- 5-chloro-2-fluoro-3-{4-[(3-pyridin-3-ylpyrrolidin-1-yl) carbonyl]phenyl}pyridine;
- 3-{4-[(3-pyridin-3-ylpyrrolidin-1-yl)carbonyl] phenyl}quinoline;
- 6-{4-[(3-pyridin-3-ylpyrrolidin-1-yl)carbonyl] phenyl}quinoline;
- 8-{4-[(3-pyridin-3-ylpyrrolidin-1-yl)carbonyl] phenyl}quinoline;
- 5,6-difluoro-2-methyl-8-{4-[(3-pyridin-3-ylpyrrolidin-1-yl)carbonyl]phenyl}quinoline;
- 5-{4-[(3-pyridin-3-ylpyrrolidin-1-yl)carbonyl] phenyl}isoquinoline;
- 5-{4-[(3-pyridin-3-ylpyrrolidin-1-yl)carbonyl] phenyl}pyrimidine;
- 5-{4-[(3-pyridin-3-ylpyrrolidin-1-yl)carbonyl] phenyl}pyrimidin-2-amine;
- 2-methoxy-5-{4-[(3-pyridin-3-ylpyrrolidin-1-yl)carbonyl]phenyl}pyrimidine;
- 5-{4-[(3-pyridin-3-ylpyrrolidin-1-yl)carbonyl] phenyl}pyrazin-2-amine;
- 3-{1-[4-(1H-pyrazol-1-yl)benzoyl]pyrrolidin-3-yl}pyridine;
- 3-{1-[4-(3,5-dimethyl-1H-pyrazol-1-yl)benzoyl]pyrrolidin-3-yl}pyridine;
- 3-[1-(biphenyl-3-ylcarbonyl)pyrrolidin-3-yl]pyridine;
- 3-{1-[(3'-fluorobiphenyl-3-yl)carbonyl]pyrrolidin-3-yl}pyridine;
- 3-{1-[(4'-fluorobiphenyl-3-yl)carbonyl]pyrrolidin-3-yl}pyridine;
- 3-(1-{[3',5'-bis(trifluoromethyl)biphenyl-3-yl] carbonyl}pyrrolidin-3-yl)pyridine;
- 3-(1-{[3'-(trifluoromethoxy)biphenyl-3-yl] carbonyl}pyrrolidin-3-yl)pyridine;
- 3-(1-{[4'-(trifluoromethoxy)biphenyl-3-yl] carbonyl}pyrrolidin-3-yl)pyridine;
- 3-[1-(3-pyridin-3-ylbenzoyl)pyrrolidin-3-yl]pyridine;
- 3-[1-(3-pyridin-4-ylbenzoyl)pyrrolidin-3-yl]pyridine;
- 3-{3-[(3-pyridin-3-ylpyrrolidin-1-yl)carbonyl] phenyl}quinoline;
- 6-{3-[(3-pyridin-3-ylpyrrolidin-1-yl)carbonyl] phenyl}quinoline;
- 8-{3-[(3-pyridin-3-ylpyrrolidin-1-yl)carbonyl] phenyl}quinoline;
- 5-{3-[(3-pyridin-3-ylpyrrolidin-1-yl)carbonyl] phenyl}isoquinoline;
- 5-{3-[(3-pyridin-3-ylpyrrolidin-1-yl)carbonyl] phenyl}pyrazin-2-amine;
- 3-{1-[(3-fluorobiphenyl-4-yl)carbonyl]pyrrolidin-3-yl}pyridine;
- 3-(1-{[3-fluoro-3',5'-bis(trifluoromethyl)biphenyl-4-yl] carbonyl}pyrrolidin-3-yl)pyridine;
- 3-{1-[(3-methylbiphenyl-4-yl)carbonyl]pyrrolidin-3-yl}pyridine;
- 3-(1-{[3-methyl-3',5'-bis(trifluoromethyl)biphenyl-4-yl] carbonyl}pyrrolidin-3-yl)pyridine;
- 3-{3-methyl-4-[(3-pyridin-3-ylpyrrolidin-1-yl)carbonyl] phenyl}quinoline;
- 8-{3-methyl-4-[(3-pyridin-3-ylpyrrolidin-1-yl)carbonyl] phenyl}quinoline;
- 3-{1-[(2-fluorobiphenyl-4-yl)carbonyl]pyrrolidin-3-yl}pyridine;
- 3-(1-{[2-fluoro-3',5'-bis(trifluoromethyl)biphenyl-4-yl] carbonyl}pyrrolidin-3-yl)pyridine;
- 3-{1-[(2-methylbiphenyl-4-yl)carbonyl]pyrrolidin-3-yl}pyridine;
- 3-(1-{[2-methyl-3',5'-bis(trifluoromethyl)biphenyl-4-yl] carbonyl}pyrrolidin-3-yl)pyridine;
- 3-(1-{[2,3',5'-tris(trifluoromethyl)biphenyl-4-yl] carbonyl}pyrrolidin-3-yl)pyridine;
- 3-{1-[(6-iodobiphenyl-3-yl)carbonyl]pyrrolidin-3-yl}pyridine;
- 3-{1-[(5-fluorobiphenyl-3-yl]carbonyl}pyrrolidin-3-yl) pyridine;
- 3-{1-[(3',5-difluorobiphenyl-3-yl)carbonyl]pyrrolidin-3-yl}pyridine;
- 6-{3-fluoro-5-[(3-pyridin-3-ylpyrrolidin-1-yl)carbonyl] phenyl}quinoline;
- 3-(1-{[5-(trifluoromethyl)biphenyl-3-yl] carbonyl}pyrrolidin-3-yl)pyridine;
- 3-(1-{[3'-fluoro-5-(trifluoromethyl)biphenyl-3-yl] carbonyl}pyrrolidin-3-yl)pyridine;

3-(1-{[3',5-bis(trifluoromethyl)biphenyl-3-yl]carbonyl}pyrrolidin-3-yl)pyridine;
3-(1-{[4',5-bis(trifluoromethyl)biphenyl-3-yl]carbonyl}pyrrolidin-3-yl)pyridine;
3-(1-{[3',5,5'-tris(trifluoromethyl)biphenyl-3-yl]carbonyl}pyrrolidin-3-yl)pyridine;
5-[3-[(3-pyridin-3-ylpyrrolidin-1-yl)carbonyl]-5-(trifluoromethyl)phenyl]pyrimidine;
6-[3-[(3-pyridin-3-ylpyrrolidin-1-yl)carbonyl]-5-(trifluoromethyl)phenyl]quinoline;
5-[3-[(3-pyridin-3-ylpyrrolidin-1-yl)carbonyl]-5-(trifluoromethyl)phenyl]-1H-indole;
4-(1-{[3',5'-bis(trifluoromethyl)biphenyl-4-yl]carbonyl}pyrrolidin-3-yl))-4H-1,2,4-triazole;
3-(1-{[3',5'-bis(trifluoromethyl)biphenyl-4-yl]carbonyl}pyrrolidin-3-yl)-5-methylpyridine;
3-(1-{[3',5'-bis(trifluoromethyl)biphenyl-4-yl]carbonyl}pyrrolidin-3-yl)-5-fluoropyridine;
3-(1-{[3',5'-bis(trifluoromethyl)biphenyl-4-yl]carbonyl}pyrrolidin-3-yl)-5-methoxypyridine;
3-{1-[(6-methylbiphenyl-3-yl)carbonyl]pyrrolidin-3-yl}pyridine;
3-{1-[(3'-fluoro-6-methylbiphenyl-3-yl)carbonyl]pyrrolidin-3-yl}pyridine;
3-(1-{[2-(trifluoromethyl)biphenyl-4-]carbonyl}pyrrolidin-3-yl)pyridine;
3-{1-[(2-methoxybiphenyl-4-yl)carbonyl]pyrrolidin-3-yl}pyridine;
3-(1-{[2-cyclopropyl-3',5'-bis(trifluoromethyl)biphenyl-4-yl]carbonyl}pyrrolidin-3-yl)pyridine;
3-{1-[(2-cyclopropylbiphenyl-4-yl)carbonyl]pyrrolidin-3-yl)}pyridine;
3-{1-[(6-cyclopropylbiphenyl-3-yl)carbonyl]pyrrolidin-3-yl}pyridine; and
and the pharmaceutically acceptable salts thereof.

18. The compound of claim 1 selected from the group consisting of:
2-(1-{[3',5'-bis(trifluoromethyl)biphenyl-4yl]carbonyl}pyrrolidin-3yl)-5-methyl-1,3,4-oxadiazole; and
2-(1-{[2-cyclopropyl-3',5'-bis(trifluoromethyl)biphenyl-4-yl]carbonyl}pyrrolidin-3-yl)-5-methyl-1,3,4-oxadiazole;
and the pharmaceutically acceptable salts thereof.

19. A pharmaceutical composition comprised of a therapeutically effective amount of a compound of claim 1 and a pharmaceutically acceptable carrier, optionally comprised of a therapeutically effective amount of one or more additional active agents.

20. The compound of claim 1 wherein the $R^1$ ring is attached within the Formula I structure via a carbon atom in the $R^1$ ring.

21. The compound of claim 2 wherein $R^1$ is selected from the group consisting of:

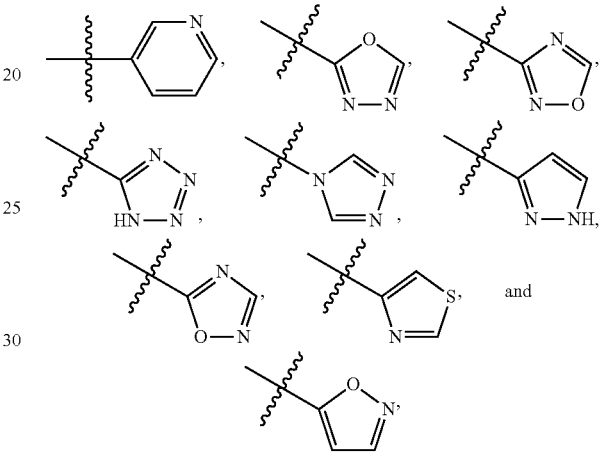

each of witch is optionally substituted with $R^7$.

* * * * *